(12) United States Patent
Mlynarski et al.

(10) Patent No.: US 11,420,984 B2
(45) Date of Patent: Aug. 23, 2022

(54) ARGINASE INHIBITORS AND METHODS OF USE THEREOF

(71) Applicant: AstraZeneca AB, Sodertalje (SE)

(72) Inventors: Scott Nathan Mlynarski, Waltham, MA (US); Tyler Grebe, Waltham, MA (US); Sameer Kawatkar, Waltham, MA (US); Maurice Raymond Verschoyle Finlay, Cambridge (GB); Iain Simpson, Cambridge (GB); Jianyan Wang, Waltham, MA (US); Steve Cook, Waltham, MA (US); Dedong Wu, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 16/969,739

(22) PCT Filed: Feb. 15, 2019

(86) PCT No.: PCT/IB2019/051236
§ 371 (c)(1),
(2) Date: Aug. 13, 2020

(87) PCT Pub. No.: WO2019/159120
PCT Pub. Date: Aug. 22, 2019

(65) Prior Publication Data
US 2021/0002305 A1 Jan. 7, 2021

Related U.S. Application Data

(60) Provisional application No. 62/778,002, filed on Dec. 11, 2018, provisional application No. 62/671,576, filed on May 15, 2018, provisional application No. 62/631,659, filed on Feb. 17, 2018, provisional application No. 62/721,113, filed on Aug. 22, 2018.

(51) Int. Cl.
*C07F 5/02* (2006.01)
*A61K 31/69* (2006.01)

(52) U.S. Cl.
CPC .................................. *C07F 5/025* (2013.01)

(58) Field of Classification Search
CPC .......... A61K 31/69; A61P 29/00; A61P 35/00; C07F 5/02
USPC .................. 548/405, 409, 410; 514/409, 423
See application file for complete search history.

(56) References Cited

FOREIGN PATENT DOCUMENTS

| WO | 2011/133653 | 10/2011 |
|----|-------------|---------|
| WO | 2016/210106 | 12/2016 |
| WO | 2017/075363 A1 | 5/2017 |
| WO | 2017/191130 A2 | 11/2017 |
| WO | 2018/089490 | 5/2018 |
| WO | 2018/119440 A1 | 6/2018 |
| WO | 2019/120296 A1 | 6/2019 |
| WO | 2019/177873 A1 | 9/2019 |
| WO | 2019/205979 A1 | 10/2019 |
| WO | 2019/218904 A1 | 11/2019 |
| WO | 2019/245890 A1 | 12/2019 |

OTHER PUBLICATIONS

International Search Report and Written Opinion for corresponding PCT/IB2019/051236 dated May 6, 2019.

*Primary Examiner* — Charanjit Aulakh

(57) ABSTRACT

Disclosed are compounds of formula (Ia) or a pharmaceutically acceptable salt thereof, pharmaceutical compositions comprising compounds of formula (Ia) and methods of using the same for treating cancer or a respiratory inflammatory disease and inhibiting arginase:

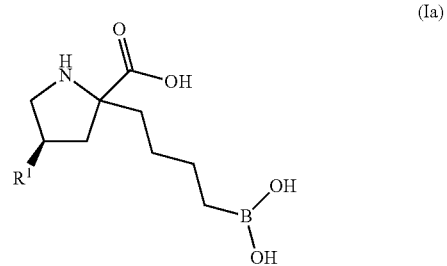

(Ia)

wherein
$R^1$ is $-NHR^{1a}$;
$R^{1a}$ is $-H$ or $-C(O)CH(R^{1b})NHR^{1c}$;
$R^{1b}$ is selected from $-H$, $-(C_1\text{-}C_4)$ alkyl and $CH_2OR^{1d}$;
$R^{1c}$ is $-H$; or $R^{1b}$ and $R^{1c}$, together with the atom to which they are attached, form a 5-membered heterocyclic ring; and
$R^{1d}$ is H or $-CH_3$.

19 Claims, 3 Drawing Sheets

ARGINASE INHIBITORS AND METHODS OF USE THEREOF

CROSS-REFERENCE TO RELATED APPLICATIONS

This application is a U.S. National Stage application of International Application No. PCT/IB2019/051236, filed on Feb. 15, 2019, said International Application No. PCT/IB2019/051236 claims benefit under 35 U.S.C. § 119(e) of the U.S. Provisional Application Nos. 62/631,659, filed Feb. 17, 2018; 62/671,576 filed May 15, 2018, 62/778,002, filed Dec. 11, 2018 and 62/721,113, filed Aug. 22, 2018. Each of the above listed applications is incorporated by reference herein in its entirety for all purposes.

REFERENCE TO THE SEQUENCE LISTING

This application incorporates by reference a Sequence Listing submitted with this application as text file entitled, created on, and having a size of kilobytes.

BACKGROUND

Arginase is a manganese metalloenzyme that catalyzes the conversion of L-arginine to urea and L-ornithine. Two isoforms exist: Arginase 1 is a cytosolic enzyme predominantly found in hepatocytes where it plays a critical role in removing ammonia through urea synthesis, and Arginase 2, a mitochondrial enzyme highly expressed in kidney involved in production of ornithine, a precursor for polyamines and prolines important for cell proliferation and collagen production, respectively.

Although L-arginine is not an essential amino acid as it can be provided through protein turnover in healthy adults, increased expression and secretion of arginases results in reduced L-arginine levels in various physiologic and pathologic conditions (e.g., pregnancy, auto-immune diseases, cancer). Immune cells, in particular, are sensitive to reduced L-arginine levels. T-cells, when faced with a low L-arginine microenvironment, reduce their proliferation rate and lower the expression of CD3ζ chain, IFNγ, and lytic enzymes resulting in impaired T-cell responsiveness. Dendritic cells respond to low L-arginine conditions by reducing their ability to present antigens, and natural killer cells reduce both proliferation and expression of lytic enzymes.

Tumors use multiple immune suppressive mechanisms to evade the immune system. One of these is the reduction of L-arginine through increased levels of circulating arginase, increased expression and secretion of arginase by tumor cells, and recruitment of arginase expressing and secreting myeloid derived suppressor cells. Together, these lead to a reduction of L-arginine in the tumor microenvironment and an immune-suppressive phenotype. Pharmacologic inhibition of arginase activity has been shown to reverse the low L-arginine induced immune suppression in animal models. As such, there is a need for potent and selective arginase inhibitors to reverse immune suppression and re-activate anti-cancer immunity in patients, either as single agent, or in combination with therapies reversing additional immune-suppressive mechanisms.

SUMMARY

In one embodiment, disclosed is a compound of formula (I), or a pharmaceutically acceptable salt thereof:

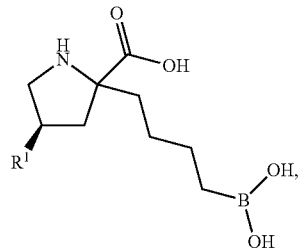

(I)

wherein
$R^1$ is —$NHR^{1a}$;
$R^{1a}$ is —H or —$C(O)CH(R^{1b})NH_2$; and
$R^{1b}$ is —$CH_3$ or —$CH(CH_3)_2$.

In one embodiment, disclosed is a compound of formula (Ia), or a pharmaceutically acceptable salt thereof:

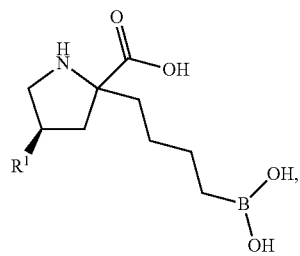

(Ia)

wherein
$R^1$ is —$NHR^{1a}$;
$R^{1a}$ is —H or —$C(O)CH(R^{1b})NHR^{1c}$; and
$R^{1b}$ is selected from —H, —($C_1$-$C_4$) alkyl and $CH_2OR^{1d}$ and $R^{1c}$ is —H; or
$R^{1b}$ and $R^{1c}$, together with the atom to which they are attached, form a 5-membered heterocyclic ring; and
$R^{1d}$ is H or —$CH_3$.

In one embodiment, disclosed is a compound of formula (Ib), or a pharmaceutically acceptable salt thereof:

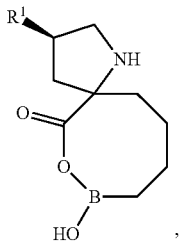

(Ib)

wherein
$R^1$ is —$NHR^{1a}$; $R^{1a}$ is —H or —$C(O)CH(R^{1b})NHR^{1c}$; and
$R^{1b}$ is selected from —H, —($C_1$-$C_4$) alkyl and $CH_2OR^{1d}$ and $R^{1c}$ is —H; or
$R^{1b}$ and $R^{1c}$, together with the atom to which they are attached, form a 5-membered heterocyclic ring; and
$R^{1d}$ is H or —$CH_3$.

In one embodiment, disclosed is a compound of formula (II), or a pharmaceutically acceptable salt thereof:

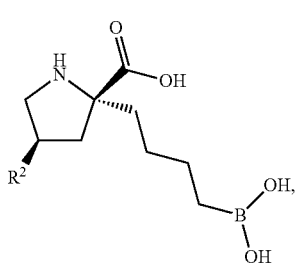
(II)

wherein
$R^2$ is —OH or —NHR$^{2a}$;
$R^{2a}$ is —H or —C(O)CH(R$^{2b}$)NH$_2$; and
$R^{2b}$ is —CH$_3$ or —CH(CH$_3$)$_2$.

In one embodiment, disclosed is a compound of formula (IIa), or a pharmaceutically acceptable salt thereof:

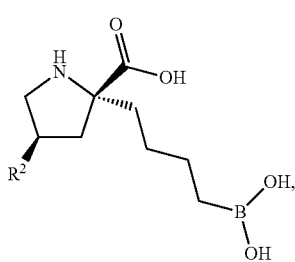
(IIa)

wherein
$R^2$ is —OH or —NHR$^{2a}$;
$R^{2a}$ is —H or —C(O)CH(R$^{2b}$)NHR$^{2c}$;
$R^{2b}$ is selected from —H, —(C$_1$-C$_4$) alkyl and CH$_2$OR$^{2d}$ and R$^{2c}$ is —H; or
$R^{2b}$ and $R^{2c}$, together with the atoms to which they are attached, form a 5-membered heterocyclic ring; and
$R^{2d}$ is —H or —CH$_3$.

In one embodiment, disclosed is a compound of formula (IIb), or a pharmaceutically acceptable salt thereof:

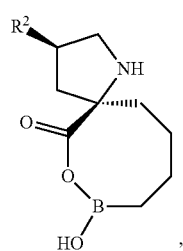
(IIb)

wherein
$R^2$ is —OH or —NHR$^{2a}$;
$R^{2a}$ is —H or —C(O)CH(R$^{2b}$)NHR$^{2c}$;
$R^{2b}$ is selected from —H, —(C$_1$-C$_4$) alkyl and CH$_2$OR$^{2d}$ and R$^{2c}$ is —H; or
$R^{2b}$ and $R^{2c}$, together with the atoms to which they are attached, form a 5-membered heterocyclic ring; and
$R^{2d}$ is —H or —CH$_3$.

In some embodiments, disclosed is a compound of formula (III), or a pharmaceutically acceptable salt thereof:

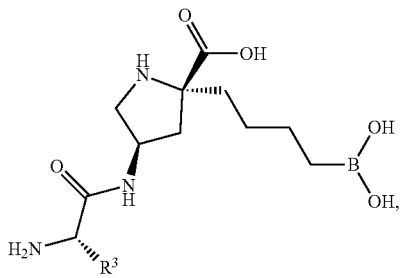
(III)

wherein $R^3$ is —CH$_3$ or —CH(CH$_3$)$_2$.

In some embodiments, disclosed is a compound of formula (IIIa), or a pharmaceutically acceptable salt thereof:

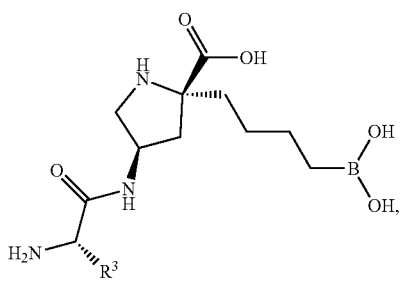
(IIIa)

wherein
$R^3$ is selected from —H, —(C$_1$-C$_4$) alkyl and —CH$_2$OR$^{3a}$; and
$R^{3a}$ is —H or —CH$_3$.

In one embodiment, disclosed is a compound of formula (IIIb), or a pharmaceutically acceptable salt thereof:

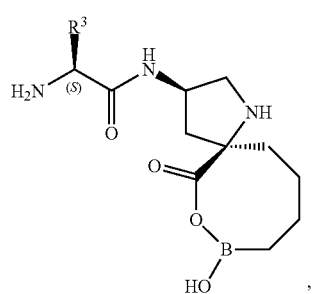
(IIIb)

wherein
$R^3$ is selected from —H, —(C$_1$-C$_4$) alkyl and —CH$_2$OR$^{3a}$; and
$R^{3a}$ is —H or —CH$_3$.

In some embodiments, disclosed is a compound of formula (IV), or a pharmaceutically acceptable salt thereof:

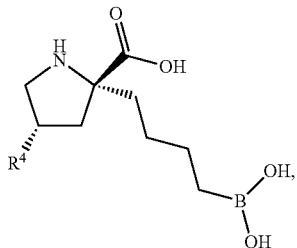

(IV)

wherein R⁴ is —OH or —NH₂.

In one embodiment, disclosed is a compound of formula (IVb), or a pharmaceutically acceptable salt thereof:

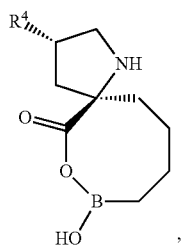

(IVb)

wherein R⁴ is —OH or —NH₂.

In some embodiments, disclosed is a compound of formula (V), or a pharmaceutically acceptable salt thereof:

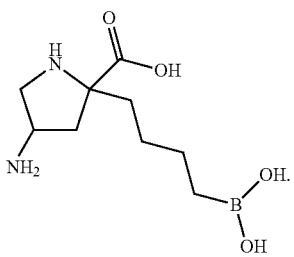

(V)

In one embodiment, disclosed is a compound of formula (Vb), or a pharmaceutically acceptable salt thereof:

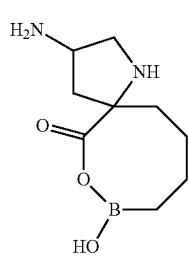

(Vb)

In one embodiment, disclosed is a compound of formula (VI), or a pharmaceutically acceptable salt thereof:

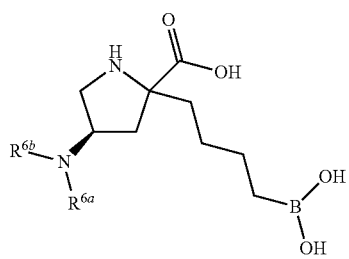

(VI)

wherein
$R^{6a}$ is —H or —CH₃;
$R^{6b}$ is —C(O)C($R^{6c}R^{6d}$)NH₂; or —(C₁-C₃) alkyl which is substituted with 0 or 1 amino or —$OR^{6e}$; and
$R^{6c}$ is —(C₁-C₃) alkyl which is substituted with 0 or 1 amino or —$OR^{6f}$;
$R^{6d}$ is H or —CH₃; and
$R^{6e}$ and $R^{6f}$ are independently —H or —CH₃.

In one embodiment, disclosed is a compound of formula (VIb), or a pharmaceutically acceptable salt thereof:

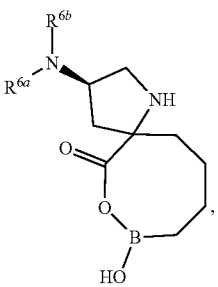

(VIb)

wherein
$R^{6a}$ is —H or —CH₃;
$R^{6b}$ is —C(O)C($R^{6c}R^{6d}$)NH₂; or —(C₁-C₃) alkyl which is substituted with 0 or 1 amino or —$OR^{6e}$; and
$R^{6c}$ is —(C₁-C₃) alkyl which is substituted with 0 or 1 amino or —$OR^{6f}$;
$R^{6d}$ is H or —CH₃; and
$R^{6e}$ and $R^{6f}$ are independently —H or —CH₃.

In some embodiments, disclosed are the compounds of Table 1, or a pharmaceutically acceptable salt thereof.

In some embodiments, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, and a pharmaceutically acceptable carrier.

In some embodiments, disclosed are methods of treating cancer comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof.

In some embodiments, disclosed are compounds of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for treating cancer.

In some embodiments, disclosed is the use of a compound of (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof in the manufacture of a medicament for use in treating cancer.

In some embodiments, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating cancer.

In some embodiments, disclosed are methods of treating a respiratory inflammatory disease comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof.

In some embodiments, disclosed are compounds of formula (I), (Ia), (Ib), (II), (IIa), (IIb), (III), (IIIa), (IIIb), (IV), (IVb), (V), (Vb), (VI), (VIb), including any subgenera or species thereof, or
Table 1, or a pharmaceutically acceptable salt thereof, for treating a respiratory inflammatory disease.

In some embodiments, disclosed is the use of a compound of (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof in the manufacture of a medicament for use in treating a respiratory inflammatory disease.

In some embodiments, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating a respiratory inflammatory disease.

In some embodiments, the aforementioned respiratory inflammatory disease is chronic obstructive pulmonary disease (COPD) or asthma.

DETAILED DESCRIPTION

Compounds

Figure 1:
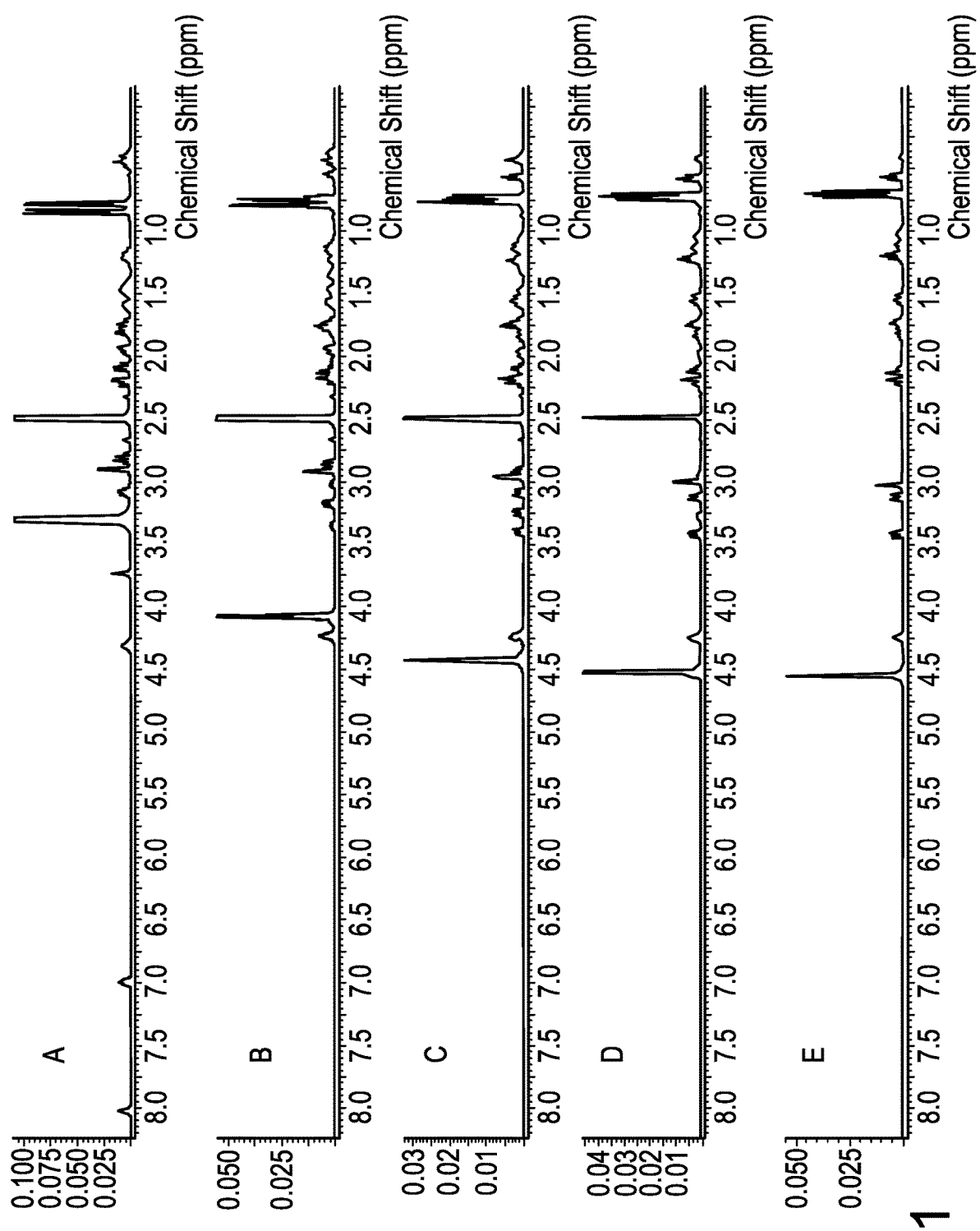
FIG. 1 shows NMR spectra depicting the conversion of compound B to compound A where compound B is prepared in 100% d6-DMSO (labeled A), 75% $D_2O$ in d6-DMSO (labeled B), 50% $D_2O$ in d6-DMSO (labeled C), 25% $D_2O$ in d6-DMSO (labeled E) and 100% $D_2O$ (labeled F).

In one embodiment, disclosed is a compound of formula (I), or a pharmaceutically acceptable salt thereof:

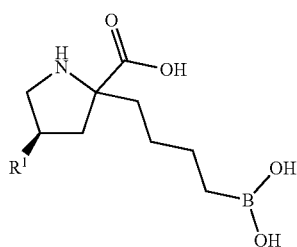

(I)

wherein
$R^1$ is —$NHR^{1a}$;
$R^{1a}$ is —H or —$C(O)CH(R^{1b})NH_2$; and
$R^{1b}$ is —$CH_3$ or —$CH(CH_3)_2$.

In one embodiment, disclosed is a compound of formula (I). In another embodiment, disclosed is a pharmaceutically acceptable salt of the compound of formula (I).

In some embodiments of formula (I), $R^1$ is —$NHR^{1a}$ and $R^{1a}$ is —H.

In some embodiments of formula (I), $R^1$ is —$NHR^{1a}$, $R^{1a}$ is —$C(O)CH(R^{1b})NH_2$ and $R^{1b}$ is —$CH_3$.

In some embodiments of formula (I), $R^1$ is —$NHR^{1a}$, $R^{1a}$ is —$C(O)CH(R^{1b})NH_2$ and $R^{1b}$ is —$CH(CH_3)_2$.

In one embodiment, disclosed is a compound of formula (Ia), or a pharmaceutically acceptable salt thereof:

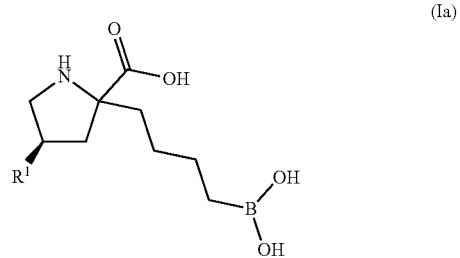

(Ia)

wherein
$R^1$ is —$NHR^{1a}$;
$R^{1a}$ is —H or —$C(O)CH(R^{1b})NHR^{1c}$; and
$R^{1b}$ is selected from —H, —$(C_1-C_4)$ alkyl and $CH_2OR^{1d}$; and $R^{1c}$ is —H; or
$R^{1b}$ and $R^{1c}$, together with the atom to which they are attached, form a 5-membered ring; and
$R^{1d}$ is H or —$CH_3$.

In one embodiment, disclosed is a compound of formula (Ia). In another embodiment, disclosed is a pharmaceutically acceptable salt of the compound of formula (Ia).

In some embodiments, a compound of formula (Ia) is represented by formula (Ia1) or (Ia2):

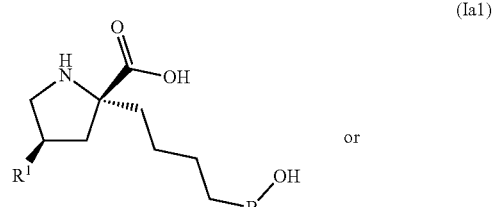

(Ia1)

or

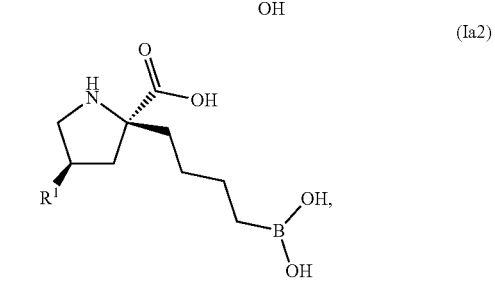

(Ia2)

wherein $R^1$ is the same as defined above.

In some embodiments of formula (Ia), $R^{1a}$ is —H.

In some embodiments of formula (Ia), $R^{1a}$ is —C(O)CH$(R^{1b})$NHR$^{1c}$; $R^{1b}$ is —H and $R^{1c}$ is —H.

In some embodiments of formula (Ia), $R^{1a}$ is —C(O)CH$(R^{1b})$NHR$^{1c}$; $R^{1b}$ is CH$_2$OR$^{1d}$; $R^{1c}$ is —H and $R^{1d}$ is —H.

In some embodiments of formula (Ia), $R^{1a}$ is —C(O)CH$(R^{1b})$NHR$^{1c}$; $R^{1b}$ is CH$_2$OR$^{1d}$; $R^{1c}$ is —H and $R^{1d}$ is CH$_3$.

In some embodiments of formula (Ia), $R^{1a}$ is —C(O)CH$(R^{1b})$NHR$^{1c}$; $R^{1b}$ is —(C$_1$-C$_4$) alkyl and $R^{1c}$ is —H. In some embodiments, the C$_1$-C$_4$ alkyl is selected from methyl, ethyl, isopropyl, sec-butyl, tert-buty and isobutyl.

In some embodiments of formula (Ia), $R^{1a}$ is —C(O)CH$(R^{1b})$NHR$^{1c}$; $R^{1b}$ is methyl; and $R^{1c}$ is —H.

In some embodiments of formula (Ia), $R^{1a}$ is —C(O)CH$(R^{1b})$NHR$^{1c}$; $R^{1b}$ is ethyl; and $R^{1c}$ is —H.

In some embodiments of formula (Ia), $R^{1a}$ is —C(O)CH$(R^{1b})$NHR$^{1c}$; $R^{1b}$ is isopropyl; and $R^{1c}$ is —H.

In some embodiments of formula (Ia), $R^{1a}$ is —C(O)CH$(R^{1b})$NHR$^{1c}$; $R^{1b}$ is sec-butyl; and $R^{1c}$ is —H.

In some embodiments of formula (Ia), $R^{1a}$ is —C(O)CH$(R^{1b})$NHR$^{1c}$; $R^{1b}$ is isobutyl; and $R^{1c}$ is —H.

In some embodiments of formula (Ia), $R^{1a}$ is —C(O)CH$(R^{1b})$NHR$^{1c}$; $R^{1b}$ is tert-butyl; and $R^{1c}$ is —H.

In some embodiments of formula (Ia), $R^{1a}$ is —C(O)CH$(R^{1b})$NHR$^{1c}$ and $R^{1b}$ and $R^{1c}$, together with the atom to which they are attached, form a 5-membered ring.

In one embodiment, disclosed is a compound of formula (Ib), or a pharmaceutically acceptable salt thereof:

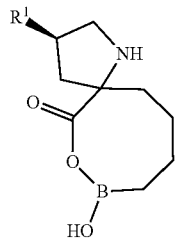

(Ib)

wherein
$R^1$ is —NHR$^{1a}$;
$R^{1a}$ is —H or —C(O)CH$(R^{1b})$NHR$^{1c}$; and
$R^{1b}$ is selected from —H, —(C$_1$-C$_4$) alkyl and CH$_2$OR$^{1d}$; and $R^{1c}$ is —H; or
$R^{1b}$ and $R^{1c}$, together with the atom to which they are attached, form a 5-membered heterocyclic ring; and
$R^{1d}$ is H or —CH$_3$.

In one embodiment, disclosed is a compound of formula (Ib). In another embodiment, disclosed is a pharmaceutically acceptable salt of the compound of formula (Ib).

In some embodiments, a compound of formula (Ib) is represented by formula (Ib1) or (Ib2):

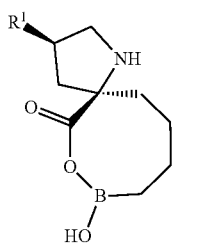

(Ib1)

or

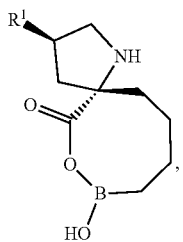

(Ib2)

wherein $R^1$ is the same as defined above.

In some embodiments of formula (Ib), $R^{1a}$ is —H.

In some embodiments of formula (Ib), $R^{1a}$ is —C(O)CH$(R^{1b})$NHR$^{1c}$; $R^{1b}$ is —H and $R^{1c}$ is —H. In some embodiments of formula (Ib), $R^{1a}$ is —C(O)CH$(R^{1b})$NHR$^{1c}$; $R^{1b}$ is CH$_2$OR$^{1d}$; $R^{1c}$ is —H and $R^{1d}$ is —H.

In some embodiments of formula (Ib), $R^{1a}$ is —C(O)CH$(R^{1b})$NHR$^{1c}$; $R^{1b}$ is CH$_2$OR$^{1d}$; $R^{1c}$ is —H and $R^{1d}$ is CH$_3$.

In some embodiments of formula (Ib), $R^{1a}$ is —C(O)CH$(R^{1b})$NHR$^{1c}$; $R^{1b}$ is —(C$_1$-C$_4$) alkyl and $R^{1c}$ is —H. In some embodiments, the C$_1$-C$_4$ alkyl is selected from methyl, ethyl, isopropyl, sec-butyl, tert-buty and isobutyl.

In some embodiments of formula (Ib), $R^{1a}$ is —C(O)CH$(R^{1b})$NHR$^{1c}$; $R^{1b}$ is methyl; and $R^{1c}$ is —H.

In some embodiments of formula (Ib), $R^{1a}$ is —C(O)CH$(R^{1b})$NHR$^{1c}$; $R^{1b}$ is ethyl; and $R^{1c}$ is —H.

In some embodiments of formula (Ib), $R^{1a}$ is —C(O)CH$(R^{1b})$NHR$^{1c}$; $R^{1b}$ is isopropyl; and $R^{1c}$ is —H.

In some embodiments of formula (Ib), $R^{1a}$ is —C(O)CH$(R^{1b})$NHR$^{1c}$; $R^{1b}$ is sec-butyl; and $R^{1c}$ is —H.

In some embodiments of formula (Ib), $R^{1a}$ is —C(O)CH$(R^{1b})$NHR$^{1c}$; $R^{1b}$ is isobutyl; and $R^{1c}$ is —H.

In some embodiments of formula (Ib), $R^{1a}$ is —C(O)CH$(R^{1b})$NHR$^{1c}$; $R^{1b}$ is tert-butyl; and $R^{1c}$ is —H.

In some embodiments of formula (Ib), $R^{1a}$ is —C(O)CH$(R^{1b})$NHR$^{1c}$ and $R^{1b}$ and $R^{1c}$, together with the atom to which they are attached, form a 5-membered ring.

In one embodiment, disclosed is a compound of formula (II), or a pharmaceutically acceptable salt thereof:

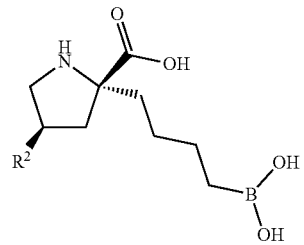

(II)

wherein
$R^2$ is —OH or —NHR$^{2a}$;
$R^{2a}$ is —H or —C(O)CH$(R^{2b})$NH$_2$; and
$R^{2b}$ is —CH$_3$ or —CH(CH$_3$)$_2$.

In one embodiment, disclosed is a compound of formula (II). In another embodiment, disclosed is a pharmaceutically acceptable salt of the compound of formula (II).

In some embodiments of formula (II), $R^2$ is —OH.

In some embodiments of formula (II), $R^2$ is —NHR$^2$a and $R^{2a}$ is —H.

In some embodiments of formula (II), $R^2$ is —NHR$^{2a}$, $R^{2a}$ is —C(O)CH$(R^{2b})$NH$_2$ and $R^{2b}$ is —CH$_3$.

In some embodiments of formula (II), $R^2$ is —$NHR^{2a}$, $R^{2a}$ is —$C(O)CH(R^{2b})NH_2$ and $R^{2b}$ is —$CH(CH_3)_2$.

In one embodiment, disclosed is a compound of formula (IIa), or a pharmaceutically acceptable salt thereof:

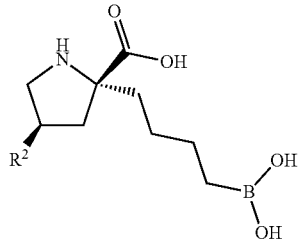

(IIa)

wherein
$R^2$ is —OH or —$NHR^{2a}$;
$R^{2a}$ is —H or —$C(O)CH(R^{2b})NHR^{2c}$;
$R^{2b}$ is selected from —H, —$(C_1-C_4)$ alkyl and $CH_2OR^{2d}$; and $R^{2c}$ is —H; or
$R^{2b}$ and $R^{2c}$, together with the atoms to which they are attached, form a 5-membered heterocyclic ring; and
$R^{2d}$ is H or —$CH_3$.

In one embodiment, disclosed is a compound of formula (IIa). In another embodiment, disclosed is a pharmaceutically acceptable salt of the compound of formula (IIa).

In one embodiment of formula (IIa), $R^2$ is —OH.

In one embodiment of formula (IIa), $R^2$ is —$NHR^{2a}$; and $R^{2a}$ is —H.

In one embodiment of formula (IIa), $R^2$ is —$NHR^{2a}$; and $R^{2a}$ is —$C(O)CH(R^{2b})NHR^{2c}$; $R^{2b}$ is H and $R^{2b}$ is H.

In one embodiment of formula (IIa), $R^2$ is —$NHR^{2a}$; and $R^{2a}$ is —$C(O)CH(R^{2b})NHR^{2c}$; $R^{2b}$ is —$CH_2OR^{2d}$; $R^{2b}$ is H and $R^{2d}$ is H.

In one embodiment of formula (IIa), $R^2$ is —$NHR^{2a}$; and $R^{2a}$ is —$C(O)CH(R^{2b})NHR^{2c}$; $R^{2b}$ is —$CH_2OR^{2d}$; $R^{2b}$ is H and $R^{2d}$ is —$CH_3$.

In some embodiments of formula (IIa), $R^2$ is —$NHR^{2a}$; $R^{2a}$ is —$C(O)CH(R^{2b})NHR^{2c}$; $R^{2b}$ is —$(C_1-C_4)$ alkyl and $R^{2b}$ is —H. In some embodiments, the $C_1-C_4$ alkyl is selected from methyl, ethyl, isopropyl, sec-butyl, tert-butyl, and isobutyl.

In some embodiments of formula (IIa), $R^2$ is —$NHR^{2a}$; $R^{2a}$ is —$C(O)CH(R^{2b})NHR^{2c}$; $R^{2b}$ is methyl; and $R^{2c}$ is —H.

In some embodiments of formula (IIa), $R^2$ is —$NHR^{2a}$; $R^{2a}$ is —$C(O)CH(R^{2b})NHR^{2c}$; $R^{2b}$ is ethyl; and $R^{2c}$ is —H.

In some embodiments of formula (IIa), $R^2$ is —$NHR^{2a}$; $R^{2a}$ is —$C(O)CH(R^{2b})NHR^{2c}$; $R^{2b}$ is isopropyl; and $R^{2c}$ is —H.

In some embodiments of formula (IIa), $R^2$ is —$NHR^{2a}$, $R^{2a}$ is —$C(O)CH(R^{2b})NHR^{2c}$; $R^{2b}$ is sec-butyl; and $R^{2c}$ is —H.

In some embodiments of formula (IIa), $R^2$ is —$NHR^{2a}$; $R^{2a}$ is —$C(O)CH(R^{2b})NHR^{2c}$; $R^{2b}$ is isobutyl; and $R^{2c}$ is —H.

In some embodiments of formula (IIa), $R^2$ is —$NHR^{2a}$; $R^{2a}$ is —$C(O)CH(R^{2b})NHR^{2c}$; $R^{2b}$ is tert-butyl; and $R^{2c}$ is —H.

In some embodiments of formula (IIa), $R^2$ is —$NHR^{2a}$; $R^{2a}$ is —$C(O)CH(R^{2b})NHR^{2c}$ and $R^{2b}$ and $R^{2c}$, together with the atom to which they are attached, form a 5-membered ring.

In one embodiment, disclosed is a compound of formula (IIb), or a pharmaceutically acceptable salt thereof:

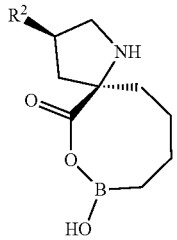

(IIb)

wherein
$R^2$ is —OH or —$NHR^{2a}$;
$R^{2a}$ is —H or —$C(O)CH(R^{2b})NHR^{2c}$;
$R^{2b}$ is selected from —H, —$(C_1-C_4)$ alkyl and $CH_2OR^{2d}$; and $R^{2c}$ is —H; or
$R^{2b}$ and $R^{2c}$, together with the atoms to which they are attached, form a 5-membered heterocyclic ring; and
$R^{2d}$ is —H or —$CH_3$.

In one embodiment, disclosed is a compound of formula (IIb). In another embodiment, disclosed is a pharmaceutically acceptable salt of the compound of formula (IIb).

In one embodiment of formula (IIb), $R^2$ is —OH.

In one embodiment formula (IIb), $R^2$ is —$NHR^{2a}$; and $R^{2a}$ is —H.

In one embodiment formula (IIb), $R^2$ is —$NHR^{2a}$; and $R^{2a}$ is —$C(O)CH(R^{2b})NHR^{2c}$; $R^{2b}$ is H and $R^{2b}$ is H.

In one embodiment formula (IIb), $R^2$ is —$NHR^{2a}$; and $R^a$ is —$C(O)CH(R^{2b})NHR^{2c}$; $R^{2b}$ is —$CH_2OR^{2d}$; $R^{2b}$ is H and $R^{2d}$ is H.

In one embodiment formula (IIb), $R^2$ is —$NHR^{2a}$; and $R^{2a}$ is —$C(O)CH(R^{2b})NHR^{2c}$; $R^{2b}$ is —$CH_2OR^{2d}$; $R^{2b}$ is H and $R^{2d}$ is —$CH_3$.

In some embodiments formula (IIb), $R^2$ is —$NHR^{2a}$; $R^{2a}$ is —$C(O)CH(R^{2b})NHR^{2c}$; $R^{2b}$ is —$(C_1-C_4)$ alkyl and $R^{2b}$ is —H. In some embodiments, the $C_1-C_4$ alkyl is selected from methyl, ethyl, isopropyl, sec-butyl, tert-butyl, and isobutyl.

In some embodiments formula (IIb), $R^2$ is —$NHR^{2a}$; $R^{2a}$ is —$C(O)CH(R^{2b})NHR^{2c}$; $R^{2b}$ is methyl; and $R^{2c}$ is —H.

In some embodiments formula (IIb), $R^2$ is —$NHR^{2a}$; $R^{2a}$ is —$C(O)CH(R^{2b})NHR^{2c}$; $R^{2b}$ is ethyl; and $R^{2c}$ is —H.

In some embodiments formula (IIb), $R^2$ is —$NHR^{2a}$; $R^{2a}$ is —$C(O)CH(R^{2b})NHR^{2c}$; $R^{2b}$ is isopropyl; and $R^{2c}$ is —H.

In some embodiments formula (IIb), $R^2$ is —$NHR^{2a}$, $R^{2a}$ is —$C(O)CH(R^{2b})NHR^{2c}$; $R^{2b}$ is sec-butyl; and $R^{2b}$ is —H.

In some embodiments formula (IIb), $R^2$ is —$NHR^{2a}$; $R^{2a}$ is —$C(O)CH(R^{2b})NHR^{2c}$; $R^{2b}$ is isobutyl; and $R^{2c}$ is —H.

In some embodiments formula (IIb), $R^2$ is —$NHR^{2a}$; $R^{2a}$ is —$C(O)CH(R^{2b})NHR^{2c}$; $R^{2b}$ is tert-butyl; and $R^{2c}$ is —H.

In some embodiments formula (IIb), $R^2$ is —$NHR^{2a}$; $R^{2a}$ is —$C(O)CH(R^{2b})NHR^{2c}$ and $R^{2b}$ and $R^{2c}$, together with the atom to which they are attached, form a 5-membered ring.

In some embodiments, disclosed is a compound of formula (III), or a pharmaceutically acceptable salt thereof:

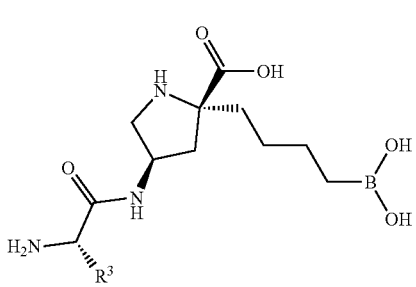

(III)

wherein $R^3$ is —CH$_3$ or —CH(CH$_3$)$_2$.

In one embodiment, disclosed is a compound of formula (III). In another embodiment, disclosed is a pharmaceutically acceptable salt of the compound of formula (III).

In some embodiments of formula (III), $R^3$ is —CH$_3$.

In some embodiments of formula (III), $R^3$ is —CH(CH$_3$)$_2$.

In some embodiments, disclosed is a compound of formula (IIIa), or a pharmaceutically acceptable salt thereof:

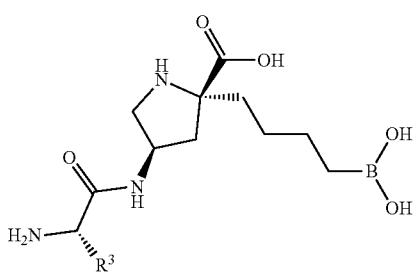

(IIIa)

wherein $R^3$ is selected from —H, —(C$_1$-C$_4$) alkyl and CH$_2$OR$^{3a}$; and $R^{3a}$ is —H or —CH$_3$.

In one embodiment, disclosed is a compound of formula (IIIa). In another embodiment, disclosed is a pharmaceutically acceptable salt of the compound of formula (IIIa).

In one embodiment of formula (IIIa), $R^3$ is —H.

In one embodiment formula (IIIa), $R^3$ is —CH$_2$OR$^3$a and $R^{3a}$ is —H.

In one embodiment formula (IIIa), $R^3$ is —CH$_2$OR$^{3a}$ and $R^{3a}$ is —CH$_3$.

In one embodiment formula (IIIa), $R^3$ is —(C$_1$-C$_4$) alkyl. In some embodiments, the (C$_1$-C$_4$) alkyl is selected from methyl, ethyl, isopropyl, sec-butyl and isobutyl.

In one embodiment formula (IIIa), $R^3$ is methyl.

In one embodiment formula (IIIa), $R^3$ is ethyl.

In one embodiment formula (IIIa), $R^3$ is isopropyl.

In one embodiment formula (IIIa), $R^3$ is sec-butyl.

In one embodiment formula (IIIa), $R^3$ is isobutyl.

In one embodiment formula (IIIa), $R^3$ is tert-butyl.

In some embodiments, disclosed is a compound of formula (IIIb), or a pharmaceutically acceptable salt thereof:

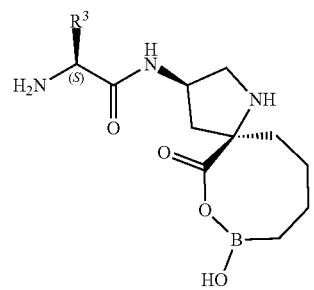

(IIIb)

wherein $R^3$ is selected from —H, —(C$_1$-C$_4$) alkyl and —CH$_2$OR$^{3a}$; and $R^{3a}$ is —H or —CH$_3$.

In one embodiment, disclosed is a compound of formula (IIIb). In another embodiment, disclosed is a pharmaceutically acceptable salt of the compound of formula (IIIb).

In one embodiment formula (IIIb), $R^3$ is —H.

In one embodiment formula (IIIb), $R^3$ is —CH$_2$OR$^3$a and $R^{3a}$ is —H.

In one embodiment formula (IIIb), $R^3$ is —CH$_2$OR$^3$a and $R^{3a}$ is —CH$_3$.

In one embodiment formula (IIIb), $R^3$ is —(C$_1$-C$_4$) alkyl. In some embodiments, the (C$_1$-C$_4$) alkyl is selected from methyl, ethyl, isopropyl, sec-butyl and isobutyl.

In one embodiment formula (IIIb), $R^3$ is methyl.

In one embodiment formula (IIIb), $R^3$ is ethyl.

In one embodiment formula (IIIb), $R^3$ is isopropyl.

In one embodiment formula (IIIb), $R^3$ is sec-butyl.

In one embodiment formula (IIIb), $R^3$ is isobutyl.

In one embodiment formula (IIIb), $R^3$ is tert-butyl.

In some embodiments, disclosed is a compound of formula (IV), or a pharmaceutically acceptable salt thereof:

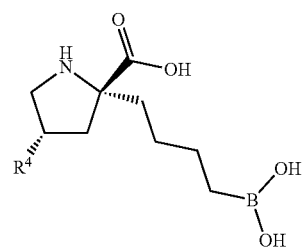

(IV)

wherein $R^4$ is —OH or —NH$_2$.

In one embodiment, disclosed is a compound of formula (IV). In another embodiment, disclosed is a pharmaceutically acceptable salt of the compound of formula (IV).

In some embodiments formula (IV), $R^4$ is —OH.

In some embodiments formula (IV), $R^4$ is —NH$_2$.

In some embodiments, disclosed is a compound of formula (IVb), or a pharmaceutically acceptable salt thereof:

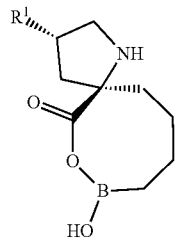

(IVb)

wherein R⁴ is —OH or —NH₂.

In one embodiment, disclosed is a compound of formula (IVb). In another embodiment, disclosed is a pharmaceutically acceptable salt of the compound of formula (IVb).

In some embodiments formula (IVb), R⁴ is —OH.

In some embodiments formula (IVb), R⁴ is —NH₂.

In some embodiments, disclosed is a compound of formula (V), or a pharmaceutically acceptable salt thereof:

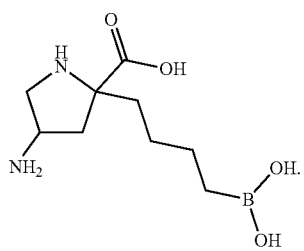

(V)

In one embodiment, disclosed is a compound of formula (V). In another embodiment, disclosed is a pharmaceutically acceptable salt of the compound of formula (V).

In some embodiments, disclosed is a compound of formula (Vb), or a pharmaceutically acceptable salt thereof:

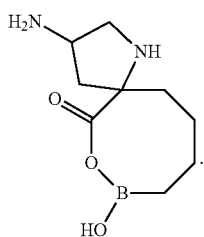

(Vb)

In one embodiment, disclosed is a compound of formula (Vb). In another embodiment, disclosed is a pharmaceutically acceptable salt of the compound of formula (Vb).

In some embodiments, disclosed is a compound of formula (VI), or a pharmaceutically acceptable salt thereof:

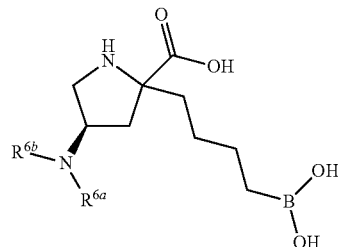

(VI)

wherein
$R^{6a}$ is —H or —CH₃;
$R^{6b}$ is —C(O)C($R^{6c}R^{6d}$)NH₂; or —(C₁-C₃) alkyl which is substituted with 0 or 1 amino or —$OR^{6e}$; and
$R^{6c}$ is —(C₁-C₃) alkyl which is substituted with 0 or 1 amino or —$OR^{6f}$;
$R^{6d}$ is H or —CH₃; and
$R^{6e}$ and $R^{6f}$ are independently —H or —CH₃.

In one embodiment, disclosed is a compound of formula (VI). In another embodiment, disclosed is a pharmaceutically acceptable salt of the compound of formula (VI).

In some embodiments of formula (VI), $R^{6a}$ is —H or —CH₃; and $R^{6b}$ is —(C₁-C₃) alkyl which is substituted with 0 or 1 amino.

In some embodiments of formula (VI), $R^{6a}$ is —H or —CH₃; $R^{6b}$ is —C(O)C($R^{6c}R^{6d}$)NH₂; $R^{6c}$ is —(C₁-C₃) alkyl which is substituted with 0 or 1 amino or —OH; and $R^{6d}$ is H or —CH₃.

In some embodiments, a compound of formula (VI) is represented by formula (VIa1) or (VIa2):

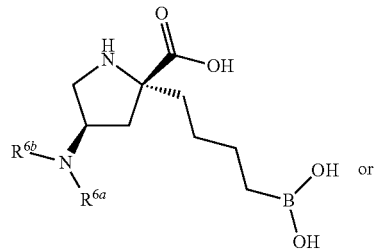

(VIa1)

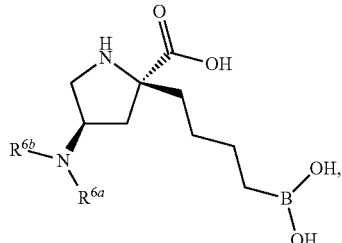

(VIa2)

wherein $R^{6a}$ and $R^{6b}$ are the same as defined above.

In one embodiment, disclosed is a compound of formula (VIa1). In another embodiment, disclosed is a pharmaceutically acceptable salt of the compound of formula (VIa1).

In one embodiment, disclosed is a compound of formula (VIa2). In another embodiment, disclosed is a pharmaceutically acceptable salt of the compound of formula (VIa2).

In one embodiment of Formula (VI), $R^{6b}$ is —CH₃ or —CH₂CH₂NH₂.

In some embodiments, disclosed is a compound of formula (VIb), or a pharmaceutically acceptable salt thereof:

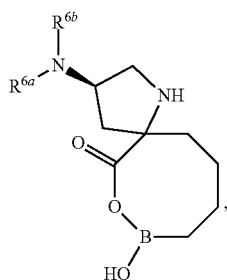

(VIb)

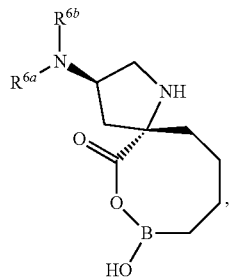

(VIb2)

wherein $R^{6a}$ and $R^{6b}$ are the same as defined above.

wherein
$R^{6a}$ is —H or —CH$_3$;
$R^{6b}$ is —C(O)C($R^{6c}R^{6d}$)NH$_2$; or —(C$_1$-C$_3$) alkyl which is substituted with 0 or 1 amino or —OR$^{6e}$; and
$R^{6c}$ is —(C$_1$-C$_3$) alkyl which is substituted with 0 or 1 amino or —OR$^{6f}$;
$R^{6d}$ is H or —CH$_3$; and
$R^{6e}$ and $R^{6f}$ are independently —H or —CH$_3$.

In one embodiment, disclosed is a compound of formula (VIb). In another embodiment, disclosed is a pharmaceutically acceptable salt of the compound of formula (VIb).

In one embodiment of formula (VIb), $R^{6b}$ is —CH$_3$ or —CH$_2$CH$_2$NH$_2$.

In some embodiments of formula (VIb), $R^{6a}$ is —H or —CH$_3$; and $R^{6b}$ is —(C$_1$-C$_3$) alkyl which is substituted with 0 or 1 amino.

In some embodiments of formula (VIb), $R^{6a}$ is —H or —CH$_3$; $R^{6b}$ is —C(O)C($R^{6c}R^{6d}$)NH$_2$; $R^{6c}$ is —(C$_1$-C$_3$) alkyl which is substituted with 0 or 1 amino or —OH; and $R^{6d}$ is H or —CH$_3$.

In some embodiments, a compound of formula (VIb) is represented by formula (VIb1) or (VIb2):

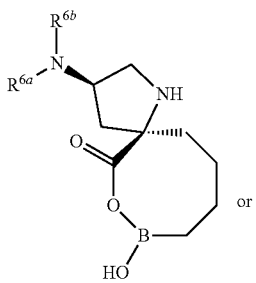

(VIb1)

In some embodiments, the compounds of formula (I), (Ia), (II), (IIa), (III), (IIIa), (IV), (V), and (VI) including species thereof are converted to the compounds of formula (Ib), (IIb), (IIIb), (IVb), (Vb), and (VIb) including species thereof via intramolecular cyclization, and vice versa. That is, it is an interconversion process. The compounds of formula (I), (Ia), (II), (IIa), (III), (IIIa), (IV), (V), and (VI) including species thereof and the compounds of formula (Ib), (IIb), (IIIb), (IVb), (Vb), and (VIb) including species thereof are each converted into the other partially or completely depending on the conditions, such as temperature, pressure, humidity, the pH and/or composition of medium (e.g., solvents), and etc. It is illustrated in the scheme below:

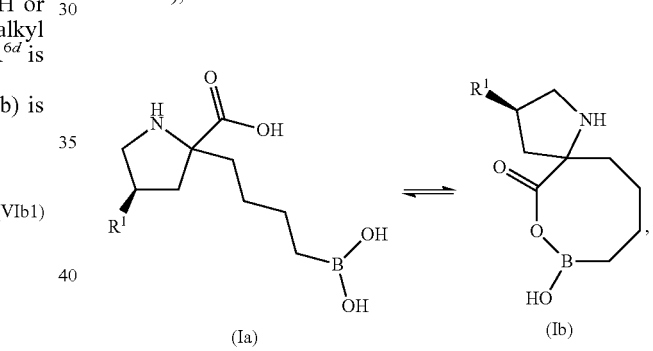

wherein $R^1$ is the same as defined in formula (Ia) and (Ib) above.

In some embodiments, disclosed are compounds of Table 1, or a pharmaceutically salt thereof:

TABLE 1

| Example | Compound | Name |
|---|---|---|
| 2 | 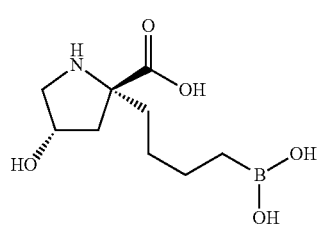 [SMILES: O=C(O)[C@@]1(CCCCB(O)O)C[C@H](O)CN1] | (2R,4S)-2-(4-boronobutyl)-4-hydroxypyrrolidine-2-carboxylic acid |

TABLE 1-continued

| Example | Compound | Name |
|---|---|---|
| 3 | | (2R,4R)-2-(4-boronobutyl)-4-hydroxypyrrolidine-2-carboxylic acid |
| 4 | | (2S,4S)-4-amino-2-(4-boronobutyl)pyrrolidine-2-carboxylic acid |
| 5 | | (2R,4S)-4-amino-2-(4-boronobutyl)pyrrolidine-2-carboxylic acid |
| 6 | | (2S,4R)-4-amino-2-(4-boronobutyl)pyrrolidine-2-carboxylic acid |
| 7 | | (2R,4R)-4-amino-2-(4-boronobutyl)pyrrolidine-2-carboxylic acid |
| 8 | | (2R,4R)-4-((S)-2-aminopropanamido)-2-(4-boronobutyl)pyrrolidine-2-carboxylic acid |
| 9 | | (2R,4R)-4-((S)-2-amino-3-methylbutanamido)-2-(4-boronobutyl)pyrrolidine-2-carboxylic acid |

TABLE 1-continued

| Example | Compound | Name |
|---|---|---|
| 10 | | (2R,4R)-4-((R)-2-amino-3-methylbutanamido)-2-(4-boronobutyl)pyrrolidine-2-carboxylic acid |
| 11 | | (2R,4R)-4-((S)-2-amino-3,3-dimethylbutanamido)-2-(4-boronobutyl)pyrrolidine-2-carboxylic acid |
| 12 | | (2R,4R)-2-(4-boronobutyl)-4-((S)-pyrrolidine-2-carboxamido)pyrrolidine-2-carboxylic acid |
| 13 | | (2R,4R)-4-(2-aminoacetamido)-2-(4-boronobutyl)pyrrolidine-2-carboxylic acid |
| 14 | | (2R,4R)-4-((S)-2-aminobutanamido)-2-(4-boronobutyl)pyrrolidine-2-carboxylic acid |

TABLE 1-continued

| Example | Compound | Name |
|---|---|---|
| 15 | | (2R,4R)-4-((2S,3S)-2-amino-3-methylpentanamido)-2-(4-boronobutyl)pyrrolidine-2-carboxylic acid |
| 16 | | (2R,4R)-4-[[(2S)-2-amino-4-methyl-pentanoyl]amino]-2-(4-boronobutyl)pyrrolidine-2-carboxylic acid |
| 17 | | (2R,4R)-4-[[(2S)-2-amino-3-hydroxy-propanoyl]amino]-2-(4-boronobutyl)pyrrolidine-2-carboxylic acid |
| 18 | | (2R,4R)-4-[[(2S)-2-amino-3-methoxy-propanoyl]amino]-2-(4-boronobutyl)pyrrolidine-2-carboxylic acid |
| 19 | | (S)-2-amino-N-((3R,5R)-8-hydroxy-6-oxo-7-oxa-1-aza-8-boraspiro[4.7]clodecan-3-yl)-3-methylbutanamide |

TABLE 1-continued

| Example | Compound | Name |
|---|---|---|
| 20 | | (2R,4R)-4-[[(2S)-2-amino-3-hydroxy-3-methyl-butanoyl]amino]-2-(4-boronobutyl)pyrrolidine-2-carboxylic acid |
| 21 | | (2R,4R)-4-[(2S)-2-amino-2,3-dimethyl-butanoyl]amino]-2-(4-boronobutyl)pyrrolidine-2-carboxylic acid |
| 22 | | (2R,4R)-2-(4-boronobutyl)-4-[[(2S)-2,3-diaminopropanoyl]amino]pyrrolidine-2-carboxylic acid |
| 23 | | (2R,4R)-2-(4-boronobutyl)-4-(methylamino)pyrrolidine-2-carboxylic acid |
| 24 | | (2S,4R)-2-(4-boronobutyl)-4-(methylamino)pyrrolidine-2-carboxylic acid |

TABLE 1-continued

| Example | Compound | Name |
|---|---|---|
| 25 | | (2R,4R)-2-(4-boronobutyl)-4-(dimethylamino)pyrrolidine-2-carboxylic acid |
| 26 | | (2S,4R)-2-(4-boronobutyl)-4-(dimethylamino)pyrrolidine-2-carboxylic acid |
| 27 | | (2R,4R)-4-(2-aminoethylamino)-2-(4-boronobutyl)pyrrolidine-2-carboxylic acid |
| 28 | | (2S,4R)-4-(2-aminoethylamino)-2-(4-boronobutyl)pyrrolidine-2-carboxylic acid |
| 29 | | (2R,4R)-4-[[(2S)-2-amino-3-methyl-butanoyl]-methyl-amino]-2-(4-boronobutyl)pyrrolidine-2-carboxylic acid |

TABLE 1-continued

| Example | Compound | Name |
|---|---|---|
| 30 | | (2S,4R)-4-[[(2S)-2-amino-3-methyl-butanoyl]-methyl-amino]-2-(4-boronobutyl)pyrrolidine-2-carboxylic acid |

The language "$C_1$-$C_4$ alkyl" includes acyclic alkyl moieties having 1-4 carbon atoms. Examples of $C_1$-$C_4$ alkyl moieties include methyl, ethyl, n-propyl, isopropyl, n-butyl, sec-butyl, isobutyl, and tert-butyl.

The language "pharmaceutically acceptable salt" includes acid addition or base addition salts that retain the biological effectiveness and properties of the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 and, which typically are not biologically or otherwise undesirable. In many cases, the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 are capable of forming acid and/or base salts by virtue of the presence of basic and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, sulfate/hydrogensulfate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonia and salts of ammonium and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 can be synthesized from a basic or acidic moiety, by conventional chemical methods. Generally, such salts can be prepared by reacting free acid forms of these compounds with a stoichiometric amount of the appropriate base (such as Nat, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "J. Pharm. Sci., 1977, 66, 1-19 and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1. Isotopically labeled compounds have structures depicted by the formulas given herein except that one or more atoms are replaced by an atom of the same element but with differing mass number. Examples of isotopes that can be incorporated into the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 and their pharmaceutically acceptable salts include isotopes of hydrogen, carbon, nitrogen, oxygen, phosphorous, sulfur, fluorine, chlorine and iodine, such as $^2H$, $^3H$, $^{11}C$, $^{13}C$, $^{14}C$, $^{15}N$, $^{35}S$, $^{36}Cl$ and $^{125}I$. Isotopically labeled compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 can generally be prepared by conventional techniques known to those skilled in the art or by processes analogous to those described in the accompanying Examples using appropriate isotopically labeled reagents in place of the non-labeled reagents previously employed.

The compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 may have different isomeric forms. The language "optical isomer," "stereoisomer" or "diastereoisomer" refers to any of the various stereoisomeric configurations which may exist for a given compound of formula (I), (Ia), (Ib), (II), (IIa), (IIb), (III), (IIIa), (IIIb), (IV), (IVb), (V), (Vb), (VI), (VIb), including any subgenera or species thereof, and Table 1. It is understood that a substituent may be attached at a chiral center of a carbon atom and, therefore, the disclosed compounds include enantiomers, diastereomers and racemates. The term "enantiomer" includes pairs of stereoisomers that are non-superimposable mirror images of each other. A 1:1 mixture of a pair of enantiomers is a racemic mixture. The term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R-S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1 contain one or more asymmetric centers or axes and may thus give rise to enantiomers, diastereomers or other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques well known in the art, such as chiral HPLC.

Also disclosed herein the Intermediates 1-48 in the Examples, and salts thereof.

Pharmaceutical Compositions

In some embodiments, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, and a pharmaceutically acceptable carrier.

The language "pharmaceutically acceptable carrier" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The amount of active ingredient that is combined with one or more pharmaceutically acceptable carriers to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Therapeutic Utilities

The present compounds are useful as arginase inhibitors in therapies.

In one aspect, disclosed are methods for treating cancer in a subject in need thereof, comprising administering to the subject an effective amount of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof.

In one aspect, disclosed are methods for treating a respiratory inflammatory disease in a subject in need thereof, comprising administering to the subject an effective amount of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof.

In one aspect, disclosed is a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating cancer.

In one aspect, disclosed is a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating a respiratory inflammatory disease.

In one aspect, disclosed is the use of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt, in the manufacture of a medicament for treating cancer.

In one aspect, disclosed is the use of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt, in the manufacture of a medicament for treating a respiratory inflammatory disease.

In one aspect, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating cancer.

In one aspect, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in treating a respiratory inflammatory disease.

The term "cancer" includes, for example, renal cell carcinoma, head and neck squamous cell carcinoma, lung cancer (e.g., small cell lung cancer (SCLC), non-small cell lung cancer (NSCLC), mesothelioma), pancreatic cancer, colorectal cancer, breast cancer, acute myeloid leukemia (AML), prostate cancer, gastric cancer, bladder cancer, melanoma, renal cancer and ovarian cancer. In some embodiments, the cancer has metastasized. In some embodiments, the cancer is associated with Arginase 1 and/or Arginase 2 modulation.

In some embodiments, the cancer is associated with increased plasma Arginase 1 levels. In some embodiments, the cancer is associated with decreased plasma arginine levels. In some embodiments, the cancer is associated with both increased plasma Arginase 1 levels and decreased plasma arginine levels. In some embodiments, the cancer associated with increased plasma Arginase 1 levels and/or decreased plasma arginine levels includes renal cell carcinoma, head and neck squamous cell carcinoma, lung cancer (e.g., small cell lung cancer (SCLC), non-small cell lung cancer (NSCLC), mesothelioma), pancreatic cancer, colorectal cancer and breast cancer.

In some embodiments, the cancer secretes Arginase 2, for example, acute myeloid leukemia and prostate cancer.

In some embodiments, the cancer is associated with Arginase 1 positive tumor infiltrating immune cells, for example, lung cancer (small cell lung cancer (SCLC), non-small cell lung cancer (NSCLC), gastric cancer, bladder cancer, colorectal cancer, melanoma, head and neck squamous cell carcinoma, breast cancer, prostate cancer, ovarian cancer, pancreatic cancer and renal cancer.

The term "a respiratory inflammatory disease" refers to inflammatory conditions or disorders that affect the airspaces, pulmonary vasculature, pulmonary interstitium, or a combination thereof. They can be isolated to the lung or involve multiple organs. In one embodiment, the respiratory inflammatory disease is an inflammatory lung disease. In another embodiment, the inflammatory lung disease is non-infectious.

In some embodiments, the respiratory inflammatory disease is asthma, chronic obstructive pulmonary disease (COPD), chemically-induced lung fibrosis, idiopathic pulmonary fibrosis, cystic fibrosis, or a combination thereof. In some embodiments, the respiratory inflammatory disease is chronic obstructive pulmonary disease (COPD) or asthma.

In one aspect, disclosed are methods for inhibiting arginase in a subject in need thereof, comprising administering to the subject an effective amount of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof.

In one aspect, disclosed is a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in inhibiting arginase.

In one aspect, disclosed is the use of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, in the manufacture of a medicament for inhibiting arginase.

In one aspect, disclosed are pharmaceutical compositions comprising a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, or a pharmaceutically acceptable salt thereof, for use in inhibiting arginase.

The term "arginase" includes manganese-containing enzymes belonging to the uerohydrolase family that catalyze the fifth and final step in the urea cycle converting L-arginine into L-ornithine and urea. The term "arginase" includes the two isozymes of the enzyme, e.g., Arginase 1, which functions in the urea cycle, and is located primarily in the cytoplasm of the liver, and Arginase 2, which is located in the mitochondria of several tissues in the body and is implicated in the regulation of arginine/ornithine concentrations in the cell. In some embodiments, the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1, or a pharmaceutically acceptable salt thereof, are selective for arginase 1. In some embodiments, the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1, or a pharmaceutically acceptable salt thereof, are selective for Arginase 2. In some embodiments, the compounds of formula (I), (Ia), (Ib), (II), (IIa), (IIb), (III), (IIIa), (IIIb), (IV), (IVb), (V), (Vb), (VI), (VIb), including any subgenera or species thereof, and Table 1, or a pharmaceutically acceptable salt thereof, are inhibit both Arginase 1 and Arginase 2.

The language "effective amount" includes an amount of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1 that will elicit a biological or medical response in a subject, for example, the reduction or inhibition of enzyme or protein activity related to arginase or cancer, amelioration of symptoms of cancer or the slowing or delaying of progression of cancer. In some embodiments, the language "effective amount" includes the amount of a compound of formula (I), (Ia), (Ib), (II), (IIa), (IIb), (III), (IIIa), (IIIb), (IV), (IVb), (V), (Vb), (VI), (VIb), including any subgenera or species thereof, or Table 1, that when administered to a subject, is effective to at least partially alleviate, inhibit, and/or ameliorate cancer or inhibit arginase, and/or reduce or inhibit the growth of a tumor or proliferation of cancerous cells in a subject.

The term "subject" includes warm blooded mammals, for example, primates, dogs, cats, rabbits, rats, and mice. In some embodiments, the subject is a primate, for example, a human. In some embodiments, the subject is suffering from cancer. In some embodiments, the subject is in need of treatment (e.g., the subject would benefit biologically or medically from treatment). In some embodiments, the patient is suffering from cancer. In some embodiments, the subject has increased plasma Arginase 1 levels. In some embodiments, the subject has decreased arginine levels. In some embodiments, the patient has both increased plasma Arginase 1 levels and decreased arginine levels. In some embodiments, the subject has a cancer secreting Arginase 2 (e.g., acute myeloid leukemia or prostate cancer). In some embodiments, the subject has Arginase 1 positive tumor infiltrating immune cells.

The language "inhibit," "inhibition" or "inhibiting" includes a decrease in the baseline activity of a biological activity or process. In some embodiments, the compounds of formula formula (I), (Ia), (Ib), (II), (IIa), (IIb), (III), (IIIa), (IIIb), (IV), (IVb), (V), (Vb), (VI), (VIb), including any subgenera or species thereof, and Table 1 inhibit arginase.

The language "treat," "treating" and "treatment" includes the reduction or inhibition of enzyme or protein activity related to arginase or in a subject, amelioration of one or more symptoms of a cancer, or the slowing or delaying of progression of cancer in a subject. The language "treat," "treating" and "treatment" also includes the reduction or inhibition of the growth of a tumor or proliferation of cancerous cells in a subject.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless Stated Otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlashe Rf or Teledyne Isco CombiFlashe Companion® using prepacked RediSep Rf Gold™ Silica Columns (20-40 µm, spherical particles), GraceResolv™ Cartridges (Davisile silica) or Silicycle cartridges (40-63 µm).

(iv) preparative chromatography was performed on a Gilson prep HPLC instrument with UV collection; alternatively, preparative chromatography was performed on a Waters AutoPurification HPLC-MS instrument with MS- and UV-triggered collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection; alternatively, chiral preparative chromatography was performed on a Waters Prep 100 SFC-MS instrument with MS- and UV-triggered collection or a Thar MultiGram III SFC instrument with UV collection.

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance III 600 (600 MHz), Bruker Avance 400 (400 MHz), Bruker Avance 300 (300 MHz) or Bruker DRX 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal.

(viii) in general, end-products of the Formula I were also characterized by mass spectroscopy following liquid chromatography (LCMS or UPLC); UPLC was carried out using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 µm, 2.1×50 mm), for basic analysis the column used was a Waters Acquity BEH C18 (1.7 µm 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 mins (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 µm, 2.1×30 mm), for basic analysis the column used was a Waters Acquity BEH C18 (1.7 µm, 2.1×30 mm); LCMS was carried out using a Waters Alliance HT (2795) fitted with a Waters ZQ ESCi mass spectrometer and a Phenomenex GeminiNX C18 (5 µm, 110 A, 2.1×50 mm column at a flow rate of 1.1 mL/min 95% A to 95% B over 4 min with a 0.5 min hold where A=0.1% formic acid and B=0.1% formic acid in acetonitrile (for acidic work) or A=0.1% ammonium hydroxide in water and B=acetonitrile (for basic work). Additionally, LCMS was carried out using a Shimadzu UFLC fitted with a Shimadzu LCMS-2020 mass spectrometer and a Waters HSS C18 (1.8 µm, 2.1×50 mm) or Shim-pack XR-ODS (2.2 µm, 3.0×50 mm) or Phenomenex GeminiNX C18 (3 µm, 3.0×50 mm) column at a flow rate of 0.7 mL/min (for Waters HSS C18 column), 1.0 mL/min (for Shim-pack XR-ODS column) or 1.2 mL/min (for Phenomenex Gemini-NX C18), 95% A to 95% B over 2.2 min with a 0.6 min hold, where A=0.1% formic acid or 0.05% trifluoroacetic acid in water (for acidic work) or 0.1% ammonium hydroxide or 6.5 mM ammonium carbonate in water (for basic work) and B=acetonitrile. The reported molecular ion corresponds to the [M+H]+ unless otherwise specified; for molecules with multiple isotopic patterns (Br, Cl, etc.) the reported value is the one obtained for the lowest isotope mass unless otherwise specified.

(ix) ion exchange purification was generally performed using an SCX-2 (Biotage) cartridge.

(x) intermediate purity was assessed by thin layer chromatographic, mass spectroscopy, LCMS, UPLC/MS, HPLC (high performance liquid chromatography) and/or NMR analysis;

(xi) the following abbreviations have been used:—

EtOH: ethanol

EtOAc: ethyl acetate

LDA: lithium diisopropylamide

MeOH: methanol

TFA: trifluoroacetic acid

MeCN: acetonitrile

LCMS: liquid chromatography mass spectrometry rt or RT: room temperature aq: aqueous THF: tetrahydrofuran KHMDS: potassium bis(trimethylsilyl)amide DCM: dichloromethane DMF: dimethylformamide HATU: (1-[Bis(dimethylamino)methylene]-1H-1,2,3-triazolo[4,5-b]pyridinium 3-oxid hexafluorophosphate)

BOC: tert-butoxycarbonyl

DTNB: 5,5'-dithiobis(2-nitrobenzoic acid

TNB: 2-nitro-5-thiobenzoic acid

HEPES: (4-(2-hydroxyethyl)-1-piperazineethanesulfonic acid)

Example 1: (R)-2-(4-boronobutyl)pyrrolidine-2-carboxylic acid

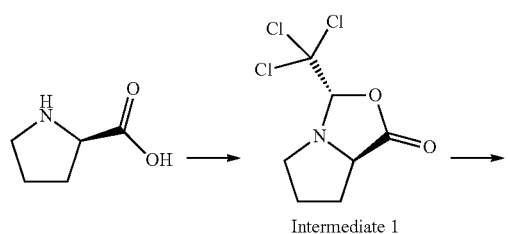

Intermediate 1

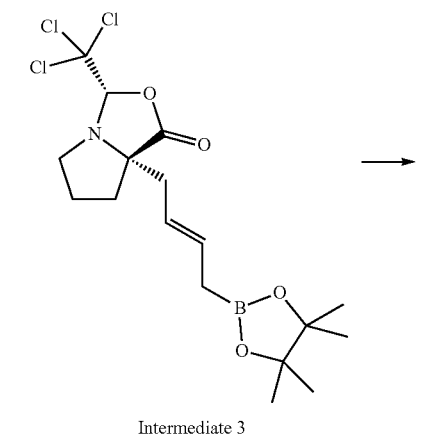

Intermediate 2

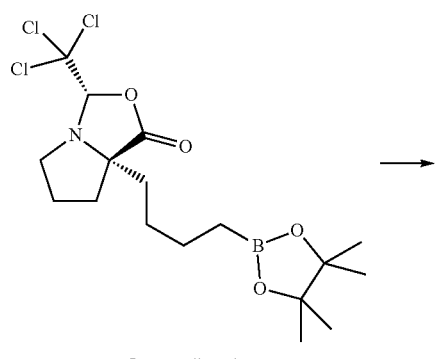

Intermediate 3

Intermediate 4

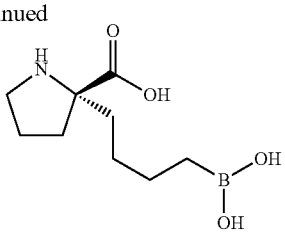

Example 1

Intermediate 1: (3S,7aR)-3-(trichloromethyl)tetrahydropyrrolo[1,2-c]oxazol-1(3H)-one 2,2,2-trichloroethane-1,1-diol (2.155 g, 13.03 mmol) was added to a solution of D-proline (1.00 g, 8.69 mmol) in CHCl$_3$ (100 mL) under nitrogen. The reaction flask was equipped with a reverse Dean-Stark trap and the reaction mixture was heated to reflux with stirring for 48 h. The reaction mixture was, cooled to room temperature, diluted with DCM (100 mL), and washed sequentially with water (2×200 mL) and saturated brine (2×200 mL). The organic layer was dried over Na$_2$SO$_4$, filtered and evaporated to afford crude product. The crude material was purified by crystallisation from EtOH to give product (Intermediate 1, 1.13 g, 53.2% yield) as a white solid. $^1$H NMR (300 MHz, CDCl$_3$) δ 1.66-2.41 (4H, m), 3.05-3.20 (1H, m), 3.40-3.50 (1H, m), 4.10-4.20 (1H, m), 5.18 (1H, s).

Intermediate 2: (3S,7aS)-7a-((E)-4-bromobut-2-enyl)-3-(trichloromethyl)tetrahydropyrrolo[1,2-c]oxazol-1 (3H)-one A solution of LDA (2.0 M in THF/heptane/ethylbenzene, 2.05 mL, 4.09 mmol) was added dropwise to a solution of (3S,7aR)-3-(trichloromethyhtetrahydropyrrolo[1,2-c]oxazol-1(3H)-one (Intermediate 1, 1.00 g, 4.09 mmol) in THF (500 mL) at −78° C. under an atmosphere of nitrogen. The resulting solution was stirred at −78° C. for 20 minutes. (E)-1,4-dibromobut-2-ene (875 mg, 4.09 mmol) was added to the reaction mixture dropwise as a solution in THF (2 mL). The reaction mixture was stirred at −78° C. for 30 minutes and then warmed to room temperature with stirring for an additional 2 h. The reaction mixture was evaporated to dryness and the resulting residue was diluted in EtOAc (20 mL) and washed sequentially with water (2×20 mL) and saturated brine (2×20 mL). The organic layer was dried over Na$_2$SO$_4$, filtered and concentrated to dryness. The crude material was purified by silica gel chromatography (hexanes/EtOAc) to afford the product (Intermediate 2, 760 mg, 49% yield). $^1$H NMR (300 MHz, CDCl$_3$) δ 1.55-1.75 (1H, m), 1.85-2.25 (3H, m), 2.52-2.73 (2H, m), 3.14-3.32 (2H, m), 3.89-4.10 (2H, m), 5.01 (1H, s), 5.79-5.99 (2H, m); m/z (ES$^+$) [M+H]$^+$=378.

Intermediate 3: (3S,7aS)-7a-((E)-4-(4,4,5,5-tetramethyl-1,3,2-dioxaborolan-2-yl)but-2-enyl)-3-(trichloromethyl)tetrahydropyrrolo[1,2-c]oxazol-1 (3H)-one Pd$_2$(dba)$_3$ (85.0 mg, 0.0928 mmol) was added to a solution of (3S,7aS)-7a-((E)-4-bromobut-2-enyl)-3-(trichloromethyhtetrahydropyrrolo[1,2-c]oxazol-1(3H)-one (Intermediate 2, 700 mg, 1.85 mmol) and bis(pinacolato)diboron (942 mg, 3.71 mmol) in THF (30 mL) under an atmosphere of nitrogen. The resulting mixture was heated to 60° C. and stirred for 5 h. The reaction mixture was cooled to room temperature and concentrated to dryness. The resulting residue was diluted with EtOAc (50 mL) and washed sequentially with water and saturated brine. The organic layer was dried over Na$_2$SO$_4$, filtered and concentrated to dryness. The resulting crude material was purified by silica gel chromatography to afford the product (Intermediate 3, 510 mg, 65% yield). $^1$H NMR (300 MHz, CDCl$_3$) δ 1.28 (12H, s), 1.58-1.80 (2H, m), 1.83-2.12 (3H, m) 2.42-2.65 (1H, m), 3.20 (1H, dd), 3.47 (1H, q), 3.71 (1H, t), 3.90 (1H, t), 4.98 (1H, s), 5.38-5.53 (1H, m), 5.64-5.83 (1H, m); m/z (ES$^+$) [M+H]$^+$=424.

Intermediate 4: (3S,7aR)-7a-(4-(4,4,5,5-tetramethyl-1,3,2-dioxaborolan-2-yl)butyl)-3-(trichloromethyl)tetrahydropyrrolo[1,2-c]oxazol-1 (3H)-one Pd/C (10% wt, 125 mg, 0.12 mmol) was added to a solution of (3S,7aS)-7a-((E)-4-(4,4,5,5-tetramethyl-1,3,2-dioxaborolan-2-yl)but-2-enyl)-3-(trichloromethyl)tetrahydropyrrolo[1,2-c]oxazol-1(3H)-one (Intermediate 3, 500 mg, 1.18 mmol) in MeOH (5 mL). The reaction flask was equipped with a balloon of H$_2$ and the suspension stirred at room temperature for 30 min. The reaction mixture was filtered through diatomaceous earth and washed with MeOH. The filtrate was concentrated to dryness to afford crude product (Intermediate 4, 390 mg, 78% yield) which was used without further purification. m/z (ES$^+$) [M+H]$^+$=426.

Example 1: (R)-2-(4-boronobutyl)pyrrolidine-2-carboxylic acid

Concentrated aqueous HCl (1.00 mL, 12.0 mmol) was added to a solution of (3S,7aR)-7a-(4-(4,4,5,5-tetramethyl-1,3,2-dioxaborolan-2-yl)butyl)-3-(trichloromethyhtetrahydropyrrolo[1,2-c]oxazol-1(3H)-one (Intermediate 4, 300 mg, 0.703 mmol) and phenylboronic acid (172 mg, 1.41 mmol) in 1,4-dioxane (20 mL). The resulting solution was heated to 80° C. for 15 h. The reaction mixture was cooled to room temperature and concentrated to dryness. Crude material was purified by preparative LCMS (XBridge Prep C18 OBD column, 5µ silica, 19×150 mm, H$_2$O (w/ 0.05% TFA/MeCN). Pure fractions were collected and concentrated to dryness to afford (R)-2-(4-boronobutyl)pyrrolidine-2-carboxylic acid (Example 1, 85 mg, 37% yield) as a white solid. $^1$H NMR (400 MHz, D$_2$O) δ 0.63-0.74 (2H, m), 1.09-1.27 (2H, m), 1.27-1.37 (2H, m), 1.65-1.75 (1H, m), 1.77-2.08 (4H, m), 2.25-2.37 (1H, m), 3.21-3.37 (2H, m); m/z (ES+) [M+H]$^+$=216.

Example 2: (2R,4S)-2-(4-boronobutyl)-4-hydroxy-pyrrolidine-2-carboxylic acid

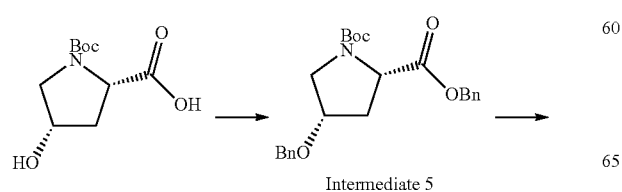

Intermediate 5

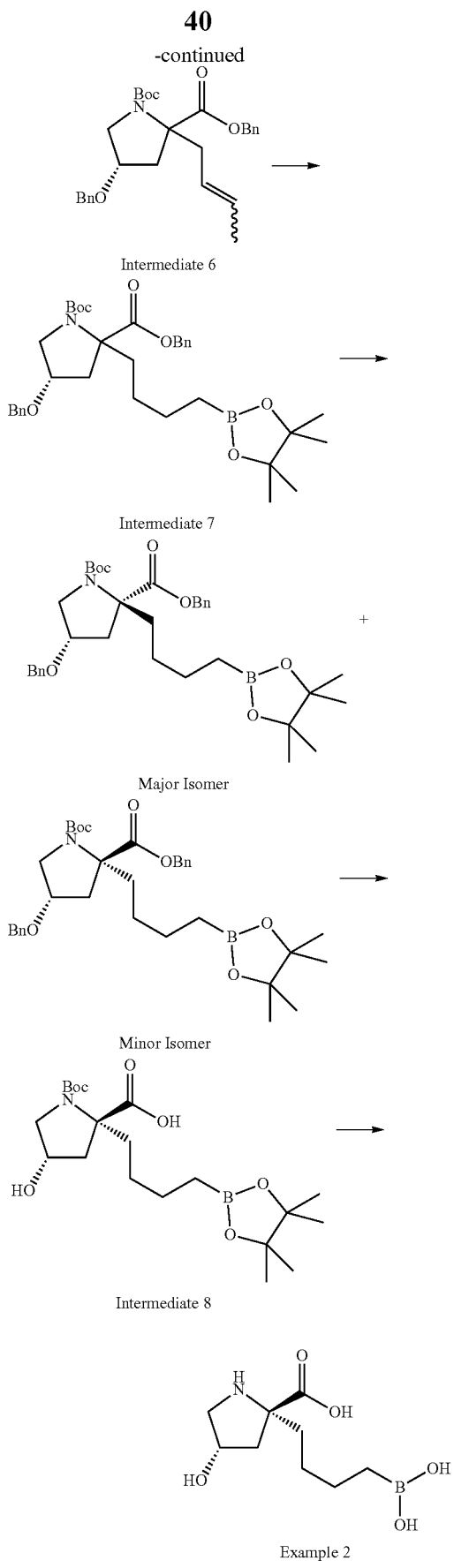

Intermediate 6

Intermediate 7

Major Isomer

Minor Isomer

Intermediate 8

Example 2

Intermediate 5: (2S,4S)-2-benzyl 1-tert-butyl 4-(benzyloxy)pyrrolidine-1,2-dicarboxylate (2S,4S)-1-(tert-butoxycarbonyl)-4-hydroxypyrrolidine-2-carboxylic acid (5.00 g, 21.6 mmol) was dissolved in DMF (73 mL) and the solution was cooled to 0° C. Sodium hydride (60% dispersion in mineral oil) (1.81 g, 45.3 mmol) was added portionwise and the suspension stirred at 0° C. for 1 h. Benzyl bromide (12.9 mL, 108 mmol) was added and the reaction mixture stirred overnight while slowly warming to RT. The crude reaction mixture was diluted with ethyl acetate (250 mL) and washed sequentially with citric acid (10% aq) and water. The organics were dried over $Na_2SO_4$, filtered and concentrated to dryness. The crude product was purified by silica gel chromatography (hexanes/EtOAc) to afford the product as a mixture of rotamers (Intermediate 5, 5.5 g, 62% yield). $^1$H NMR (300 MHz, DMSO-$d_6$) δ 1.28-1.40 (9H, s×2) rotamers, 2.20 (1H, dd), 2.36-2.45 (1H, m), 3.37 (1H, dd), 3.51-3.58 (1H, m), 4.14 (1H, br s), 4.33-4.50 (3H, m), 4.94-5.17 (2H, m), 7.25-7.32 (10H, m); m/z (ES$^+$) [M+H]$^+$=412.

Intermediate 6: (4S)-2-benzyl 1-tert-butyl 4-(benzyloxy)-2-(but-2-enyl)pyrrolidine-1,2-dicarboxylate (2S,4S)-2-Benzyl 1-tert-butyl 4-(benzyloxy)pyrrolidine-1,2-dicarboxylate (Intermediate 5, 2.75 g, 6.68 mmol) and crotyl bromide (1.03 mL, 10.0 mmol) were dissolved in THF (45 mL) and the solution was cooled to −78° C. under an atmosphere of $N_2$. The solution was treated with dropwise addition of a solution of KHMDS (0.5M in toluene, 20.1 mL, 10.0 mmol). The reaction mixture was slowly warmed to room temperature and stirred for 3 h. The crude reaction mixture was quenched with water and the volatiles were removed in vacuo. The crude mixture was diluted in DCM and the layers were separated. The organic layer was washed with water, dried over $Na_2SO_4$, filtered and concentrated to dryness. The crude material was purified by silica gel chromatography (hexanes/EtOAc) to afford the product as a mixture of rotamers and E/Z olefins (Intermediate 6, 2.54 g, 82% yield). $^1$H NMR (300 MHz, DMSO-$d_6$) δ 1.20-1.41 (9H, s×2) rotamers, 1.54-1.62 (3H, m), 2.10-2.59 (3H, m), 2.67-2.97 (1H, m), 3.10-3.43 (1H, m), 3.50-3.78 (1H, m), 3.98-4.15 (1H, m), 4.34-4.49 (2H, m), 4.94-5.13 (2H, m), 5.18-5.30 (1H, m), 5.38-5.63 (1H, m), 7.25-7.36 (10H, m); m/z (ES$^+$) [M+H]$^+$=466.

Intermediate 8: (2R,4S)-1-(tert-butoxycarbonyl)-4-hydroxy-2-(4-(4,4,5,5-tetramethyl-1,3,2-dioxaborolan-2-yl)butyl)pyrrolidine-2-carboxylic acid Bis(1,5-cyclooctadiene)diiridium(I) dichloride (0.366 g, 0.550 mmol) and bis(diphenylphosphino)methane (0.419 g, 1.09 mmol) were added to an oven-dried round-bottom flask. The flask was sealed and purged with $N_2$. The solids were dissolved in DCM (31 mL) and 4,4,5,5-tetramethyl-1,3,2-dioxaborolane (1.74 mL, 12.0 mmol) was added slowly to the solution. The reaction stirred at room temperature for 10 min. (4S)-2-Benzyl 1-tert-butyl 4-(benzyloxy)-2-(but-2-enyl)pyrrolidine-1,2-dicarboxylate (Intermediate 6, 2.54 g, 5.46 mmol) was added to the reaction as a solution in DCM (21 mL) and the reaction mixture stirred overnight. The reaction mixture was diluted with DCM and quenched with water. The layers were separated and the aqueous layer was extracted with DCM. The combined organics were dried over $Na_2SO_4$, filtered and concentrated to dryness. The crude material was purified by silica gel chromatography (hexanes/EtOAc) to afford (4S)-2-benzyl 1-tert-butyl 4-(benzyloxy)-2-(4-(4,4,5,5-tetramethyl-1,3,2-dioxaborolan-2-yl)butylpyrrolidine-1,2-dicarboxylate (Intermediate 7, 2.0 g, 61% yield) as a mixture of rotamers. Purified material was subjected to chiral SFC [(S,S)Whelk-O1 column, 21.2× 250 mm, 5 μm, Temperature=23° C., Mobile phase=0-15% MeOH:CO2, UV detection @220 nm, loading=33 mg/inj, conc=220 ng/mL in MeOH, flow rate=75 mL/min, Outlet Pressure=100 bar] to give two diastereomers. The stereochemistry for the major isomer was assigned as the anti-addition product and the minor isomer was assigned as the syn-addition product. The minor isomer (368 mg, 0.620 mmol) was dissolved in ethyl acetate (6.2 mL) and treated with Pd/C (10% wt, 132 mg, 0.124 mmol). The flask was equipped with a balloon of $H_2$ and the suspension stirred overnight at room temperature. The reaction mixture was filtered through diatomaceous earth and rinsed with methanol. The filtrate was concentrated under reduced pressure to afford (2R,4S)-1-(tert-butoxycarbonyl)-4-hydroxy-2-(4-(4,4,5,5-tetramethyl-1,3,2-dioxaborolan-2-(butyl)pyrrolidine-2-carboxylic acid (Intermediate 8, 228 mg, 98% yield) as a mixture of rotamers which was used without further purification. $^1$H NMR (300 MHz, DMSO-$d_6$) δ 0.57-0.74 (2H, m), 1.17 (12H, s), 1.24-1.47 (13H, m), 1.59-1.78 (1H, m), 1.78-1.96 (1H, m), 2.01-2.20 (2H, m), 2.84-3.09 (1H, m), 3.58-3.73 (1H, m), 4.14-4.31 (1H, m), 4.98-5.09 (1H, m), 12.20-12.60 (1H, m); m/z (ES$^+$) [M+H]$^+$=414.

Example 2: (2R,4S)-2-(4-boronobutyl)-4-hydroxypyrrolidine-2-carboxylic acid

Trifluoroacetic acid (0.65 mL, 8.4 mmol) was added to a solution of (2R,4S)-1-(tert-butoxycarbonyl)-4-hydroxy-2-(4-(4,4,5,5-tetramethyl-1,3,2-dioxaborolan-2-yl)butyl)pyrrolidine-2-carboxylic acid (Intermediate 8, 175 mg, 0.423 mmol) in DCM (4 mL). The resulting solution stirred at room temperature for 1 h and was then concentrated under vacuum. The crude amino acid was dissolved in $Et_2O$ (3 mL) and 1M aq HCl (3 mL). Phenylboronic acid (103 mg, 0.847 mmol) was added and the clear biphasic solution stirred at room temperature for 1 h. The reaction mixture was diluted with water and washed with $Et_2O$. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% to 100% acetonitrile in water) to obtain (2R,4S)-2-(4-boronobutyl)-4-hydroxypyrrolidine-2-carboxylic acid (Example 2, 33 mg, 33% yield) as a white solid. $^1$H NMR (400 MHz, $D_2O$) δ 0.67-0.78 (2H, m), 1.08-1.41 (4H, m), 1.81-2.12 (3H, m), 2.51 (1H, dd), 3.22-3.37 (2H, m), 4.46-4.56 (1H, m); m/z (ES$^+$) [M+H]$^+$=232.

Example 3: (2R,4R)-2-(4-boronobutyl)-4-hydroxypyrrolidine-2-carboxylic acid

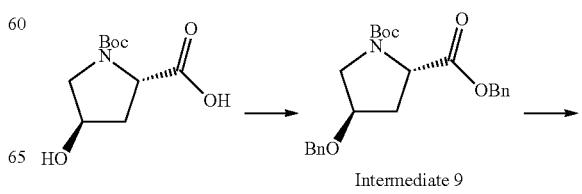

Intermediate 9

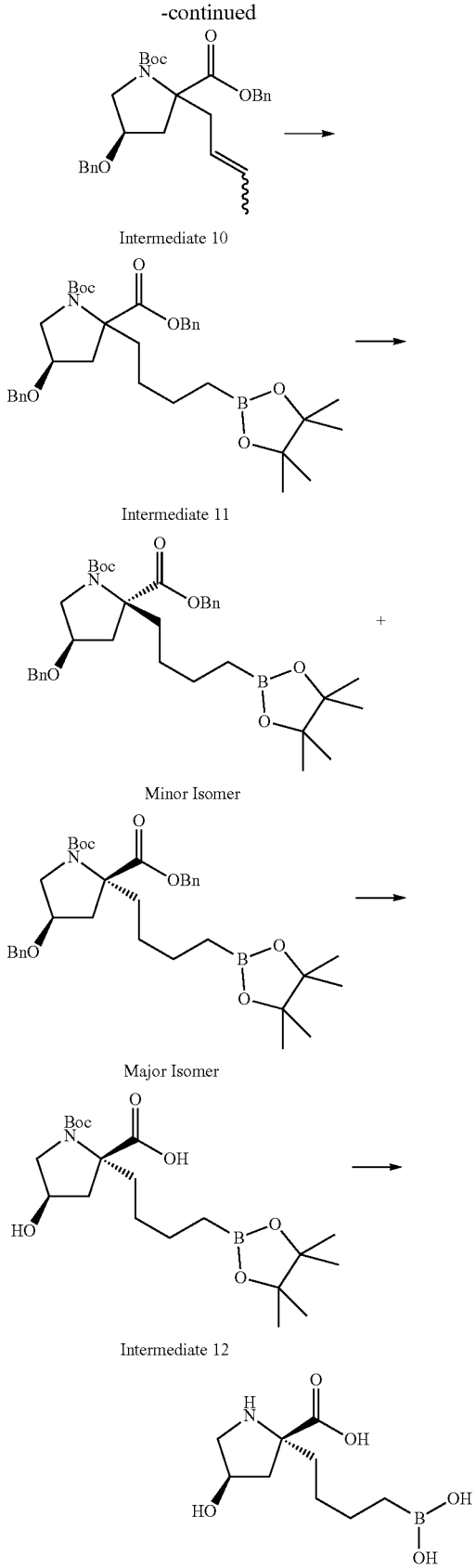

Intermediate 10

Intermediate 11

Minor Isomer

Major Isomer

Intermediate 12

Example 3

Intermediate 9: (2S,4R)-2-benzyl 1-tert-butyl 4-(benzyloxy)pyrrolidine-1,2-dicarboxylate (2S,4R)-1-(tert-butoxycarbonyl)-4-hydroxypyrrolidine-2-carboxylic acid (5.00 g, 21.6 mmol) was dissolved in DMF (73 mL) and the solution was cooled to 0° C. Sodium hydride (60% wt in mineral oil, 1.81 g, 45.4 mmol) was added portionwise and the suspension stirred at 0° C. for 1 h. Benzyl bromide (12.86 mL, 108.1 mmol) was added and the reaction mixture stirred overnight while slowly warming to RT. The crude reaction mixture was diluted with ethyl acetate (250 mL) and washed sequentially with citric acid (10% aq) and water. The organics were dried over $Na_2SO_4$, filtered and concentrated to dryness. The crude material was purified by silica gel chromatography (hexanes/EtOAc) to afford product (Intermediate 9, 5.9 g, 66% yield) as a mixture of rotamers. $^1$H NMR (300 MHz, DMSO-d6) δ 1.27-1.39 (9H, s×2) rotamers, 1.95-2.08 (1H, m), 2.34-2.47 (1H, m), 3.41-3.53 (2H, m), 4.17 (1H, br s), 4.28 (1H, q), 4.43-4.55 (2H, m), 5.06-5.22 (2H, m), 7.25-7.41 (10H, m); m/z (ES$^+$) [M+H]$^+$=412.

Intermediate 10: (4R)-2-benzyl 1-tert-butyl 4-(benzyloxy)-2-(but-2-enyl)pyrrolidine-1,2-dicarboxylate (2S,4R)-2-Benzyl 1-tert-butyl 4-(benzyloxy)pyrrolidine-1,2-dicarboxylate (Intermediate 9, 2.75 g, 6.68 mmol) and crotyl bromide (1.03 mL, 10.0 mmol) were dissolved in THF (45 mL) and the solution was cooled to −78° C. under an atmosphere of $N_2$. The solution was treated with dropwise addition of a solution of KHMDS (0.5M in toluene, 20.1 mL, 10.0 mmol). The reaction mixture was slowly warmed to room temperature and stirred for 3 h. The crude reaction mixture was quenched with water and the volatiles were removed in vacuo. The crude mixture was diluted in DCM and the layers were separated. The organic layer was washed with water, dried over $Na_2SO_4$, filtered and concentrated to dryness. The crude material was purified by silica gel chromatography (hexanes/EtOAc) to afford product (Intermediate 10, 1.23 g, 40% yield) as a mixture of rotamers and E/Z olefins. $^1$H NMR (300 MHz, DMSO-d$_6$) δ 1.25-1.34 (9H, s×2) rotamers, 1.45-1.63 (3H, m), 2.12-2.64 (2H, m), 2.64-3.04 (1H, m), 3.06-3.19 (1H, m), 3.31-3.45 (1H, m), 3.46-3.81 (1H, m), 4.03-4.21 (1H, m), 4.30-4.55 (2H, m), 4.90-5.16 (2H, m), 5.16-5.34 (1H, m), 5.38-5.68 (1H, m), 7.25-7.41 (10H, m). m/z (ES$^+$) [M+H]$^+$=466.

Intermediate 12: (2R,4R)-1-(tert-butoxycarbonyl)-4-hydroxy-2-(4-(4,4,5,5-tetramethyl-1,3,2-dioxaborolan-2-yl)butyl)pyrrolidine-2-carboxylic acid Bis(1,5-cyclooctadiene)diiridium(I) dichloride (177 mg, 0.264 mmol) and bis(diphenylphosphino)methane (203 mg, 0.527 mmol) were added to an oven-dried round-bottom flask. The flask was sealed and purged with $N_2$. The solids were dissolved in DCM (15 mL) and 4,4,5,5-tetramethyl-1,3,2-dioxaborolane (0.84 mL, 5.8 mmol) was slowly added to the solution. The reaction was stirred at room temperature for 10 min. (4R)-2-Benzyl 1-tert-butyl 4-(benzyloxy)-2-(but-2-enyl)pyrrolidine-1,2-dicarboxylate (Intermediate 10, 1.23 g, 2.64 mmol) was added to the reaction as a solution in DCM (10 mL) and the reaction mixture stirred overnight. The reaction mixture was diluted with DCM and quenched with water. The layers were separated and the aqueous layer was extracted with DCM. The combined organics were dried over $Na_2SO_4$, filtered and concentrated to dryness. The crude material was purified by silica gel chromatography (hexanes/EtOAc) to afford (4R)-2-benzyl 1-tert-butyl 4-(benzyloxy)-2-(4-(4,4,5,5-tetramethyl-1,3,2-dioxaborolan-2-yl)butyl)pyrrolidine-1,2-dicarboxylate (Intermediate 11, 950 mg, 60% yield). Purified material was subjected to chiral SFC [(S,S)Whelk-O1 column, 21.2×250 mm, 5 μm, Temperature=23° C., Mobile phase=0-15% MeOH:CO2, UV detection @ 220 nm, loading=33 mg/inj, conc=220 ng/mL in MeOH, flow rate=75 mL/min, Outlet Pressure=100 bar] to give two diastereomers. The stereochemistry for the major isomer was assigned as the anti-addition product and the minor isomer was assigned as the syn-addition product. The major isomer (385 mg, 0.649 mmol) was dissolved in ethyl acetate (6.4 mL) and treated with Pd/C (10% wt, 138 mg, 0.130 mmol). The flask was equipped with a balloon of $H_2$ and the suspension stirred overnight at room temperature. The reaction mixture was filtered through diatomaceous earth and rinsed with methanol. The filtrate was concentrated under reduced pressure to afford the product (Intermediate 12, 249 mg, 93% yield) as a mixture of rotamers. $^1$H NMR (300 MHz, DMSO-$d_6$) δ 0.61-0.73 (2H, m), 0.97-1.11 (1H, m), 1.12-1.23 (12H, m), 1.25-1.44 (12H, m), 1.51-1.71 (1H, m), 1.84-2.04 (2H, m), 2.05-2.19 (2H, m), 3.12-3.29 (1H, m), 3.37-3.59 (1H, m), 4.09-4.23 ($^1$H, m); m/z (ES$^+$) [M+H]$^+$=414.

Example 3: (2R,4R)-2-(4-boronobutyl)-4-hydroxy-pyrrolidine-2-carboxylic acid

Trifluoroacetic acid (0.65 mL, 8.5 mmol) was added to a solution of (2R,4R)-1-(tert-butoxycarbonyl)-4-hydroxy-2-(4-(4,4,5,5-tetramethyl-1,3,2-dioxaborolan-2-yl)butyl)pyrrolidine-2-carboxylic acid (Intermediate 12, 197 mg, 0.179 mmol) in DCM (3 mL). The resulting solution stirred at room temperature for 1 h and was then concentrated under vacuum. The crude amino acid was dissolved in Et$_2$O (3 mL) and 1M aq HCl (3 mL). Phenylboronic acid (102 mg, 0.837 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% acetonitrile in water) to afford (2R,4R)-2-(4-boronobutyl)-4-hydroxypyrrolidine-2-carboxylic acid (Example 3, 25 mg, 25% yield) as a white solid. $^1$H NMR (300 MHz, D$_2$O) δ 0.68-0.78 (2H, m), 1.13-1.43 (4H, m), 1.64-1.79 (1H, m), 1.94-2.14 (2H, m), 2.47 (1H, d), 3.39 (2H, m), 4.46-4.53 (1H, m). m/z (ES$^+$) [M+H]$^+$=232.

Example 4: (2S,4S)-4-amino-2-(4-boronobutyl)pyrrolidine-2-carboxylic acid

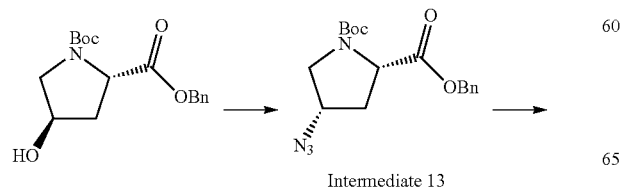

Intermediate 13

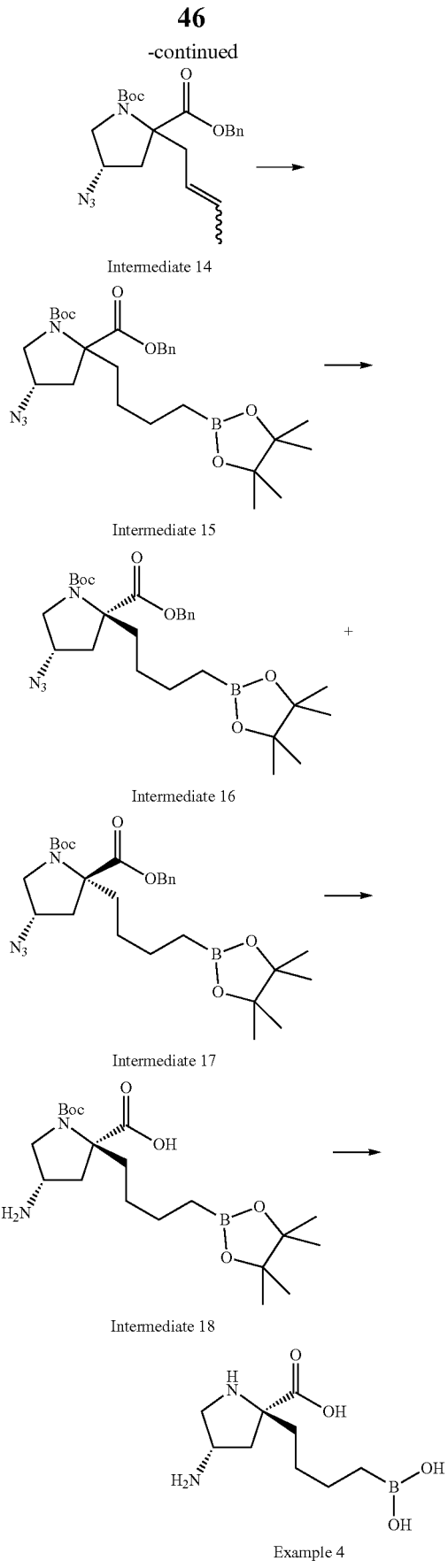

Intermediate 14

Intermediate 15

Intermediate 16

Intermediate 17

Intermediate 18

Example 4

Intermediate 13: (2S,4S)-2-benzyl 1-tert-butyl 4-azidopyrrolidine-1,2-dicarboxylate Methanesulfonyl chloride (0.71 mL, 9.2 mmol) was added dropwise to a solution of 2-benzyl 1-(tert-butyl) (2S,4R)-4-hydroxypyrrolidine-1,2-dicarboxylate (2.45 g, 7.26 mmol) and triethylamine (1.27 mL, 9.15 mmol) in DCM (9.6 mL) at 0° C. The reaction mixture stirred at 0° C. for 1 h before warming to room temperature with stirring for an additional 1 h. The reaction mixture was diluted with dichloromethane and washed with water. The organic layer was dried over $Na_2SO_4$, filtered and concentrated to dryness to afford 2-benzyl 1-(tert-butyl) (2S,4R)-4-((methylsulfonyl)oxy)pyrrolidine-1,2-dicarboxylate (2.9 g, 95% yield) which was used without further purification. m/z (ES$^+$) [M+H]$^+$=400. Sodium azide (1.65 g, 25.4 mmol) was added to a solution of 2-benzyl 1-(tert-butyl) (2S,4R)-4-((methylsulfonyl)oxy)pyrrolidine-1,2-dicarboxylate (2.90 g, 7.26 mmol) in DMF (7.2 mL). The reaction mixture was heated to 50° C. and stirred overnight. The reaction mixture was cooled to room temperature and concentrated. The resulting residue was diluted with EtOAc and washed with water. The organic layer was dried over $Na_2SO_4$, filtered and concentrated to dryness. Crude material was purified by silica gel chromatography (hexanes/EtOAc) to afford the product (Intermediate 13, 2.00 g, 80% yield) as a mixture of rotamers. $^1$H NMR (300 MHz, DMSO-$d_6$) δ 1.27 and 1.40 (9H, s×2) rotamers, 1.96-2.02 (1H, m), 2.53-2.63 (1H, m), 3.24-3.29 (1H, m), 3.58-3.66 (1H, m), 4.32-4.41 (2H, m), 5.06-5.22 (2H, m), 7.33-7.39 (5H, m); m/z (ES$^+$) [M+H]$^+$=347.

Intermediate 14: (4S)-2-benzyl 1-tert-butyl 4-azido-2-(but-2-enyl)pyrrolidine-1,2-dicarboxylate (2S,4S)-2-benzyl 1-tert-butyl 4-azidopyrrolidine-1,2-dicarboxylate (Intermediate 13, 1.00 g, 2.89 mmol) and crotyl bromide (0.44 mL, 4.3 mmol) were dissolved in THF (20 mL) and the solution was cooled to −78° C. under an atmosphere of $N_2$. The solution was treated with dropwise addition of a solution of KHMDS (0.5M in toluene, 8.66 mL, 4.33 mmol). The reaction mixture was slowly warmed to room temperature and stirred for 3 h. The crude reaction mixture was quenched with water and the volatiles were removed in vacuo. The crude mixture was diluted in DCM and the layers were separated. The organic layer was washed with water, dried over $Na_2SO_4$, filtered and concentrated to dryness. The crude material was purified by silica gel chromatography (hexanes/EtOAc) to afford the product (Intermediate 14, 750 mg, 65% yield) as a mixture of rotamers and E/Z olefins. $^1$H NMR (300 MHz, DMSO-$d_6$) δ 1.25-1.34 (9H, s×2) rotamers, 1.55-1.64 (3H, m), 1.99-2.15 (1H, m), 2.33-2.62 (2H, m), 2.73-3.10 (1H, m), 3.26-3.39 (1H, m), 3.52-3.84 (1H, m), 4.24-4.33 (1H, m), 5.03-5.21 (2H, m), 5.28-5.35 (1H, m), 5.49-5.65 (1H, m), 7.31-7.36 (5H, m); m/z (ES$^+$) [M+H]$^+$=401.

Intermediate 16: (2S,4S)-2-benzyl 1-tert-butyl 4-azido-2-(4-(4,4,5,5-tetramethyl-1,3,2-dioxaborolan-2-yl)butyl)pyrrolidine-1,2-dicarboxylate and Intermediate 17: (2R,4S)-2-benzyl 1-tert-butyl 4-azido-2-(4-(4,4,5,5-tetramethyl-1,3,2-dioxaborolan-2-yl)butyl)pyrrolidine-1,2-dicarboxylate Bis(1,5-cyclooctadiene)diiridium(I) dichloride (126 mg, 0.188 mmol) and bis(diphenylphosphino)methane (144 mg, 0.375 mmol) were added to an oven-dried round-bottom flask. The flask was sealed and purged with $N_2$. The solids were dissolved in DCM (10 mL) and 4,4,5,5-tetramethyl-1,3,2-dioxaborolane (0.60 mL, 4.1 mmol) was slowly added to the solution. The reaction was stirred at room temperature for 10 min. (4S)-2-benzyl 1-tert-butyl 4-azido-2-(but-2-enyl)pyrrolidine-1,2-dicarboxylate (Intermediate 14, 750 mg, 1.87 mmol) was added to the reaction as a solution in DCM (8 mL) and the reaction mixture stirred overnight at room temperature. The reaction mixture was diluted with DCM and quenched with water. The layers were separated and the aqueous layer was extracted with DCM. The combined organics were dried over $Na_2SO_4$, filtered and concentrated to dryness. The crude material was purified by silica gel chromatography (hexanes/EtOAc) to afford (4S)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 15, 678 mg, 68% yield). Purified material was subjected to chiral SFC [(S,S)Whelk-O1 column, 21.2×250 mm, 5 µm, Temperature=23° C., Mobile phase=0-15% MeOH:CO2, UV detection @ 220 nm, loading=33 mg/inj, conc=220 ng/mL in MeOH, flow rate=75 mL/min, Outlet Pressue=100 bar] to give two diastereomers. The stereochemistry for the major isomer was assigned as the anti-addition product Intermediate 16 and the minor isomer the syn-addition product Intermediate 17.

Intermediate 16 (Isomer 1, 608 mg): (2S,4S)-2-benzyl 1-tert-butyl 4-azido-2-(4-(4,4,5,5-tetramethyl-1,3,2-dioxaborolan-2-yl)butyl)pyrrolidine-1,2-dicarboxylate. $^1$H NMR (500 MHz, DMSO-$d_6$) δ 0.64-0.72 (2H, m), 1.04-1.12 (1H, m), 1.13-1.20 (12H, m), 1.22-1.39 (12H, m), 1.69-1.80 (1H, m), 2.01-2.23 (2H, m), 2.36-2.48 (1H, m), 3.35-3.42 (1H, m), 3.58-3.69 (1H, m), 4.33 (1H, quin), 5.05-5.17 (2H, m), 7.31-7.40 (5H, m); m/z (ES$^+$) [M+H]$^+$=529.

Intermediate 17 (Isomer 2, 220 mg): (2R,4S)-2-benzyl 1-tert-butyl 4-azido-2-(4-(4,4,5,5-tetramethyl-1,3,2-dioxaborolan-2-yl)butyl)pyrrolidine-1,2-dicarboxylate.

Intermediate 18: (2S,4S)-4-Amino-1-(tert-butoxycarbonyl)-2-(4-(4,4,5,5-tetramethyl-1,3,2-dioxaborolan-2-yl)butyl)pyrrolidine-2-carboxylic acid (2S,4S)-2-Benzyl 1-tert-butyl 4-azido-2-(4-(4,4,5,5-tetramethyl-1,3,2-dioxaborolan-2-yl)butyl)pyrrolidine-1,2-dicarboxylate (Intermediate 16, 255 mg, 0.483 mmol) was dissolved in ethyl acetate (5 mL) and methanol (5 mL) and treated with Pd/C (10% wt, 128 mg, 0.120 mmol). The flask was equipped with a balloon of $H_2$ and the suspension stirred overnight at room temperature. The reaction mixture was filtered through diatomaceous earth and rinsed with methanol. The filtrate was concentrated under reduced pressure to afford the product (Intermediate 18, 190 mg, 95% yield) as a mixture of rotamers which was used without further purification. $^1$H NMR (300 MHz, DMSO-$d_6$) δ 0.66 (2H, t), 0.88-1.03 (1H, m), 1.16 (12H, s), 1.24-1.38 (13H, m), 1.40-1.56 (1H, m), 1.80-1.91 (1H, m), 2.00-2.15 (2H, m), 3.17-3.28 (1H, m), 3.58-3.61 (1H, m), 3.80 (1H, dd), 9.01 (2H, br s); m/z (ES+) [M+H]$^+$=413.

Example 4: (2S,4S)-4-Amino-2-(4-boronobutyl)pyrrolidine-2-carboxylic acid

Trifluoroacetic acid (0.71 mL, 9.2 mmol) was added to a solution of (2S,4S)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 18, 190 mg, 0.461 mmol) in DCM (4 mL). The resulting solution stirred at room temperature for 1 h and was then concentrated under vacuum. The crude amino acid was dissolved in $Et_2O$ (3 mL)

and 1M aq HCl (3 mL). Phenylboronic acid (112 mg, 0.919 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% acetonitrile in water) to afford (2S,4S)-4-amino-2-(4-boronobutyl)pyrrolidine-2-carboxylic acid (Example 4, 40 mg, 37% yield) as a white solid. $^1$H NMR (300 MHz, D$_2$O) δ 0.73 (2H, t), 1.10-1.42 (4H, m), 1.69 (1H, ddd), 1.86-1.99 (1H, m), 2.10-2.30 (2H, m), 3.05 (1H, dd), 3.44 (1H, dd), 3.69 (1H, quin); m/z (ES$^+$) [M+H]$^+$=231.

Example 5: (2R,4S)-4-Amino-2-(4-boronobutyl)pyrrolidine-2-carboxylic acid

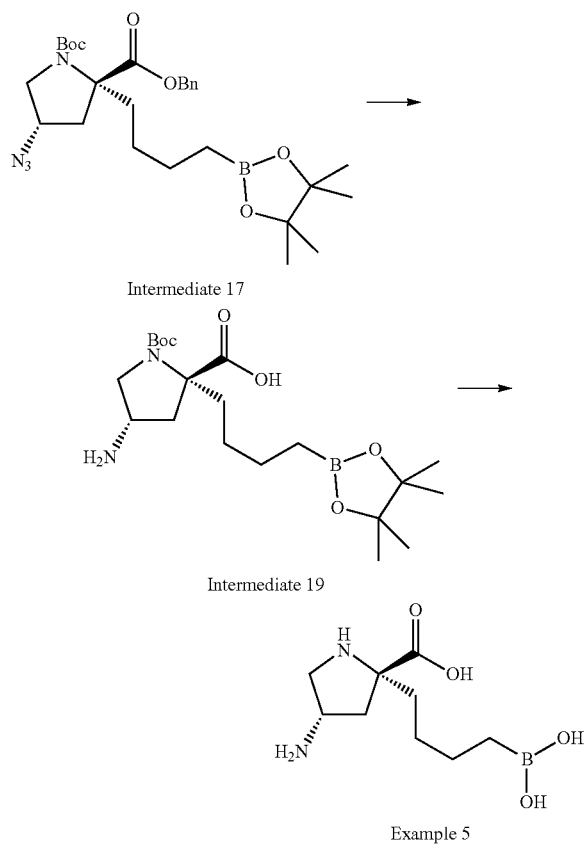

Intermediate 19: (2R,4S)-4-amino-1-(tert-butoxycarbonyl)-2-(4-(4,4,5,5-tetramethyl-1,3,2-dioxaborolan-2-yl)butyl)pyrrolidine-2-carboxylic acid (2R,4S)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 17, 220 mg, 0.416 mmol) was dissolved in ethyl acetate (5 mL) and methanol (5 mL) and treated with Pd/C (10% wt, 111 mg, 0.104 mmol). The flask was equipped with a balloon of H$_2$ and the suspension stirred overnight at room temperature. The reaction mixture was filtered through diatomaceous earth and rinsed with methanol. The filtrate was concentrated under reduced pressure to afford the product (Intermediate 19, 150 mg, 87% yield) as a mixture of rotamers which was used without further purification. $^1$H NMR (300 MHz, DMSO-d$_6$) δ 0.64-0.71 (2H, m), 1.17 (12H, s), 1.31-1.40 (15H, m), 1.49-1.93 (3H, m), 2.02-2.26 (3H, m), 3.38-3.47 (1H, m), 3.72-3.81 (1H, m); m/z (ES$^+$) [M+H]$^+$=413.

Example 5: (2R,4S)-4-amino-2-(4-boronobutyl)pyrrolidine-2-carboxylic acid

Trifluoroacetic acid (0.56 mL, 7.3 mmol) was added to a solution of (2R,4S)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 19, 150 mg, 0.364 mmol) in DCM (3 mL). The resulting solution stirred at room temperature for 1 h and was then concentrated under vacuum. The crude amino acid was dissolved in Et$_2$O (2 mL) and 1M aq HCl (2 mL). Phenylboronic acid (99 mg, 0.81 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10%0 to 100% acetonitrile in water) to afford (2R,4S)-4-amino-2-(4-boronobutyl)pyrrolidine-2-carboxylic acid (Example 5, 33 mg, 39% yield) as a white solid. $^1$H NMR (400 MHz, D$_2$O) δ 0.72 (1H, m), 1.11-1.39 (3H, m), 1.46-1.55 (1H, m), 1.63-1.79 (2H, m), 1.95-2.05 (1H, m), 2.58-2.65 (1H, m), 2.87-2.95 (1H, m), 3.48-3.58 (3H, m); m/z (ES$^+$) [M+H]$^+$=231.

Example 6: (2S,4R)-4-amino-2-(4-boronobutyl)pyrrolidine-2-carboxylic acid

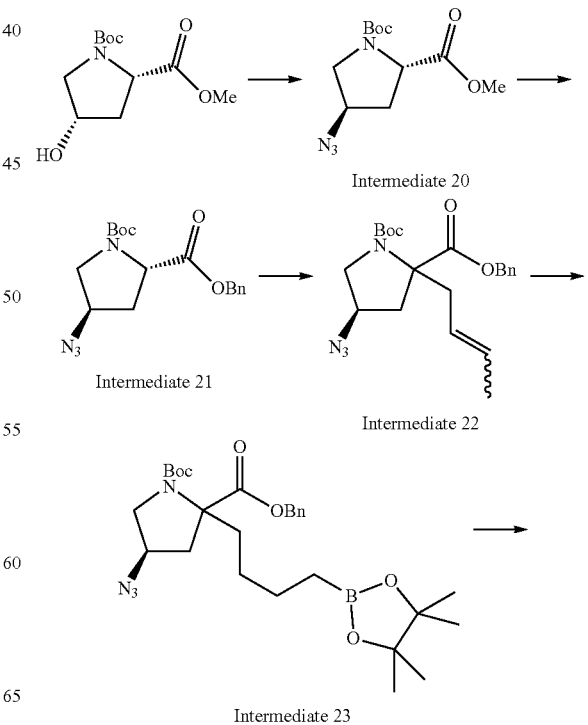

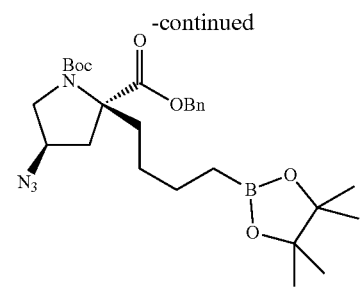

Intermediate 24

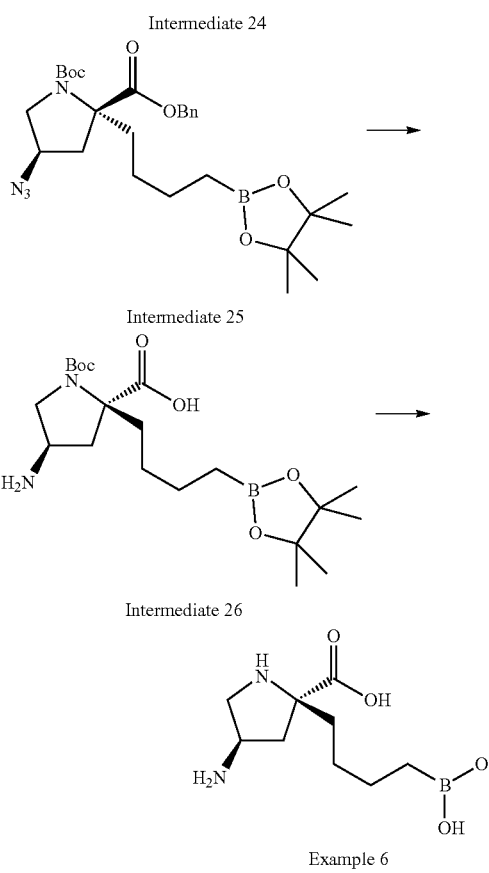

Intermediate 25

Intermediate 26

Example 6

Intermediate 20: (2S,4R)-1-tert-butyl 2-methyl 4-azidopyrrolidine-1,2-dicarboxylate Methanesulfonyl chloride (2.86 mL, 36.7 mmol) was added dropwise to a solution of (2S,4S)-1-tert-butyl 2-methyl 4-hydroxypyrrolidine-1,2-dicarboxylate (7.50 g, 30.6 mmol) and triethylamine (5.11 mL, 36.7 mmol) in DCM (38 mL) at 0° C. The reaction mixture stirred at 0° C. for 1 h before warming to room temperature with stirring for an additional 1 h. The reaction mixture was diluted with dichloromethane and washed with water. The organic layer was dried over $Na_2SO_4$, filtered and concentrated to dryness to afford 1-(tert-butyl) 2-methyl (2S,4S)-4-((methylsulfonyl)oxy)pyrrolidine-1,2-dicarboxylate (9.9 g, 100% yield) which was used without further purification. m/z (ES$^+$) [M+NH$_4$]$^+$=341.

Sodium azide (5.96 g, 91.7 mmol) was added to a solution of 1-(tert-butyl) 2-methyl (2S,4S)-4-((methylsulfonyl)oxy)pyrrolidine-1,2-dicarboxylate (9.89 g, 30.6 mmol) in DMF (30 mL). The reaction mixture was heated to 50° C. and stirred overnight. The reaction mixture was cooled to room temperature and concentrated. The resulting residue was diluted with EtOAc and washed with water. The organic layer was dried over $Na_2SO_4$, filtered and concentrated to dryness. Crude material was purified by silica gel chromatography (hexanes/EtOAc) to afford the product (Intermediate 20, 5.95 g, 72% yield) as a mixture of rotamers. $^1$H NMR (300 MHz, DMSO-d$_6$) δ 1.33 and 1.40 (9H, s×2) rotamers, 2.08-2.22 (1H, m), 2.26-2.41 (1H, m), 3.41 (1H, dt), 3.48-3.61 (1H, m), 3.65 and 3.68 (3H, s×2) rotamers, 4.22 (1H, dd), 4.30-4.43 (1H, m); m/z (ES$^+$) [M+H]$^+$=271.

Intermediate 21: (2S,4R)-2-benzyl 1-tert-butyl 4-azidopyrrolidine-1,2-dicarboxylate A solution of sodium hydroxide (5.28 g, 132 mmol) in water (22 mL) was added dropwise to a solution of (2S,4R)-1-tert-butyl 2-methyl 4-azidopyrrolidine-1,2-dicarboxylate (Intermediate 20, 5.95 g, 22.0 mmol) in THF (44 mL) and MeOH (22 mL) at 0° C. The reaction mixture stirred overnight while slowly warming to room temperature. The volatiles were removed in vacuo and the aqueous layer was acidified to pH ~3 with 5 M HCl and extracted with DCM. The combined organics were dried over $Na_2SO_4$, filtered and concentrated to dryness to afford (2S,4R)-4-azido-1-(tert-butoxycarbonyl)pyrrolidine-2-carboxylic acid (5.64 g, 100% yield) as a mixture of rotamers which was used without further purification. $^1$H NMR (300 MHz, DMSO-d$_6$) δ 1.35 and 1.40 (9H, s×2) rotamers, 2.07-2.18 (1H, m), 2.26-2.38 (1H, m), 3.34-3.44 (1H, m), 3.48-3.63 (1H, m), 4.09-4.17 (1H, m), 4.30-4.37 (1H, m); m/z (ES$^-$) [M+HCOO]$^-$=301.

Benzyl bromide (2.83 mL, 23.8 mmol) was added dropwise to a solution of (2S,4R)-4-azido-1-(tert-butoxycarbonyl)pyrrolidine-2-carboxylic acid (5.19 g, 19.9 mmol) and triethylamine (3.46 mL, 24.8 mmol) in DMF (60 mL) and the reaction mixture stirred overnight at room temperature. The volatiles were removed in vacuo and the resulting residue was dissolved in EtOAc and washed with water. The organic layer was dried over $Na_2SO_4$, filtered and concentrated to dryness. Crude material was purified by silica gel chromatography (hexanes/EtOAc) to afford the product (Intermediate 21, 5.09 g, 74% yield). $^1$H NMR (300 MHz, DMSO-d$_6$) δ 1.26 and 1.39 (9H, s×2) rotamers, 2.11-2.23 (1H, m), 2.31-2.43 (1H, m), 3.43 (1H, ddd), 3.50-3.59 (1H, m), 4.25-4.40 (2H, m), 5.07-5.22 (2H, m), 7.31-7.40 (5H, m); m/z (ES$^+$) [M+H]$^+$=347.

Intermediate 22: (4R)-2-benzyl 1-tert-butyl 4-azido-2-(but-2-enyl)pyrrolidine-1,2-dicarboxylate (2S,4R)-2-benzyl 1-tert-butyl 4-azidopyrrolidine-1,2-dicarboxylate (Intermediate 21, 5.09 g, 14.7 mmol) and crotyl bromide (2.27 mL, 22.0 mmol) were dissolved in THF (100 mL) and the solution was cooled to −78° C. under an atmosphere of $N_2$. The solution was treated with dropwise addition of a solution of KHMDS (0.5M in toluene, 44.1 mL, 22.0 mmol). The reaction mixture was slowly warmed to room temperature and stirred for 3 h. The crude reaction mixture was quenched with water and the volatiles were removed in vacuo. The crude mixture was diluted in DCM and the layers were separated. The organic layer was washed with water, dried over $Na_2SO_4$, filtered and concentrated to dryness. The crude material was purified by silica gel chromatography (hexanes/EtOAc) to afford the product (Intermediate 22, 4.6 g, 78% yield) as a mixture of rotamers and E/Z olefins. $^1$H NMR (300 MHz, DMSO-d$_6$) δ 1.26-1.43 (9H, m), 1.59-1.66 (3H, m), 2.07-2.17 (1H, m), 2.32-2.48

(2H, m), 2.57-3.12 (2H, m), 3.35-3.82 (1H, m), 4.20-4.38 (1H, m), 5.02-5.22 (2H, m), 5.24-5.41 (1H, m), 5.46-5.68 (1H, m), 7.28-7.42 (5H, m); m/z (ES$^+$) [M+H]$^+$=401.

Intermediate 24: (2S,4R)-2-benzyl 1-tert-butyl 4-azido-2-(4-(4,4,5,5-tetramethyl-1,3,2-dioxaborolan-2-yl)butyl)pyrrolidine-1,2-dicarboxylate and Intermediate 25: (2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate Bis(1,5-cyclooctadiene)diiridium(I) dichloride (772 mg, 1.15 mmol) and bis(diphenylphosphino)methane (883 mg, 2.30 mmol) were added to an oven-dried round-bottom flask. The flask was sealed and purged with N$_2$. The solids were dissolved in DCM (66 mL) and 4,4,5,5-tetramethyl-1,3,2-dioxaborolane (3.67 mL, 25.3 mmol) was slowly added to the solution. The reaction stirred at room temperature for 10 min. (4R)-2-benzyl 1-tert-butyl 4-azido-2-(but-2-enyl)pyrrolidine-1,2-dicarboxylate (Intermediate 22, 4.60 g, 11.5 mmol) was added to the reaction as a solution in DCM (44 mL) and the reaction mixture stirred overnight. The reaction mixture was diluted with DCM and quenched with water. The layers were separated and the aqueous layer was extracted with DCM. The combined organics were dried over Na$_2$SO$_4$, filtered and concentrated to dryness. The crude material was purified by silica gel chromatography (hexanes/EtOAc) to afford (4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 23, 2.7 g, 44% yield). The purified material was subjected to chiral SFC (Chiralpak IG column, 21.2×250 mm, 5 µm, Temperature=23° C., Mobile phase=0-7% MeOH (w/ 0.2% NH$_4$OH):CO$_2$, UV detection @ 220 nm, loading=16.8 mg/inj, conc=112.5 ng/mL in MeOH, flow rate=70 mL/min, Outlet Pressure=100 bar] to give two diastereomers. The stereochemistry for the major diastereomer Intermediate 25 was assigned as the anti-addition product and the minor diastereomer Intermediate 24 the syn-addition product.

Intermediate 24 (436 mg): (2S,4R)-2-benzyl 1-tert-butyl 4-azido-2-(4-(4,4,5,5-tetramethyl-1,3,2-dioxaborolan-2-yl)butyl)pyrrolidine-1,2-dicarboxylate. $^1$H NMR (400 MHz, DMSO-d$_6$) δ 0.58-0.70 (2H, m), 1.17 (12H, s), 1.25-1.40 (13H, m), 1.74-1.83 (1H, s), 2.00-2.11 (2H, m), 2.38-2.47 (1H, m), 3.07-3.16 (1H, m), 3.81 (1H, m), 4.29-4.34 (1H, m), 5.04-5.17 (2H, m), 7.34-7.39 (m, 5H); m/z (ES$^+$) [M+H]$^+$=529.

Intermediate 25 (1.60 g): (2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate. $^1$H NMR (400 MHz, DMSO-d$_6$) δ 0.56-0.73 (2H, m), 0.98-1.13 (1H, m), 1.17 (12H, s), 1.26-1.37 (13H, m), 1.66-1.79 (1H, m), 2.01-2.22 (2H, m), 2.34-2.47 (1H, m), 3.60 (1H, br dd), 4.29-4.35 (1H, m), 5.04-5.18 (2H, m), 7.31-7.40 (5H, m); m/z (ES$^+$) [M+H]$^+$=529.

Intermediate 26: (2S,4R)-4-amino-1-(tert-butoxycarbonyl)-2-(4-(4,4,5,5-tetramethyl-1,3,2-dioxaborolan-2-yl)butyl)pyrrolidine-2-carboxylic acid (2S,4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 24, 236 mg, 0.447 mmol) was dissolved in ethyl acetate (4.5 mL) and treated with Pd/C (10% wt, 119 mg, 0.112 mmol). The flask was equipped with a balloon of H$_2$ and the suspension stirred overnight at room temperature. The reaction mixture was filtered through diatomaceous earth and rinsed with methanol. The filtrate was concentrated under reduced pressure to afford the product (Intermediate 26, 275 mg, 100% yield) which was used without further purification. $^1$H NMR (300 MHz, DMSO-d$_6$) δ 0.64-0.71 (2H, M), 1.17 (12H, s), 1.27-1.40 (15H, m), 1.57-1.82 (4H, m), 1.98-2.08 (3H, m), 3.70-3.78 (1H, m); m/z (ES$^+$) [M+H]$^+$=413.

Example 6: (2S,4R)-4-amino-2-(4-boronobutyl)pyrrolidine-2-carboxylic acid

Trifluoroacetic acid (0.69 mL, 8.9 mmol) was added to a solution of (2S,4R)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 26, 184 mg, 0.446 mmol) in DCM (4 mL). The resulting solution stirred at room temperature for 1 h and was then concentrated under vacuum. The crude amino acid was dissolved in Et$_2$O (2 mL) and 1M aq HCl (2 mL). Phenylboronic acid (109 mg, 0.894 mmol) was added and the clear biphasic solution stirred at room temperature for 1 h. The reaction mixture was diluted with water and washed with Et$_2$O. The aqueous layer was lyophilized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 100% acetonitrile in water) to afford (2S,4R)-4-amino-2-(4-boronobutyl)pyrrolidine-2-carboxylic acid (Example 6, 38 mg, 37% yield) as a white solid. $^1$H NMR (400 MHz, D$_2$O) δ 0.72 (2H, td), 1.09-1.19 (1H, m), 1.22-1.39 (3H, m), 1.65-1.76 (2H, m), 1.95-2.04 (1H, m), 2.58-2.64 (1H, m), 2.87-2.94 (1H, m), 3.48-3.57 (2H, m); m/z (ES$^+$) [M+H]$^+$=231.

Example 7: (2R,4R)-4-amino-2-(4-boronobutyl)pyrrolidine-2-carboxylic acid

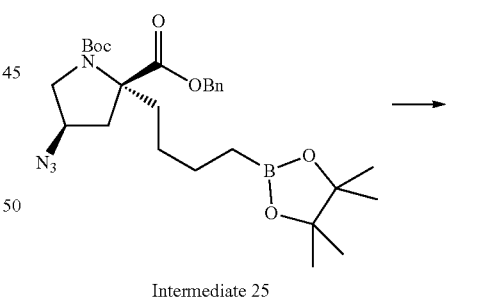

Intermediate 25

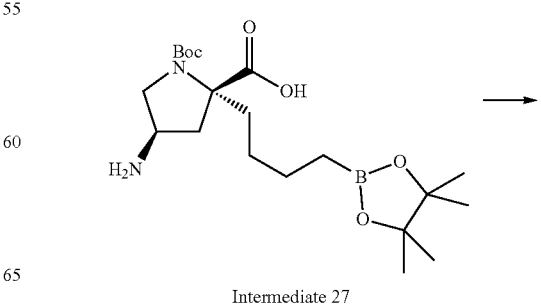

Intermediate 27

Intermediate 27: (2R,4R)-4-amino-1-(tert-butoxy-carbonyl)-2-(4-(4,4,5,5-tetramethyl-1,3,2-dioxaborolan-2-yl)butyl)pyrrolidine-2-carboxylic acid

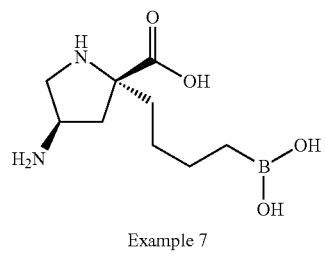

Example 7

(2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 25, 688 mg, 1.30 mmol) was dissolved in ethyl acetate (13 mL) and methanol (4 mL) and treated with Pd/C (10% wt, 346 mg, 0.325 mmol). The flask was equipped with a balloon of $H_2$ and the suspension stirred overnight at room temperature. The reaction mixture was filtered through diatomaceous earth and rinsed with methanol. The filtrate was concentrated under reduced pressure to afford the product (Intermediate 27, 500 mg, 93% yield) which was used without further purification. $^1$H NMR (300 MHz, DMSO-$d_6$) δ 0.67 (2H, t), 0.94-1.00 (1H, m), 1.17 (12H, s), 1.22-1.38 (11H, m), 1.43-1.53 (1H, m), 1.85 (1H, d), 2.00-2.15 (2H, m), 3.23 (2H, dd), 3.58-3.61 (1H, m), 3.80-3.88 (1H, m), 8.96 (2H, m); m/z (ES$^+$) [M+H]$^+$=413.

Example 7: (2R,4R)-4-amino-2-(4-boronobutyl)pyrrolidine-2-carboxylic acid

Trifluoroacetic acid (1.02 mL, 13.3 mmol) was added to a solution of (2R,4R)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 27, 275 mg, 0.667 mmol) in DCM (4 mL). The resulting solution stirred at room temperature for 1 h and was then concentrated under vacuum. The crude amino acid was dissolved in Et$_2$O (2 mL) and 1M aq HCl (2 mL). Phenylboronic acid (163 mg, 1.34 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% to 100% acetonitrile in water) to afford (2R,4R)-4-amino-2-(4-boronobutyl)pyrrolidine-2-carboxylic acid (Example 7, 53 mg, 34% yield) as a white solid. $^1$H NMR (400 MHz, D$_2$O) δ 0.76 (2H, dt), 1.10-1.46 (4H, m), 1.62-1.71 (1H, m), 1.84-1.96 (1H, m), 2.10-2.21 (1H, m), 2.22-2.32 (1H, m), 3.07 (1H, dd), 3.46 (1H, dd), 3.71 (1H, quin); m/z (ES$^+$) [M+H]$^+$=231.

Example 8: (2R,4R)-4-((S)-2-aminopropanamido)-2-(4-boronobutyl)pyrrolidine-2-carboxylic acid

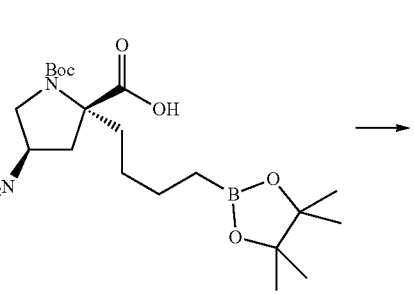

Intermediate 27

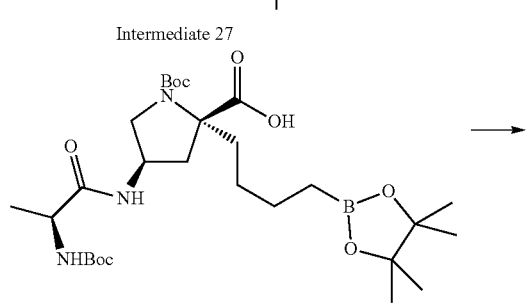

Intermediate 28

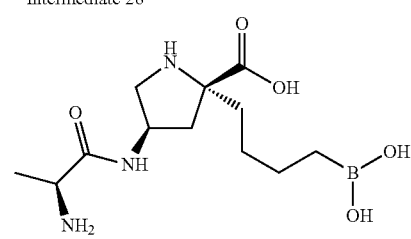

Example 8

Intermediate 28: (2R,4R)-1-(tert-butoxycarbonyl)-4-((S)-2-(tert-butoxycarbonylamino)propanamido)-2-(4-(4,4,5,5-tetramethyl-1,3,2-dioxaborolan-2-yl)butyl)pyrrolidine-2-carboxylic acid Triethylamine (0.18 mL, 1.3 mmol) and HATU (213 mg, 0.560 mmol) were added sequentially to a solution of Boc-Ala-OH (106 mg, 0.560 mmol) in DMF (2.4 mL) and the reaction stirred at room temperature for 30 min. (2R,4R)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 27, 210 mg, 0.509 mmol) was added to the reaction mixture as a solution in DMF (2.4 mL). The reaction stirred at room temperature overnight. The crude reaction mixture was concentrated and directly purified by silica gel chromatography (hexanes/EtOAc) to afford the product (Intermediate 28, 236 mg, 79% yield) as a mixture of rotamers. $^1$H NMR (300 MHz, DMSO-$d_6$) δ 0.65-0.72 (2H, m), 1.11-1.18 (18H, m), 1.26-1.37 (20H, m), 1.63-1.73 (1H, m), 2.02-2.25 (2H, m), 3.09-3.20 (1H, m), 3.59-3.72 (1H, m), 3.83-3.94 (1H, m), 4.18-4.29 (1H, m), 6.80 (1H, br s), 7.96 (1H, s), 13.78 (1H, br s); m/z (ES$^+$) [M+H]$^+$=584.

Example 8: (2R,4R)-4-((S)-2-aminopropanamido)-2-(4-boronobutyl)pyrrolidine-2-carboxylic acid Trifluoroacetic acid (0.62 mL, 8.1 mmol) was added to a solution of (2R,4R)-1-(tert-butoxycarbonyl)-4-((S)-2-(tert-butoxycarbonylamino)propanamido)-2-(4-(4,4,5,5-tetramethyl-1,3,2-dioxaborolan-2-yl)butyl)pyrrolidine-2-carboxylic acid (Intermediate 28, 236 mg, 0.404 mmol) in DCM (4 mL). The resulting solution stirred at room temperature for 1 h and was then concentrated under vacuum. The crude amino acid was dissolved in Et$_2$O (2 mL) and 1M aq HCl (2 mL). Phenylboronic acid (99 mg, 0.81 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% acetonitrile in water) to afford (2R,4R)-4-((S)-2-aminopropanamido)-2-(4-boronobutyl) pyrrolidine-2-carboxylic acid (Example 8, 18 mg, 15% yield) as a white solid and mixture of rotamers. $^1$H NMR (500 MHz, D$_2$O) δ 0.69 (2H, dt), 1.05-1.14 (1H, m), 1.21 (3H, d), 1.23-1.35 (3H, m), 1.65 (1H, dt), 1.91-1.96 (1H, m), 2.17 (1H, dd), 2.35 (1H, dd), 3.26 (1H, dd), 3.46-3.57 (2H, m), 4.29-4.34 (1H, m); m/z (ES$^+$) [M+H]$^+$=302.

Example 9: (2R,4R)-4-((S)-2-amino-3-methylbutanamido)-2-(4-boronobutyl)pyrrolidine-2-carboxylic acid

Intermediate 29: (2R,4R)-1-(tert-butoxycarbonyl)-4-((S)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid Triethylamine (0.21 mL, 1.5 mmol) and HATU (254 mg, 0.668 mmol) were added sequentially to a solution of Boc-Val-OH (145 mg, 0.668 mmol) in DMF (2.9 mL) and the reaction was stirred at room temperature for 30 min. (2R,4R)-4-amino-1-(tert-butoxycarbonyl)-2-(4-(4,4,5,5-tetramethyl-1,3,2-dioxaborolan-2-yl)butyl)pyrrolidine-2-carboxylic acid (Intermediate 27, 250 mg, 0.606 mmol) was added to the reaction mixture as a solution in DMF (2.9 mL). The reaction stirred at room temperature overnight. The crude reaction mixture was concentrated and directly purified by silica gel chromatography (hexanes/EtOAc) to afford the product (Intermediate 29, 250 mg, 67% yield) as a mixture of rotamers. $^1$H NMR (300 MHz, DMSO-d$_6$) δ 0.64-0.73 (2H, m), 0.73-0.85 (6H, m), 1.13-1.14 (1H, m), 1.17 (12H, s), 1.22-1.42 (22H, m), 1.56-1.75 (1H, m), 1.79-1.97 (1H, m), 2.00-2.26 (2H, m), 3.08-3.24 (1H, m), 3.54-3.77 (2H, m), 4.12-4.36 (1H, m), 6.58 (1H, t), 7.96-8.03 (2H, m); m/z (ES$^+$) [M+H]$^+$=584.

Example 9: (2R,4R)-4-((S)-2-amino-3-methylbutanamido)-2-(4-boronobutyl)pyrrolidine-2-carboxylic acid Trifluoroacetic acid (0.63 mL, 8.2 mmol) was added to a solution (2R,4R)-1-(tert-butoxycarbonyl)-4-((S)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid (Intermediate 29, 250 mg, 0.409 mmol) in DCM (4 mL). The resulting solution stirred at room temperature for 1 h and was then concentrated under vacuum. The crude amino acid was dissolved in Et$_2$O (2 mL) and 1M aq HCl (2 mL). Phenylboronic acid (99 mg, 0.81 mmol) was added and the clear biphasic solution stirred at room temperature for 1 h. The reaction mixture was diluted with water and washed with Et$_2$O. The aqueous layer was lyopholized and purified by ion exchange chromatography (PoraPak Rxn CX 60 cc column). The desired product was eluted from the column using 2M ammonia/methanol. The obtained material was further purified by reverse phase chromatography (RediSep Rf Gold® C18Aq, 0 to 10% acetonitrile in water) to afford (2R,4R)-4-((S)-2-amino-3-methylbutanamido)-2-(4-boronobutyl)pyrrolidine-2-carboxylic acid (Example 9, 28 mg, 20% yield) as a white solid and a mixture of rotamers. $^1$H NMR (300 MHz, D$_2$O) δ 0.66-0.76 (2H, m), 0.85 (6H, dd), 1.07-1.43 (4H, m), 1.55-1.68 (1H, m), 1.77-1.97 (2H, m), 2.13-2.33 (2H, m), 3.07 (1H, d), 3.08-3.16 (1H, m), 3.37-3.48 (1H, m), 4.27-4.40 (1H, m); m/z (ES$^+$) [M+H]$^+$=330.

Example 10: (2R,4R)-4-((R)-2-amino-3-methylbutanamido)-2-(4-boronobutyl)pyrrolidine-2-carboxylic acid

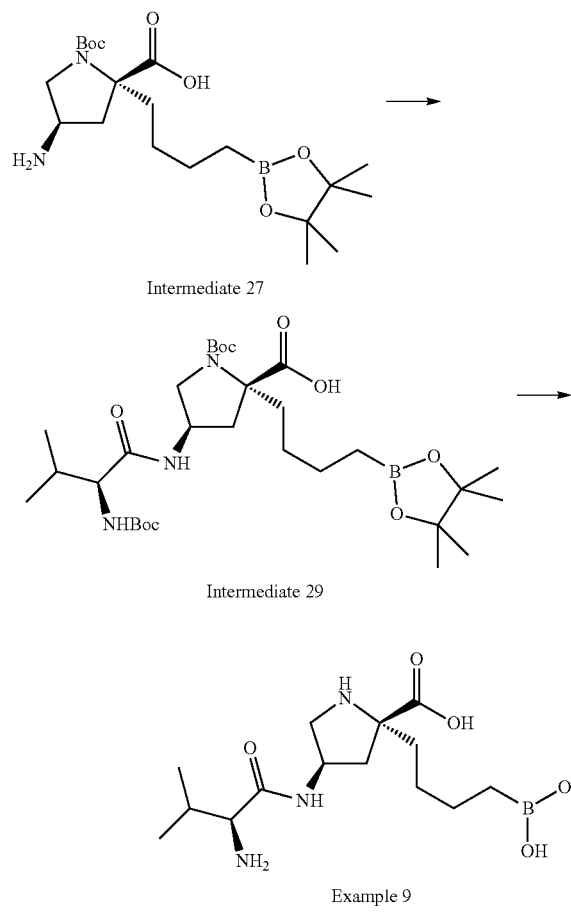

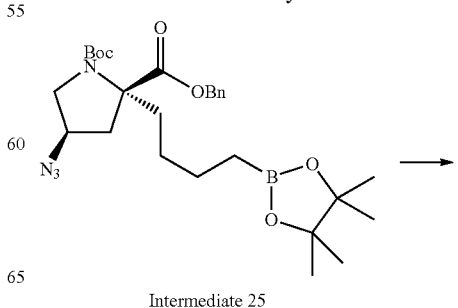

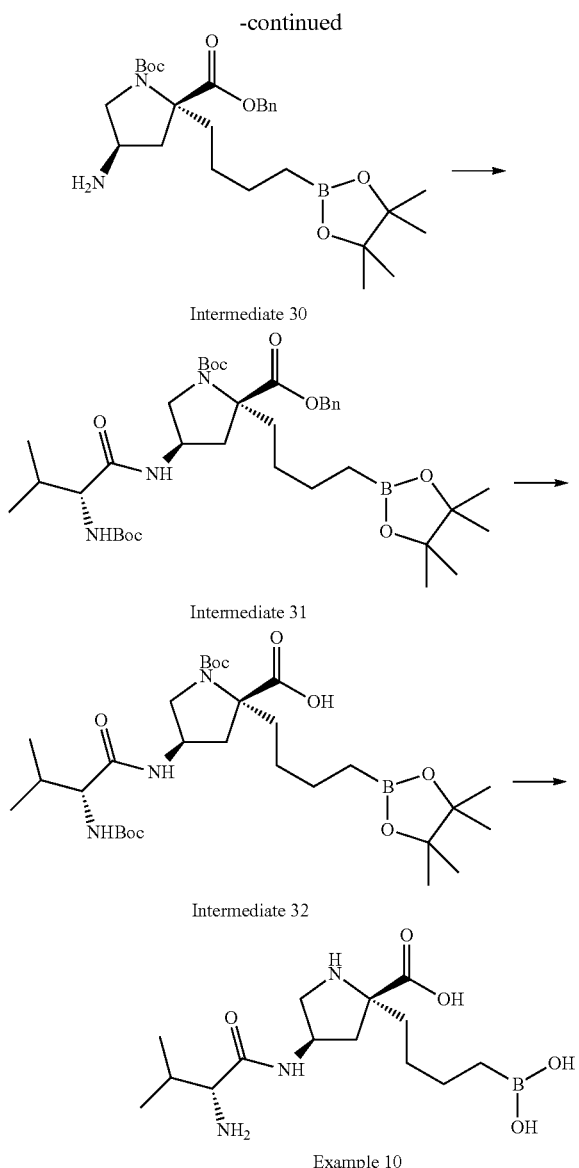

Intermediate 30

Intermediate 31

Intermediate 32

Example 10

Intermediate 30: (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate Lindlar catalyst (5% wt, 0.275 g, 2.58 mmol) was added to a solution of (2R,4R)-2-benzyl 1-tert-butyl 4-azido-2-(4-(4,4,5,5-tetramethyl-1,3,2-dioxaborolan-2-yl)butyl)pyrrolidine-1,2-dicarboxylate (Intermediate 25, 1.56 g, 2.95 mmol) in THF (25 mL). The suspension was stirred under a hydrogen atmosphere (balloon, flask evacuated and back-filled with hydrogen ×3) at room temperature for 8.5 h. The reaction mixture was diluted with MeOH, filtered through diatomaceous earth and the filtrate was concentrated to dryness. The crude material was purified by silica gel chromatography (1 to 15% MeOH in DCM) to afford (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 1.01 g, 68% yield) as a gum and as a mixture of rotamers. $^1$H NMR (500 MHz, CD$_2$Cl$_2$) δ 0.74 (2H, q), 1.20-1.22 (14H, m), 1.23-1.29 (2H, m), 1.32 (6H, s), 1.37-1.42 (5H, m), 1.74-1.83 (1H, m), 1.83-1.93 (1H, m), 2.11-2.19 (0.6H, m), 2.21-2.32 (1.4H, m), 3.19 (0.4H, dd), 3.28 (0.6H, dd), 3.44-3.51 (1H, m), 3.63 (1H, dd), 5.07-5.20 (2H, m), 7.28-7.34 (1H, m), 7.34-7.41 (4H, m); m/z (ES$^+$) [M+H]$^+$=503.

Intermediate 31: (2R,4R)-2-benzyl 1-tert-butyl 4-((R)-2-(tert-butoxycarbonylamino)-3-methylbutanamido)-2-(4-(4,4,5,5-tetramethyl-1,3,2-dioxaborolan-2-yl)butyl)pyrrolidine-1,2-dicarboxylate N,N-Diisopropylethylamine (0.235 mL, 1.34 mmol) was added slowly to a stirred solution of HATU (245 mg, 0.64 mmol) and Boc-D-Val-OH (117 mg, 0.54 mmol) in DMF (2 mL) at room temperature. The solution was stirred for 20 min and then a solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 270 mg, 0.54 mmol) in DMF (2 mL) was added. The reaction was stirred for 2.5 h, diluted with DCM (30 mL) and washed sequentially with water (3×25 mL) and saturated aqueous sodium chloride (30 mL). The organic layer was dried over MgSO$_4$, filtered and concentrated to dryness. The crude material was purified by silica gel chromatography (5 to 65% EtOAc in hexanes) to afford (2R,4R)-2-benzyl 1-tert-butyl 4-((R)-2-(tert-butoxycarbonylamino)-3-methylbutanamido)-2-(4-(4,4,5,5-tetramethyl-1,3,2-dioxaborolan-2-yl)butyl)pyrrolidine-1,2-dicarboxylate (Intermediate 31, 239 mg, 63% yield) as a colorless foam and as a mixture of rotamers. $^1$H NMR (500 MHz, CD$_2$Cl$_2$) δ 0.74-0.81 (2H, m), 0.84 (3H, d), 0.87-0.94 (3H, m), 1.24 (12H, s), 1.26-1.34 (2H, m), 1.37 (5H, s), 1.40-1.43 (2H, m), 1.45 (4H, s), 1.46 (9H, s), 1.78-1.89 (1H, m), 1.95-2.07 (2H, m), 2.21-2.29 (0.6H, m), 2.31-2.46 (1.4H, m), 3.51-3.60 (1.5H, m), 3.65 (0.5H, br d), 3.72 (1H, br dd), 4.49-4.58 (1H, m), 5.01 (1H, br d), 5.19-5.29 (2H, m), 6.93-7.09 (1H, m), 7.36-7.40 (1H, m), 7.43 (4H, app d); m/z (ES$^+$) [M+H]$^+$=702.

Intermediate 32: (2R,4R)-1-(tert-butoxycarbonyl)-4-((R)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid Pd/C (10% wt, 25 mg, 0.23 mmol) was added to a solution of (2R,4R)-2-benzyl 1-tert-butyl 4-((R)-2-(tert-butoxycarbonylamino)-3-methylbutanamido)-2-(4-(4,4,5,5-tetramethyl-1,3,2-dioxaborolan-2-yl)butyl)pyrrolidine-1,2-dicarboxylate (Intermediate 31, 239 mg, 0.34 mmol) in EtOAc (4 mL). The suspension was stirred under a hydrogen atmosphere (balloon, flask evacuated and back-filled with hydrogen ×3) at room temperature for 2 h. The reaction mixture was diluted with MeOH, filtered through diatomaceous earth and the filtrate was concentrated to dryness. The crude material was purified by silica gel chromatography (2 to 15% MeOH in DCM) to afford (2R,4R)-1-(tert-butoxycarbonyl)-4-((R)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid (Intermediate 32, 196 mg, 94% yield) as a white solid and as a mixture of rotamers. $^1$H NMR (500 MHz, DMSO-d$_6$) δ 0.63-0.71 (2H, m), 0.75-0.82 (6H, m), 1.15 (12H, s), 1.21-1.30 (2H, m), 1.32 (6H, s), 1.36 (13H, br s), 1.61-1.72 (1H, m), 1.81-1.90 (1H, m), 1.92-2.05 (2H, m), 2.05-2.13 (0.6H, m), 2.13-2.28 (1.4H, m), 3.03-3.14 (1H, m), 3.62 (0.6H, t), 3.66 (1.4H, t), 4.18-4.29 (1H, m), 6.59 (1H, d), 7.99 (1H, br s), 12.48 (0.4H, br s), 12.65 (0.6H, br s); m/z (ES$^+$) [M+H]$^+$=612.

Example 10: (2R,4R)-4-((R)-2-amino-3-methylbutanamido)-2-(4-boronobutyl)pyrrolidine-2-carboxylic acid Trifluoroacetic acid (0.37 mL, 4.8 mmol) was added dropwise to a stirred solution of (2R,4R)-1-(tert-butoxycarbonyl)-4-((R)-2-(tert-butoxycarbonylamino)-3-methylbutanamido)-2-(4-(4,4,5,5-tetramethyl-1,3,2-dioxaborolan-2-yl)butyl)pyrrolidine-2-carboxylic acid (Intermediate 32, 195 mg, 0.32 mmol) in DCM (2 mL). The reaction solution was stirred at room temperature for 22 h and was then concentrated under reduced pressure. The crude amino acid was dissolved in 1 M HCl aq (2 mL) and Et$_2$O (2 mL). Phenylboronic acid (117 mg, 0.96 mmol) was added and the clear biphasic solution stirred at room temperature for 5 h. The mixture was diluted with Et$_2$O (20 mL) and water (5 mL), and the layers were separated. The aqueous layer was washed with Et$_2$O and the aqueous layer was lyophilized. The resulting solid was dissolved in MeOH (3 mL) and purified by ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 0 to 80% acetonitrile in water) to afford (2R,4R)-4-((R)-2-amino-3-methylbutanamido)-2-(4-boronobutyl)pyrrolidine-2-carboxylic acid (Example 10, 46 mg, 44% yield) as a white solid. $^1$H NMR (500 MHz, D$_2$O) δ 0.73-0.80 (2H, m), 0.90 (6H, app t), 1.13-1.25 (1H, m), 1.26-1.35 (1H, m), 1.40 (2H, quin), 1.68-1.80 (1H, m), 1.85-1.96 (1H, m), 2.00 (1H, td), 2.29 (1H, dd), 2.37-2.45 (1H, m), 3.18 (1H, d), 3.28 (1H, dd), 3.59 (1H, dd), 4.36-4.49 (1H, m); m/z (ES$^+$) [M+H]$^+$=330.

Example 11: (2R,4R)-4-((S)-2-amino-3,3-dimethylbutanamido)-2-(4-boronobutyl)pyrrolidine-2-carboxylic acid

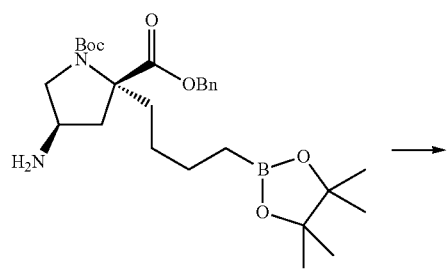

Intermediate 30

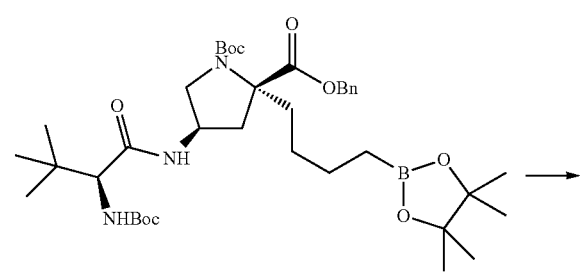

Intermediate 33

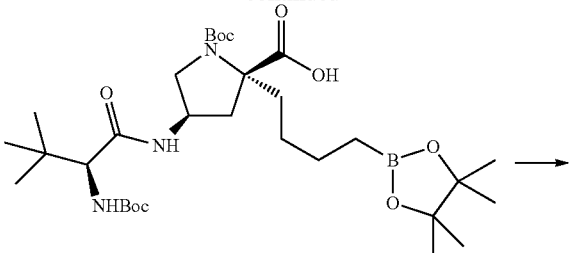

Intermediate 34

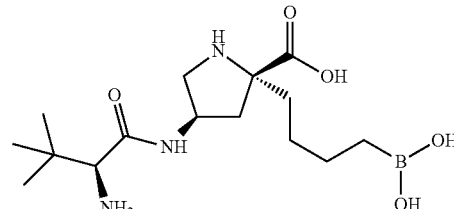

Example 11

Intermediate 33: (2R,4R)-2-benzyl 1-tert-butyl 4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-1,2-dicarboxylate N,N-Diisopropylethylamine (0.165 mL, 0.95 mmol) was added slowly to a stirred solution of HATU (158 mg, 0.42 mmol) and Boc-Tle-OH (92 mg, 0.40 mmol) in DMF (1.5 mL) at room temperature. The solution was stirred for 15 min and then a solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 190 mg, 0.38 mmol) in DMF (1.5 mL) was added. The reaction was stirred for 3 h, diluted with EtOAc (30 mL) and washed sequentially with water (3×25 mL), saturated aqueous NaHCO$_3$ (30 mL) and saturated aqueous sodium chloride (30 mL). The organic layer was dried over MgSO$_4$, filtered and concentrated to dryness. The crude material was purified by silica gel chromatography (5 to 65% EtOAc in hexanes) to afford (2R,4R)-2-benzyl 1-tert-butyl 4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-1,2-dicarboxylate (Intermediate 33, 261 mg, 96% yield) as a white solid and as a mixture of rotamers. $^1$H NMR (500 MHz, DMSO-d$_6$) δ 0.69 (2H, q), 0.87 (9H, s), 1.17 (12H, s), 1.26 (5H, s), 1.29-1.32 (1H, m), 1.34 (5H, s), 1.38 (9H, s), 1.72-1.85 (1H, m), 1.90-2.08 (2H, m), 2.06-2.18 (1H, m), 2.22-2.35 (2H, m), 3.11-3.22 (1H, m), 3.68-3.81 (2H, m), 4.23-4.37 (1H, m), 5.06-5.19 (2H, m), 6.40 (1H, t), 7.31-7.40 (5H, m), 8.11 (1H, d); m/z (ES$^+$) [M+Na]$^+$=738.

Intermediate 34: (2R,4R)-1-(tert-butoxycarbonyl)-4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-2-carboxylic acid Pd/C (10% wt, 25 mg, 0.23 mmol) was added to a solution of (2R,4R)-2-benzyl 1-tert-butyl 4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-1,2-dicarboxylate (Intermediate 33, 260 mg, 0.36 mmol) in EtOAc (4 mL). The suspension was stirred under a hydrogen atmosphere (balloon, flask evacuated and back-filled with hydrogen ×3) at room temperature for 15 h. The reaction mixture was diluted with MeOH, filtered through diatomaceous earth and the filtrate was concentrated to dryness. The crude material was purified by silica gel chromatography (2 to 10% MeOH in DCM) to afford (2R,4R)-1-(tert-butoxycarbonyl)-4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-2-carboxylic acid (Intermediate 34, 207 mg, 91% yield) as a white solid and as a mixture of rotamers. $^1$H NMR (500 MHz, DMSO-$d_6$) δ 0.63-0.72 (2H, m), 0.86 (9H, s), 1.09-1.20 (14H, m), 1.21-1.30 (2H, m), 1.33 (5H, s), 1.35-1.38 (13H, m), 1.61-1.73 (1H, m), 1.89-2.11 (2H, m), 2.14-2.27 (1H, m), 3.06-3.14 (1H, m), 3.59-3.72 (1H, m), 3.72-3.80 (1H, m), 4.20-4.30 (1H, m), 6.35 (1H, d), 8.08 (1H, br s), 12.47 (0.4H, br s), 12.63 (0.6H, br s); m/z (ES$^+$) [M+H]$^+$=626.

Example 11: (2R,4R)-4-((S)-2-amino-3,3-dimethylbutanamido)-2-(4-boronobutyl)pyrrolidine-2-carboxylic acid Trifluoroacetic acid (0.38 mL, 4.9 mmol) was added dropwise to a stirred solution of (2R,4R)-1-(tert-butoxycarbonyl)-4-((S)-2-(tert-butoxycarbonylamino)-3,3-dimethylbutanamido)-2-(4-(4,4,5,5-tetramethyl-1,3,2-dioxaborolan-2-yl)butyl)pyrrolidine-2-carboxylic acid (Intermediate 34, 206 mg, 0.33 mmol) in DCM (2 mL). The reaction was stirred at room temperature for 15 h and was then concentrated under reduced pressure. The crude amino acid was dissolved in 1 M HCl aq (4 mL) and Et$_2$O (4 mL). Phenylboronic acid (120 mg, 0.99 mmol) was added and the clear biphasic solution stirred at room temperature for 3 h. The mixture was diluted with Et$_2$O (20 mL) and water (5 mL), and the layers were separated. The aqueous layer was washed with Et$_2$O and the aqueous layer was lyophilized. The resulting solid was dissolved in MeOH (3 mL) and purified by ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 2 to 50% acetonitrile in water) to afford (2R,4R)-4-((S)-2-amino-3,3-dimethylbutanamido)-2-(4-boronobutyl)pyrrolidine-2-carboxylic acid (Example 11, 40 mg, 35% yield) as a white solid. $^1$H NMR (500 MHz, D$_2$O) δ 0.72 (2H, td), 0.89 (9H, s), 1.10-1.21 (1H, m), 1.22-1.30 (1H, m), 1.35 (2H, quin), 1.64-1.75 (1H, m), 1.90-2.02 (1H, m), 2.22-2.34 (2H, m), 3.04 (1H, s), 3.22 (1H, dd), 3.56 (1H, dd), 4.41 (1H, quin); m/z (ES$^+$) [M+H]$^+$=344.

Example 12: (2R,4R)-2-(4-boronobutyl)-4-((S)-pyrrolidine-2-carboxamido)pyrrolidine-2-carboxylic acid

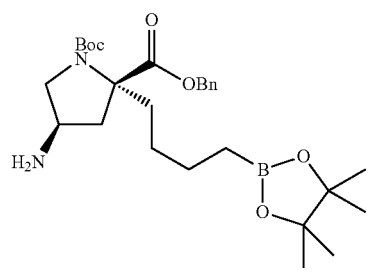

Intermediate 30

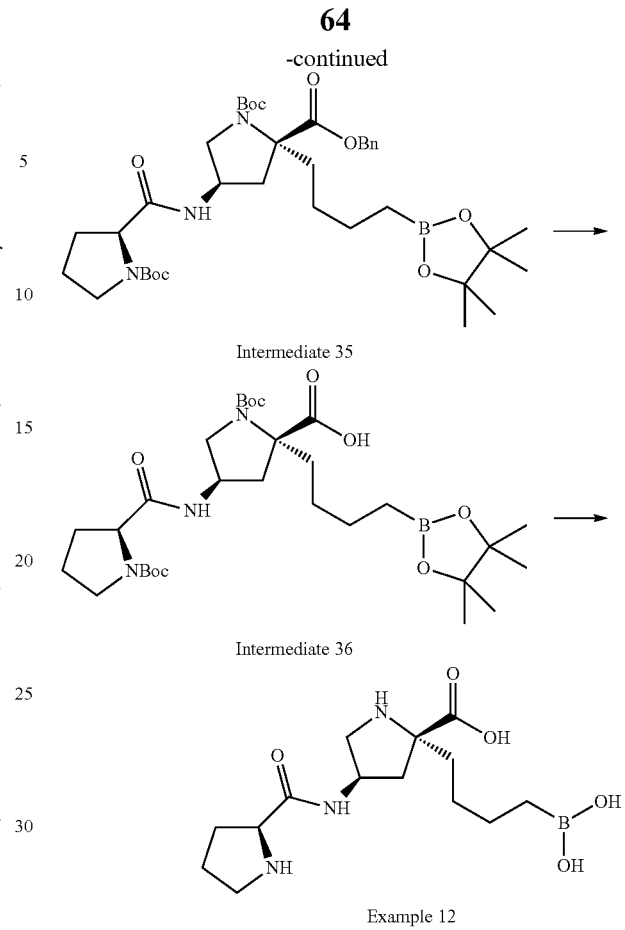

Intermediate 35

Intermediate 36

Example 12

Intermediate 35: (2R,4R)-2-benzyl 1-tert-butyl 4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-1,2-dicarboxylate N,N-Diisopropylethylamine (0.182 mL, 1.04 mmol) was added slowly to a stirred solution of HATU (175 mg, 0.46 mmol) and Boc-Pro-OH (94 mg, 0.44 mmol) in DMF (1.5 mL) at room temperature. The solution was stirred for 20 min and then a solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 210 mg, 0.42 mmol) in DMF (1.5 mL) was added. The reaction was stirred for 2 h, diluted with EtOAc (30 mL) and washed sequentially with water (3×25 mL), saturated aqueous NaHCO$_3$ and saturated aqueous sodium chloride (30 mL). The organic layer was dried over MgSO$_4$, filtered and concentrated to dryness. The crude material was purified by silica gel chromatography (5 to 100% EtOAc in hexanes) to afford (2R,4R)-2-benzyl 1-tert-butyl 4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-1,2-dicarboxylate (Intermediate 35, 249 mg, 85% yield) as a colorless film and as a mixture of rotamers. $^1$H NMR (500 MHz, CD$_2$Cl$_2$) δ 0.68-0.79 (2H, m), 1.20 (12H, s), 1.31 (5H, s), 1.36-1.48 (16H, m), 1.74-1.87 (3H, m), 1.89-2.10 (3H, m), 2.13-2.46 (2H, m), 3.27-3.40 (1H, m), 3.44 (2H, br s), 3.50-3.64 (2H, m), 3.78-4.05 (1H, m), 4.49 (1H, br s), 5.10-5.27 (2H, m), 7.10 (1H, br s), 7.30-7.42 (5H, m); m/z (ES$^+$) [M+H]$^+$=700.

Intermediate 36: (2R,4R)-1-(tert-butoxycarbonyl)-4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-2-carboxylic acid Pd/C (10% wt, 25 mg, 0.23 mmol) was added to a solution of (2R,4R)-2-benzyl 1-tert-butyl 4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-1,2-dicarboxylate (Intermediate 35, 249 mg, 0.36 mmol) in EtOAc (4 mL). The suspension was stirred under a hydrogen atmosphere (balloon, flask evacuated and back-filled with hydrogen ×3) at room temperature for 5 h. The reaction mixture was diluted with MeOH, filtered through diatomaceous earth and the filtrate was concentrated under reduced pressure to afford (2R,4R)-1-(tert-butoxycarbonyl)-4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-2-carboxylic acid (Intermediate 36, 207 mg, 87% yield) as a colorless film and as a mixture of rotamers which was used without further purification. $^1$H NMR (500 MHz, CD$_2$Cl$_2$) δ 0.66-0.83 (2H, m), 1.21 (12H, s), 1.34-1.51 (21H, m), 1.63-1.97 (4H, m), 2.06 (1H, m), 2.11-2.29 (2H, m), 2.33-2.67 (1H, m), 3.24-3.52 (3H, m), 3.53-3.67 (1H, m), 4.15-4.34 (1H, m), 4.47-4.74 (1H, m), 6.76-7.23 (1H, m), 7.17-7.69 (1H, m), 9.74 (1H, br s); m/z (ES$^+$) [M+H]$^+$=610.

Example 12: (2R,4R)-2-(4-boronobutyl)-4-((S)-pyrrolidine-2-carboxamido)pyrrolidine-2-carboxylic acid Trifluoroacetic acid (0.518 mL, 6.73 mmol) was added dropwise to a stirred solution of (2R,4R)-1-(tert-butoxycarbonyl)-4-((S)-1-(tert-butoxycarbonyl)pyrrolidine-2-carboxamido)-2-(4-(4,4,5,5-tetramethyl-1,3,2-dioxaborolan-2-yl)butyl)pyrrolidine-2-carboxylic acid (Intermediate 36, 205 mg, 0.34 mmol) in DCM (2 mL). The reaction was stirred at room temperature for 2 h and was then concentrated under reduced pressure. The crude amino acid was dissolved in 1 M HCl aq (4 mL) and Et$_2$O (4 mL). Phenylboronic acid (123 mg, 1.01 mmol) was added and the clear biphasic solution stirred at room temperature for 2 h. The mixture was diluted with Et$_2$O (20 mL) and water (5 mL), and the layers were separated. The aqueous layer was washed with Et$_2$O and the aqueous layer was lyophilized. The resulting solid was dissolved in MeOH (3 mL) and purified by ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 0 to 50% acetonitrile in water) to afford (2R,4R)-2-(4-boronobutyl)-4-((S)-pyrrolidine-2-carboxamido)pyrrolidine-2-carboxylic acid (Example 12, 89 mg, 81% yield) as a white solid. $^1$H NMR (500 MHz, D$_2$O) δ 0.70-0.79 (2H, m), 1.11-1.23 (1H, m), 1.24-1.33 (1H, m), 1.34-1.42 (2H, m), 1.60-1.71 (1H, m), 1.81-1.91 (3H, m), 1.91-1.99 (1H, m), 2.18 (1H, dd), 2.22-2.29 (1H, m), 2.40 (1H, dd), 3.08-3.16 (1H, m), 3.16-3.22 (1H, m), 3.25 (1H, dd), 3.48 (1H, dd), 3.99 (1H, dd), 4.29-4.38 (1H, m); m/z (ES$^+$) [M+H]$^+$=328.

Example 13: (2R,4R)-4-(2-aminoacetamido)-2-(4-boronobutyl)pyrrolidine-2-carboxylic acid

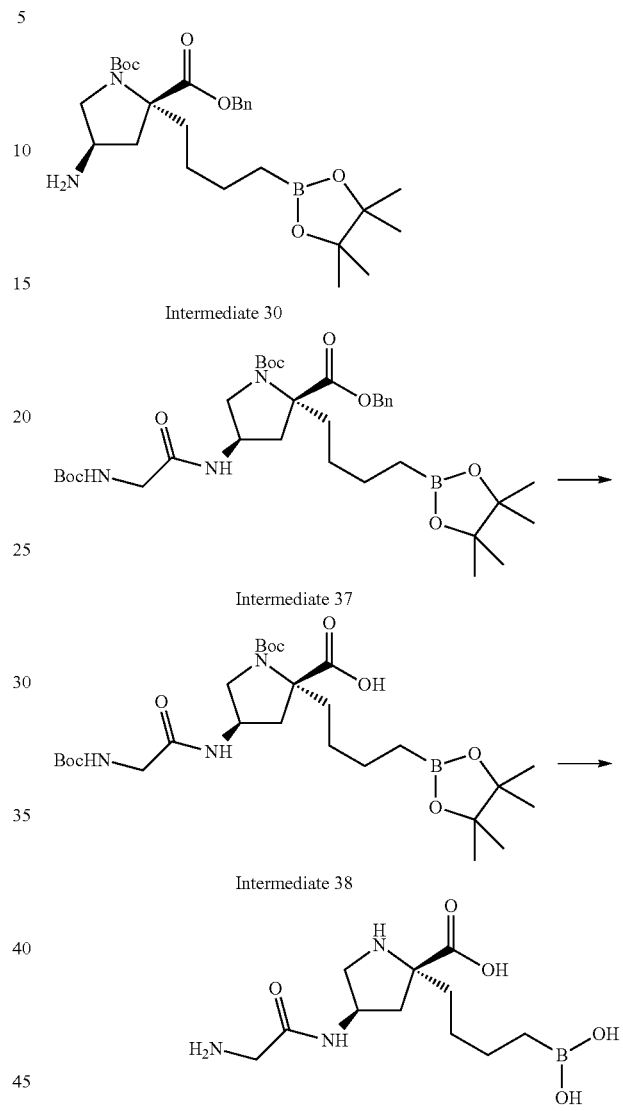

Intermediate 37: (2R,4R)-2-benzyl 1-tert-butyl 4-(2-(tert-butoxycarbonylamino)acetamido)-2-(4-(4,4,5,5-tetramethyl-1,3,2-dioxaborolan-2-yl)butyl)pyrrolidine-1,2-dicarboxylate N,N-Diisopropylethylamine (0.182 mL, 1.04 mmol) was added slowly to a stirred solution of HATU (175 mg, 0.46 mmol) and Boc-Gly-OH (77 mg, 0.44 mmol) in DMF (1.5 mL) at room temperature. The solution was stirred for 20 min and then a solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 210 mg, 0.42 mmol) in DMF (1.5 mL) was added. The reaction solution was stirred for 2 h, diluted with EtOAc (30 mL) and washed sequentially with water (3×25 mL), saturated aqueous NaHCO$_3$ and saturated aqueous sodium chloride (30 mL). The organic layer was dried over MgSO$_4$, filtered and concentrated to dryness. The crude material was purified by silica gel chromatography (10 to 100% EtOAc in hexanes) to afford (2R,4R)-2-benzyl 1-tert-butyl 4-(2-(tert-butoxycarbonylamino)acetamido)-2-(4-(4,4,5,5-tetramethyl-1,3,2-dioxaborolan-2-yl)butyl)pyrrolidine-1,2-dicarboxylate (Intermediate 37, 235 mg, 85% yield) as a colorless film and as a mixture of rotamers. $^1$H NMR (500 MHz, CD$_2$Cl$_2$) δ 0.70-0.78 (2H, m), 1.12-1.18 (1H, m), 1.20 (12H, s), 1.25-1.30 (1H, m), 1.33 (5H, s), 1.43 (15H, s), 1.74-1.86 (1H, m), 1.95 (0.5H, br d), 2.03 (0.5H, br d), 2.15-2.26 (1H, m), 2.26-2.37 (1H, m), 2.40 (1H, dd), 3.43-3.57 (3H, m), 3.57-3.64 (1H, m), 4.50 (1H, br s), 5.03 (0.5H, br s), 5.10 (0.5H, br s), 5.13-5.25 (1H, m), 7.01 (1H, dd), 7.32-7.37 (1H, m), 7.36-7.41 (4H, m); m/z (ES$^+$) [M+H]$^+$=660.

Intermediate 38: (2R,4R)-1-(tert-butoxycarbonyl)-4-(2-(tert-butoxycarbonylamino)acetamido)-2-(4-(4,4,5,5-tetramethyl-1,3,2-dioxaborolan-2-yl)butyl)pyrrolidine-2-carboxylic acid Pd/C (10% wt, 25 mg, 0.23 mmol) was added to a solution of (2R,4R)-2-benzyl 1-tert-butyl 4-(2-(tert-butoxycarbonylamino)acetamido)-2-(4-(4,4,5,5-tetramethyl-1,3,2-dioxaborolan-2-yl)butyl)pyrrolidine-1,2-dicarboxylate (Intermediate 37, 233 mg, 0.35 mmol) in EtOAc (4 mL). The suspension was stirred under a hydrogen atmosphere (balloon, flask evacuated and back-filled with hydrogen ×3) at room temperature for 6 h. The reaction mixture was diluted with MeOH, filtered through diatomaceous earth and the filtrate was concentrated to dryness to afford (2R,4R)-1-(tert-butoxycarbonyl)-4-(2-(tert-butoxycarbonylamino)acetamido)-2-(4-(4,4,5,5-tetramethyl-1,3,2-dioxaborolan-2-yl)butyl)pyrrolidine-2-carboxylic acid (Intermediate 38, 176 mg, 87% yield) as a colorless film and as a mixture of rotamers which was used without further purification. $^1$H NMR (500 MHz, CD$_2$Cl$_2$) δ 0.65-0.80 (2H, m), 1.11-1.18 (1H, m), 1.18-1.23 (12H, m), 1.25-1.32 (1H, m), 1.36-1.45 (13H, m), 1.47 (7H, s), 1.70-1.83 (0.4H, m), 1.84-1.95 (0.6H, m), 2.06-2.27 (2H, m), 2.33-2.47 (0.4H, m), 2.63 (0.6H, br d), 3.44-3.62 (2H, m), 3.63-3.82 (2H, m), 4.28 (0.6H, br s), 4.36-4.60 (0.4H, m), 5.26 (0.6H, br s), 5.58-5.90 (0.3H, m), 6.83 (0.6H, br s), 6.97-7.44 (0.4H, m); m/z (ES$^+$) [M+H]$^+$=570.

Example 13: (2R,4R)-4-(2-aminoacetamido)-2-(4-boronobutyl)pyrrolidine-2-carboxylic acid Trifluoroacetic acid (0.476 mL, 6.18 mmol) was added dropwise to a stirred solution of (2R,4R)-1-(tert-butoxycarbonyl)-4-(2-(tert-butoxycarbonylamino)acetamido)-2-(4-(4,4,5,5-tetramethyl-1,3,2-dioxaborolan-2-yl)butyl)pyrrolidine-2-carboxylic acid (Intermediate 38, 176 mg, 0.31 mmol) in DCM (2 mL). The reaction solution was stirred at room temperature for 2 h and was then concentrated under reduced pressure. The crude amino acid was dissolved in 1 M HCl aq (4 mL) and Et$_2$O (4 mL). Phenylboronic acid (113 mg, 0.93 mmol) was added and the clear biphasic solution stirred at room temperature for 2 h. The mixture was diluted with Et$_2$O (20 mL) and water (5 mL), and the layers were separated. The aqueous layer was washed with Et$_2$O and the aqueous layer was lyophilized. The resulting solid was dissolved in MeOH (3 mL) and purified by ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 0 to 40% acetonitrile in water) to afford (2R,4R)-4-(2-aminoacetamido)-2-(4-boronobutyl)pyrrolidine-2-carboxylic acid (Example 13, 62 mg, 70% yield) as a white solid. $^1$H NMR (500 MHz, D$_2$O) δ 0.76 (2H, td), 1.15-1.25 (1H, m), 1.26-1.34 (1H, m), 1.36-1.46 (2H, m), 1.69-1.79 (1H, m), 2.00 (1H, ddd), 2.27 (1H, dd), 2.44 (1H, dd), 3.33 (1H, dd), 3.42 (2H, s), 3.59 (1H, dd), 4.36-4.45 (1H, m); m/z (ES$^+$) [M+H]$^+$=288.

Example 14: (2R,4R)-4-((S)-2-aminobutanamido)-2-(4-boronobutyl)pyrrolidine-2-carboxylic acid

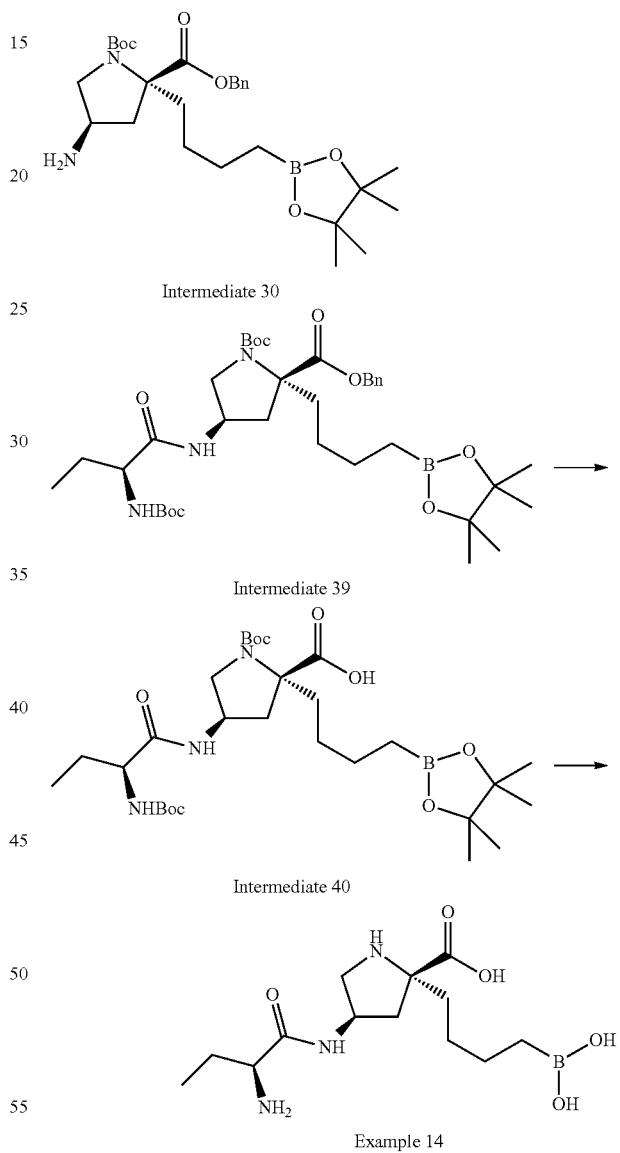

Intermediate 30

Intermediate 39

Intermediate 40

Example 14

Intermediate 39: (2R,4R)-2-benzyl 1-tert-butyl 4-((S)-2-(tert-butoxycarbonylamino)butanamido)-2-(4-(4,4,5,5-tetramethyl-1,3,2-dioxaborolan-2-yl)butyl)pyrrolidine-1,2-dicarboxylate HATU (804 mg, 2.11 mmol) was added to a solution of Boc-Abu-OH (430 mg, 2.11 mmol) in DMF (4 mL) and the reaction stirred at room temperature for 10 min. (2R,4R)-

2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 885 mg, 1.76 mmol) was added to the reaction mixture as a solution in DMF (3 mL). N,N-Diisopropylethylamine (0.75 mL, 4.3 mmol) was added and the reaction stirred at room temperature overnight. The reaction was then diluted with water (15 mL) and Et$_2$O (10 mL). The layers were separated and the aqueous layer was extracted with Et$_2$O (2×10 mL). The combined organics were washed with 5% aqueous lithium chloride (10 mL), dried over MgSO$_4$, filtered, and concentrated to dryness. The crude material was purified by silica gel chromatography (hexanes/EtOAc) to afford (2R,4R)-2-benzyl 1-tert-butyl 4-((S)-2-(tert-butoxycarbonylamino)butanamido)-2-(4-(4,4,5,5-tetramethyl-1,3,2-dioxaborolan-2-yl)butyl)pyrrolidine-1,2-dicarboxylate (Intermediate 39, 766 mg, 63% yield) as a white solid. $^1$H NMR (500 MHz, CDCl$_3$) δ 0.70-0.84 (5H, m), 1.09-1.19 (1H, m), 1.21 (12H, s), 1.36-1.46 (18H, m), 1.46-1.97 (7H, m), 2.12-2.45 (2H, m), 3.45-3.60 (1H, m), 3.68 (1H, br d), 3.78-3.94 (1H, m), 4.42-4.64 (1H, m), 4.73-5.03 (1H, m), 5.07-5.33 (2H, m), 7.09 (1H, br d), 7.28-7.40 (5H, m). m/z (ES$^+$) [M+H]$^+$=688.

Intermediate 40: (2R,4R)-1-(tert-butoxycarbonyl)-4-((S)-2-(tert-butoxycarbonylamino)butanamido)-2-(4-(4,4,5,5-tetramethyl-1,3,2-dioxaborolan-2-yl)butyl)pyrrolidine-2-carboxylic acid (2R,4R)-2-benzyl 1-tert-butyl 4-((S)-2-(tert-butoxycarbonylamino)butanamido)-2-(4-(4,4,5,5-tetramethyl-1,3,2-dioxaborolan-2-yl)butyl)pyrrolidine-1,2-dicarboxylate (Intermediate 39, 766 mg, 1.11 mmol) was dissolved in EtOAc (11 mL) and treated with Pd/C (10 wt %, 119 mg, 0.11 mmol). The flask was equipped with a balloon of H$_2$ and the suspension stirred overnight at room temperature. The reaction mixture was filtered through diatomaceous earth and rinsed with EtOAc and methanol. The filtrate was concentrated to dryness. The crude material was purified by silica gel chromatography (hexanes/EtOAc) to afford (2R,4R)-1-(tert-butoxycarbonyl)-4-((S)-2-(tert-butoxycarbonylamino)butanamido)-2-(4-(4,4,5,5-tetramethyl-1,3,2-dioxaborolan-2-yl)butyl)pyrrolidine-2-carboxylic acid (Intermediate 40, 470 mg, 70% yield) as a white foam. $^1$H NMR (500 MHz, CDCl$_3$) δ 0.67-0.82 (2H, m), 0.89 (3H, br t), 1.11-1.28 (14H, m), 1.37-1.51 (20H, m), 1.53-1.65 (1H, m), 1.65-1.94 (2H, m), 2.02-2.12 (1H, m), 2.13-2.31 (1H, m), 2.70 (1H, br d), 3.40-3.62 (2H, m), 3.88-4.04 (1H, m), 4.26 (1H, br s), 5.01 (1H, br s), 6.73 (1H, br d); m/z (ES$^+$) [M+H]$^+$=598.

Example 14: (2R,4R)-4-((S)-2-aminobutanamido)-2-(4-boronobutyl)pyrrolidine-2-carboxylic acid Phenylboronic acid (192 mg, 1.57 mmol) was added to a solution of (2R,4R)-1-(tert-butoxycarbonyl)-4-((S)-2-(tert-butoxycarbonylamino)butanamido)-2-(4-(4,4,5,5-tetramethyl-1,3,2-dioxaborolan-2-yl)butyl)pyrrolidine-2-carboxylic acid (Intermediate 40, 470 mg, 0.79 mmol) in 2 M HCl aq (5 mL) and the reaction stirred at room temperature for 16 h. The reaction was diluted with water (10 mL) and Et$_2$O (10 mL) and the layers were separated. The aqueous layer was washed with Et$_2$O (3×5 mL) and then lyophilized to a foam. The organic layer was concentrated under vacuum. The resulting residue was diluted in 4 M HCl in dioxane (4 mL, 16 mmol) and the resulting solution stirred at room temperature for 20 h. The reaction was diluted with water (10 mL) and Et$_2$O (10 mL) and the layers were separated. The aqueous layer was washed with Et$_2$O (3×5 mL) and then lyophilized to a foam. The foams from these two operations were combined and the resulting crude amino acid was purified by ion exchange chromatography (Silicycle SiliaSep SPE-R51230B-20X 5 g column). The desired product was eluted from the column using a 5% ammonia in MeOH solution. The obtained material was further purified by reverse phase chromatography (RediSep Rf Gold® C18Aq, 0 to 25% acetonitrile in water) to afford (2R,4R)-4-((S)-2-aminobutanamido)-2-(4-boronobutyl)pyrrolidine-2-carboxylic acid (Example 14, 96 mg, 39% yield) as a white solid. $^1$H NMR (500 MHz, D$_2$O) δ 0.55-0.82 (2H, m), 0.88 (3H, t), 1.12-1.48 (4H, m), 1.56-1.81 (3H, m), 1.86-2.10 (1H, m), 2.12-2.53 (2H, m), 3.15-3.37 (1H, m), 3.41-3.53 (1H, m), 3.62 (1H, dd), 4.35-4.52 (1H, m); m/z (ES$^+$) [M–H$_2$O+H]$^+$=298.

Example 15: (2R,4R)-4-((2S,3S)-2-amino-3-methylpentanamido)-2-(4-boronobutyl)pyrrolidine-2-carboxylic acid

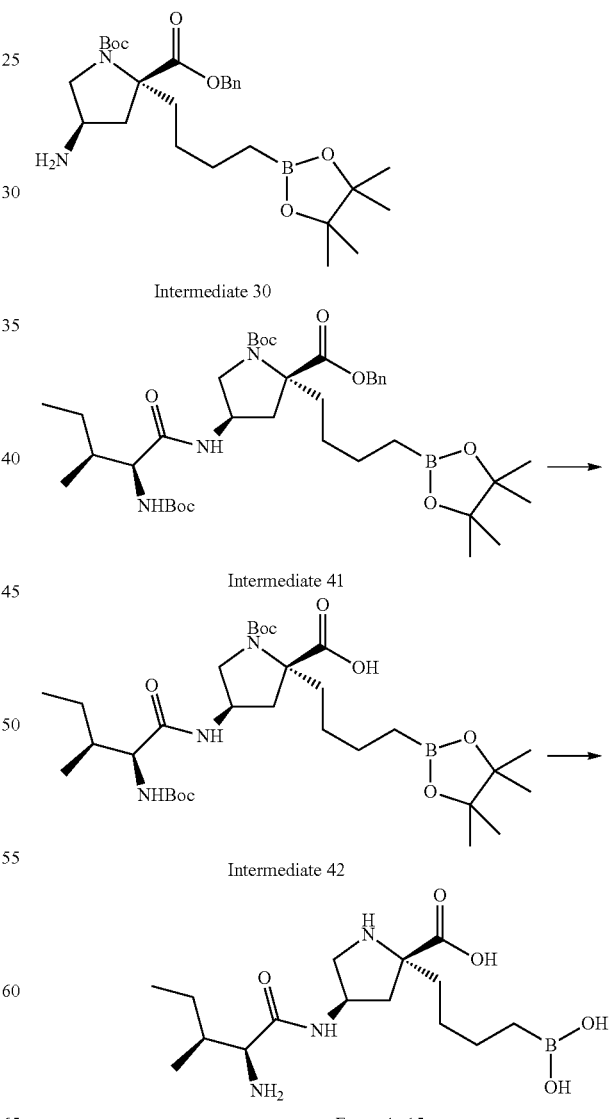

Intermediate 41: (2R,4R)-2-benzyl 1-tert-butyl 44(2S,3S)-2-(tert-butoxycarbonylamino)-3-methylpentanamido)-2-(4-(4,4,5,5-tetramethyl-1,3,2-dioxaborolan-2-yl)butyl)pyrrolidine-1,2-dicarboxylate HATU (804 mg, 2.11 mmol) was added to a solution of Boc-Ile-OH (489 mg, 2.11 mmol) in DMF (4 mL) and the reaction stirred at room temperature for 10 min. (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 885 mg, 1.76 mmol) was added to the reaction mixture as a solution in DMF (3 mL). N,N-Diisopropylethylamine (0.75 mL, 4.3 mmol) was added and the reaction stirred at room temperature overnight. The reaction was then diluted with water (15 mL) and Et$_2$O (10 mL). The layers were separated and the aqueous layer was extracted with Et$_2$O (2×10 mL). The combined organic layers were washed with 5% aqueous lithium chloride (10 mL), dried over MgSO$_4$, filtered, and concentrated to dryness. The crude material was purified by silica gel chromatography (hexanes/EtOAc) to afford (2R,4R)-2-benzyl 1-tert-butyl 4-((2S,3S)-2-(tert-butoxycarbonylamino)-3-methylpentanamido)-2-(4-(4,4,5,5-tetramethyl-1,3,2-dioxaborolan-2-yl)butyl)pyrrolidine-1,2-dicarboxylate (Intermediate 41, 707 mg, 56% yield) as a white solid. $^1$H NMR (500 MHz, CDCl$_3$) δ 0.79 (2H, br t), 0.83-1.05 (8H, m), 1.12-1.21 (1H, m), 1.24 (12H, s), 1.32-1.61 (20H, m), 1.62-2.02 (4H, m), 2.18-2.55 (2H, m), 3.49-3.65 (1H, m), 3.65-3.78 (1H, m), 3.90 (1H, br s), 4.53-4.72 (1H, m), 4.95 (1H, br s), 5.07-5.43 (2H, m), 7.16 (1H, br d), 7.30-7.44 (5H, m). m/z (ES$^+$) [M+H]$^+$=716.

Intermediate 42: (2R,4R)-1-(tert-butoxycarbonyl)-4-((2S,3S)-2-(tert-butoxycarbonylamino)-3-methylpentanamido)-2-(4-(4,4,5,5-tetramethyl-1,3,2-dioxaborolan-2-yl)butyl)pyrrolidine-2-carboxylic acid (2R,4R)-2-benzyl 1-tert-butyl 4-((2S,3S)-2-(tert-butoxycarbonylamino)-3-methylpentanamido)-2-(4-(4,4,5,5-tetramethyl-1,3,2-dioxaborolan-2-yl)butyl)pyrrolidine-1,2-dicarboxylate (Intermediate 41, 707 mg, 0.99 mmol) was dissolved in EtOAc (10 mL) and treated with Pd/C (10 wt %, 105 mg, 0.10 mmol). The flask was equipped with a balloon of H$_2$ and the suspension stirred overnight at room temperature. The reaction mixture was filtered through diatomaceous earth and rinsed with EtOAc and methanol. The filtrate was concentrated to dryness to afford (2R,4R)-1-(tert-butoxycarbonyl)-4-((2S,3S)-2-(tert-butoxycarbonylamino)-3-methylpentanamido)-2-(4-(4,4,5,5-tetramethyl-1,3,2-dioxaborolan-2-yl)butyl)pyrrolidine-2-carboxylic acid (Intermediate 42, 603 mg, 98% yield) which was used without further purification. $^1$H NMR (500 MHz, CDCl$_3$) δ 0.68-0.80 (2H, m), 0.83-0.93 (6H, m), 1.05-1.14 (1H, m), 1.21 (12H, s), 1.28-1.36 (1H, m), 1.37-1.55 (22H, m), 1.71-1.96 (2H, m), 2.18-2.31 (1H, m), 2.72 (1H, br d), 3.42-3.51 (2H, m), 3.52-3.63 (1H, m), 3.86-4.04 (1H, m), 4.16-4.34 (1H, m), 4.98 (1H, br d), 6.69 (1H, br s); m/z (ES$^+$) [M+H]$^+$=626.

Example 15: (2R,4R)-4-((2S,3S)-2-amino-3-methylpentanamido)-2-(4-boronobutyl)pyrrolidine-2-carboxylic acid Trifluoroacetic acid (1.10 mL, 14.3 mmol) was added to a solution of (2R,4R)-1-(tert-butoxycarbonyl)-4-((2S,3S)-2-(tert-butoxycarbonylamino)-3-methylpentanamido)-2-(4-(4,4,5,5-tetramethyl-1,3,2-dioxaborolan-2-yl)butyl)pyrrolidine-2-carboxylic acid (Intermediate 42, 603 mg, 0.96 mmol) in DCM (6 mL). The resulting solution stirred at room temperature for 16 h and was then concentrated under vacuum. The crude amino acid was dissolved in Et$_2$O (10 mL) and reconcentrated under vacuum. This redissolution and reconcentration process was repeated twice more. The crude amino acid was then dissolved in Et$_2$O (6 mL) and 1 M HCl aq (6 mL). Phenylboronic acid (235 mg, 1.93 mmol) was added and the clear biphasic solution stirred at room temperature for 3 h. The reaction mixture was diluted with water and washed with Et$_2$O. The aqueous layer was lyophilized and purified by ion exchange chromatography (Silicycle SiliaSep SPE-R51230B-20X 5 g column). The desired product was eluted from the column using a 5% ammonia in MeOH solution. The obtained material was further purified by reverse phase chromatography (RediSep Rf Gold® C18Aq, 0 to 25% acetonitrile in water) to afford (2R,4R)-4-((2S,3S)-2-amino-3-methylpentanamido)-2-(4-boronobutyl)pyrrolidine-2-carboxylic acid (Example 15, 136 mg, 41% yield) as a white solid. $^1$H NMR (500 MHz, D$_2$O) δ 0.55-0.81 (2H, m), 0.89 (6H, dd), 1.07-1.52 (6H, m), 1.63-1.83 (2H, m), 1.86-2.09 (1H, m), 2.13-2.51 (2H, m), 3.11-3.40 (2H, m), 3.45-3.67 (1H, m), 4.39-4.54 (1H, m); m/z (ES$^+$) [M+H]$^+$=344.

Example 16: (2R,4R)-4-((S)-2-amino-4-methylpentanamido)-2-(4-boronobutyl)pyrrolidine-2-carboxylic acid

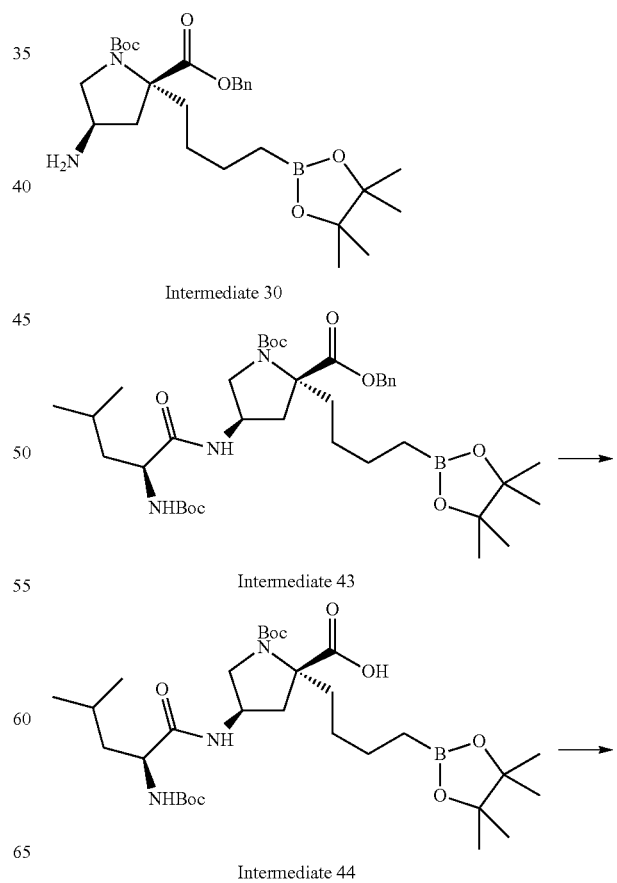

Intermediate 30

Intermediate 43

Intermediate 44

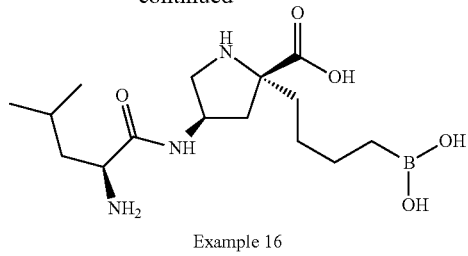

Example 16

Intermediate 43: (2R,4R)-2-benzyl 1-tert-butyl 4-((S)-2-(tert-butoxycarbonylamino)-4-methylpentanamido)-2-(4-(4,4,5,5-tetramethyl-1,3,2-dioxaborolan-2-yl)butyl)pyrrolidine-1,2-dicarboxylate HATU (247 mg, 0.65 mmol) was added to a solution of Boc-Leu-OH (125 mg, 0.54 mmol) in DCM (2 mL) and the reaction stirred at room temperature for 10 min. (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 272 mg, 0.54 mmol) was added to the reaction mixture as a solution in DCM (2 mL). N,N-Diisopropylethylamine (0.19 mL, 1.1 mmol) was added and the reaction stirred at room temperature for 1 h. The reaction was then diluted with DCM (20 mL) and washed sequentially with water (25 mL) and saturated aqueous sodium chloride (30 mL). The organic layer was dried over MgSO$_4$, filtered and concentrated to dryness. The crude material was purified by silica gel chromatography (hexanes/EtOAc) to afford (2R,4R)-2-benzyl 1-tert-butyl 4-((S)-2-(tert-butoxycarbonylamino)-4-methylpentanamido)-2-(4-(4,4,5,5-tetramethyl-1,3,2-dioxaborolan-2-yl)butyl)pyrrolidine-1,2-dicarboxylate (Intermediate 43, 210 mg, 54% yield) as a colorless foam and as a mixture of rotamers. $^1$H NMR (500 MHz, CDCl$_3$) δ 0.77 (2H, t), 0.91 (6H, d), 1.06-1.19 (1H, m), 1.19-1.24 (12H, m), 1.31-1.51 (20H, m), 1.50-1.63 (2H, m), 1.73-2.02 (2H, m), 2.17-2.55 (2H, m), 3.35-3.75 (2H, m), 3.84-4.06 (1H, m), 4.35-4.75 (2H, m), 5.00-5.46 (2H, m), 7.08-7.22 (1H, m), 7.28-7.42 (5H, m); m/z (ES$^+$) [M+H]$^+$=716.

Intermediate 44: (2R,4R)-1-(tert-butoxycarbonyl)-4-((S)-2-(tert-butoxycarbonylamino)-4-methylpentanamido)-2-(4-(4,4,5,5-tetramethyl-1,3,2-dioxaborolan-2-yl)butyl)pyrrolidine-2-carboxylic acid (2R,4R)-2-benzyl 1-tert-butyl 4-((S)-2-(tert-butoxycarbonylamino)-4-methylpentanamido)-2-(4-(4,4,5,5-tetramethyl-1,3,2-dioxaborolan-2-yl)butyl)pyrrolidine-1,2-dicarboxylate (Intermediate 43, 201 mg, 0.28 mmol) was dissolved in EtOAc (4 mL) and treated with Pd/C (10 wt %, 100 mg, 0.094 mmol). The flask was equipped with a balloon of H$_2$ and the suspension stirred at room temperature for 2 h. The reaction mixture was filtered through diatomaceous earth and rinsed with EtOAc and methanol. The filtrate was concentrated to dryness to afford (2R,4R)-1-(tert-butoxycarbonyl)-4-((S)-2-(tert-butoxycarbonylamino)-4-methylpentanamido)-2-(4-(4,4,5,5-tetramethyl-1,3,2-dioxaborolan-2-yl)butyl)pyrrolidine-2-carboxylic acid (Intermediate 44, 170 mg, 97% yield) as a white solid and as a mixture of rotamers. $^1$H NMR (500 MHz, CDCl$_3$) δ 0.78 (2H, t), 0.93 (6H, d), 1.15-1.25 (12H, m), 1.25-1.31 (2H, m), 1.39-1.51 (19H, m), 1.55-1.72 (2H, m), 1.73-1.89 (1H, m), 2.01-2.11 (1H, m), 2.18-2.36 (1H, m), 2.47-2.83 (1H, m), 3.37-3.74 (2H, m), 3.96-4.10 (1H, m), 4.17-4.32 (1H, m), 4.82-5.31 (1H, m), 6.62-7.12 (1H, m); m/z (ES$^+$) [M+H]$^+$=626.

Example 16: (2R,4R)-4-((S)-2-amino-4-methylpentanamido)-2-(4-boronobutyl)pyrrolidine-2-carboxylic acid Trifluoroacetic acid (1.00 mL, 13.0 mmol) was added to a solution of (2R,4R)-1-(tert-butoxycarbonyl)-4-((S)-2-(tert-butoxycarbonylamino)-4-methylpentanamido)-2-(4-(4,4,5,5-tetramethyl-1,3,2-dioxaborolan-2-yl)butyl)pyrrolidine-2-carboxylic acid (Intermediate 44, 170 mg, 0.27 mmol) in DCM (2 mL). The resulting solution stirred at room temperature for 2 h and was then concentrated under vacuum. The crude amino acid was then dissolved in Et$_2$O (5 mL) and water (4 mL). Phenylboronic acid (66 mg, 0.54 mmol) was added and the clear biphasic solution stirred at room temperature for 2 h. The reaction mixture was diluted with water (5 mL) and Et$_2$O (20 mL) and the layers were separated. The aqueous layer was lyophilized and purified by ion exchange chromatography (PoraPak Rxn CX 2 g column) to afford (2R,4R)-4-((S)-2-amino-4-methylpentanamido)-2-(4-boronobutyl)pyrrolidine-2-carboxylic acid (Example 16, 88 mg, 94% yield) as a white solid. $^1$H NMR (500 MHz, D$_2$O) δ 0.46-0.68 (2H, m), 0.73-0.82 (6H, m), 1.03-1.13 (1H, m), 1.13-1.23 (1H, m), 1.23-1.42 (4H, m), 1.42-1.52 (1H, m), 1.54-1.66 (1H, m), 1.76-1.93 (1H, m), 2.07-2.19 (1H, m), 2.29 (1H, dd), 3.13 (1H, q), 3.34 (1H, t), 3.48 (1H, q), 4.23-4.40 (1H, m); m/z (ES$^+$) [M+H]$^+$=344.

Example 17: (2R,4R)-4-((S)-2-amino-3-hydroxypropanamido)-2-(4-boronobutyl)pyrrolidine-2-carboxylic acid

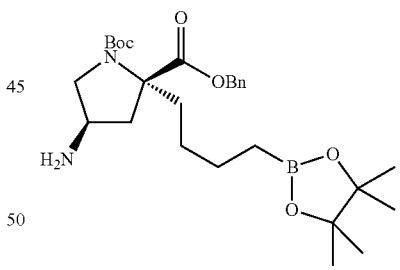

Intermediate 30

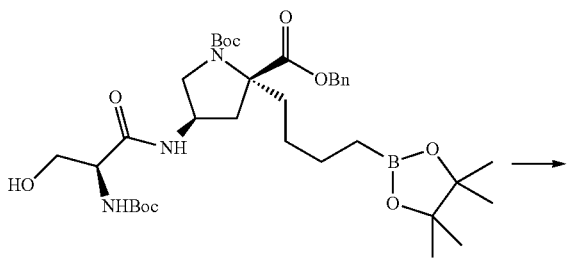

Intermediate 45

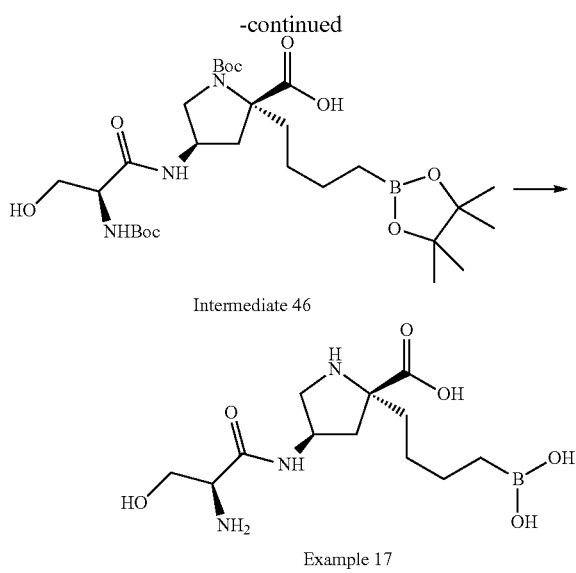

Intermediate 46

Example 17

Intermediate 45: (2R,4R)-2-benzyl 1-tert-butyl 4-((S)-2-(tert-butoxycarbonylamino)-3-hydroxypropanamido)-2-(4-(4,4,5,5-tetramethyl-1,3,2-dioxaborolan-2-yl)butyl)pyrrolidine-1,2-dicarboxylate N,N-Diisopropylethylamine (0.108 mL, 0.62 mmol) was added to a stirred solution of COMU (292 mg, 0.68 mmol), (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 311 mg, 0.62 mmol) and Boc-Ser-OH (133 mg, 0.65 mmol) in DMF (5 mL) at room temperature. The reaction was stirred for 3 h, diluted with water (80 mL) and EtOAc (15 mL). The phases were separated and the aqueous phase was further diluted with saturated aqueous NaHCO$_3$ then extracted with EtOAc (2×20 mL). The combined organics were washed with saturated aqueous NaCl (2×10 mL), dried over MgSO$_4$, filtered and concentrated to dryness. The crude material was purified by silica gel chromatography (hexanes/EtOAc) to afford (2R,4R)-2-benzyl 1-tert-butyl 4-((S)-2-(tert-butoxycarbonylamino)-3-hydroxypropanamido)-2-(4-(4,4,5,5-tetramethyl-1,3,2-dioxaborolan-2-yl)butyl)pyrrolidine-1,2-dicarboxylate (Intermediate 45, 358 mg, 84% yield) as colorless dry film and as a mixture of rotamers. $^1$H NMR (500 MHz, CDCl$_3$) δ 0.76 (2H, t), 1.16 (1H, m), 1.21 (12H, s), 1.31 (6H, s), 1.35-1.42 (5H, m), 1.43 (11H, s), 1.73-1.87 (1H, m), 1.87-2.02 (2H, m), 2.14-2.24 (1H, m), 2.29-2.41 (1H, m), 3.43-3.52 (0.4H, m), 3.52-3.61 (2H, m), 3.66 (0.6H, d), 3.79-3.92 (1H, m), 3.92-4.04 (1H, m), 4.51 (1H, br s), 5.06-5.26 (2H, m), 5.36 (1H, br s), 7.30-7.40 (5H, m); m/z (ES$^+$) [M+H]$^+$=690.

Intermediate 46: (2R,4R)-1-(tert-butoxycarbonyl)-4-((S)-2-(tert-butoxycarbonylamino)-3-hydroxypropanamido)-2-(4-(4,4,5,5-tetramethyl-1,3,2-dioxaborolan-2-yl)butyl)pyrrolidine-2-carboxylic acid (2R,4R)-2-benzyl 1-tert-butyl 4-((S)-2-(tert-butoxycarbonylamino)-3-hydroxypropanamido)-2-(4-(4,4,5,5-tetramethyl-1,3,2-dioxaborolan-2-yl)butyl)pyrrolidine-1,2-dicarboxylate (Intermediate 45, 358 mg, 0.52 mmol) was dissolved in EtOAc (4 mL) and treated with Pd/C (10 wt %, 50 mg, 0.047 mmol). The flask was equipped with a balloon of H$_2$ and the suspension stirred at room temperature for 3.5 h. The reaction mixture was diluted with MeOH, filtered through diatomaceous earth concentrated to dryness to afford (2R,4R)-1-(tert-butoxycarbonyl)-4-((S)-2-(tert-butoxycarbonylamino)-3-hydroxypropanamido)-2-(4-(4,4,5,5-tetramethyl-1,3,2-dioxaborolan-2-yl)butyl)pyrrolidine-2-carboxylic acid (Intermediate 46, 303 mg, 97% yield) as a white solid and as a mixture of rotamers, which was used without further purification. $^1$H NMR (500 MHz, CD$_2$Cl$_2$) δ 0.67-0.91 (2H, m), 1.25 (14H, s), 1.41-1.47 (3H, m), 1.48 (9H, s), 1.53 (10H, s), 1.82-1.90 (2H, m), 2.06-2.14 (1H, m), 2.24-2.33 (1H, m), 2.76-2.91 (1H, m), 3.48-3.54 (1H, m), 3.59 (1H, dd), 3.70 (1H, dd), 3.93 (1H, d), 4.03-4.17 (1H, m), 4.29 (1H, d), 6.79-6.98 (1H, m); m/z (ES$^+$) [M+H]$^+$=600.

Example 17: (2R,4R)-4-((S)-2-amino-3-hydroxypropanamido)-2-(4-boronobutyl)pyrrolidine-2-carboxylic acid Trifluoroacetic acid (0.771 mL, 10.01 mmol) was added dropwise to a stirred solution of (2R,4R)-1-(tert-butoxycarbonyl)-4-((S)-2-(tert-butoxycarbonylamino)-3-hydroxypropanamido)-2-(4-(4,4,5,5-tetramethyl-1,3,2-dioxaborolan-2-yl)butyl)pyrrolidine-2-carboxylic acid (Intermediate 46, 300 mg, 0.50 mmol) in DCM (4 mL) at room temperature. After 1.5 h the solution was concentrated under reduced pressure and the resultant residue was dissolved in 1 M HCl aq (4 mL, 4.00 mmol) and Et$_2$O (4 mL). Phenylboronic acid (183 mg, 1.50 mmol) was added and the clear biphasic solution stirred at room temperature for 3 h. The mixture was diluted with Et$_2$O (20 mL) and water (5 mL) and the layers were separated. The aqueous layer was washed with Et$_2$O, the layers were separated and the aqueous layer was lyophilized. The resulting solid was dissolved in MeOH (3 mL) and subject to ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 0 to 30% acetonitrile in water) to afford (2R,4R)-4-((S)-2-amino-3-hydroxypropanamido)-2-(4-boronobutyl)pyrrolidine-2-carboxylic acid (Example 17, 94 mg, 59% yield) as a white solid. $^1$H NMR (500 MHz, D$_2$O) δ 0.77 (2H, td), 1.16-1.26 (1H, m), 1.26-1.35 (1H, m), 1.35-1.45 (2H, m), 1.76 (1H, ddd), 2.02 (1H, ddd), 2.29 (1H, dd), 2.46 (1H, dd), 3.35 (1H, dd), 3.48 (1H, t), 3.62 (1H, dd), 3.66-3.77 (2H, m), 4.40-4.50 (1H, m); m/z (ES$^+$) [M+H]$^+$=318.

Example 18: (2R,4R)-4-((S)-2-amino-3-methoxypropanamido)-2-(4-boronobutyl)pyrrolidine-2-carboxylic acid

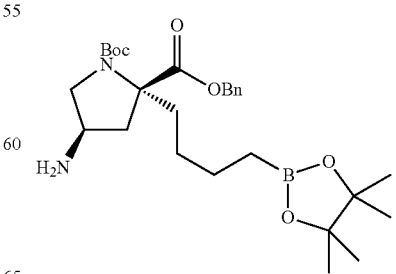

Intermediate 30

77

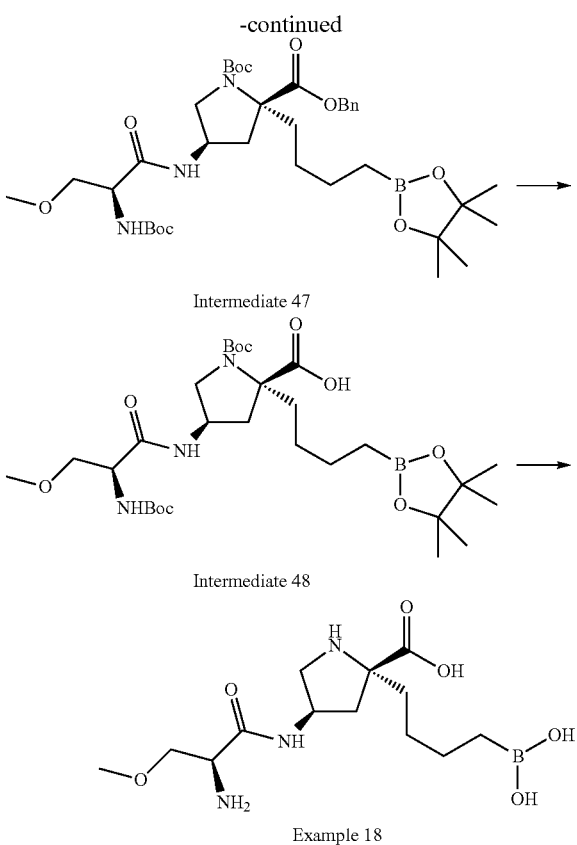

Intermediate 47

Intermediate 48

Example 18

Intermediate 47: (2R,4R)-2-benzyl 1-tert-butyl 4-((S)-2-(tert-butoxycarbonylamino)-3-methoxypropanamido)-2-(4-(4,4,5,5-tetramethyl-1,3,2-dioxaborolan-2-yl)butyl)pyrrolidine-1,2-dicarboxylate N,N-Diisopropylethylamine (0.082 mL, 0.47 mmol) was added to a stirred solution of COMU (220 mg, 0.51 mmol), (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 235 mg, 0.47 mmol) and N-Boc-O-methyl-L-serine (108 mg, 0.49 mmol) in DMF (3 mL) at room temperature. The reaction was stirred for 2 h then diluted with water (60 mL) and DCM (15 mL). The phases were separated and the aqueous phase was extracted with DCM (2×20 mL). The combined organics were washed with saturated aqueous NaHCO$_3$ (30 mL), saturated aqueous NaCl (2×10 mL), dried over MgSO$_4$, filtered and concentrated under reduced pressure. The resulting residue was purified by silica gel chromatography (hexanes/EtOAc) to afford (2R,4R)-2-benzyl 1-tert-butyl 4-((S)-2-(tert-butoxycarbonylamino)-3-methoxypropanamido)-2-(4-(4,4,5,5-tetramethyl-1,3,2-dioxaborolan-2-yl)butyl)pyrrolidine-1,2-dicarboxylate (Intermediate 47, 145 mg, 44% yield) as colorless dry film and as a mixture of rotamers. $^1$H NMR (500 MHz, CDCl$_3$) δ 0.78 (2H, t), 1.18 (1H, br dd), 1.22-1.26 (13H, m), 1.33 (6H, s), 1.44 (5H, br s), 1.46 (9H, s), 1.57-1.74 (1H, m), 1.74-1.85 (1H, m), 1.94 (0.4H, d), 2.01 (0.6H, d), 2.18-2.27 (0.6H, m), 2.32-2.47 (1.4H, m), 3.32 (3H, s), 3.39-3.46 (1H, m), 3.49-3.55 (0.4H, m), 3.60 (1H, dd), 3.65-3.76 (1.6H, m), 4.15 (1H, br d), 4.51-4.64 (1H, m), 5.06-5.22 (2H, m), 5.23-5.34 (1H, m), 7.32-7.39 (5H, m); m/z (ES$^+$) [M+H]$^+$=704.

Intermediate 48: (2R,4R)-1-(tert-butoxycarbonyl)-4-((S)-2-(tert-butoxycarbonylamino)-3-methoxypropanamido)-2-(4-(4,4,5,5-tetramethyl-1,3,2-dioxaborolan-2-yl)butyl)pyrrolidine-2-carboxylic acid (2R,4R)-2-benzyl 1-tert-butyl 4-((S)-2-(tert-butoxycarbonylamino)-3-methoxypropanamido)-2-(4-(4,4,5,5-tetramethyl-1,3,2-dioxaborolan-2-yl)butyl)pyrrolidine-1,2-dicarboxylate (Intermediate 47, 145 mg, 0.21 mmol) was dissolved in EtOAc (2 mL) and treated with Pd/C (10 wt %, 22 mg, 0.021 mmol). The flask was equipped with a balloon of H$_2$ and the suspension stirred at room temperature for 4 h. The reaction mixture was diluted with MeOH, filtered through diatomaceous earth concentrated to dryness to afford (2R,4R)-1-(tert-butoxycarbonyl)-4-((S)-2-(tert-butoxycarbonylamino)-3-methoxypropanamido)-2-(4-(4,4,5,5-tetramethyl-1,3,2-dioxaborolan-2-yl)butyl)pyrrolidine-2-carboxylic acid (Intermediate 48, 126 mg, 100% yield) as a white solid and as a mixture of rotamers, which was used without further purification. $^1$H NMR (500 MHz, CD$_2$Cl$_2$) δ 0.65-0.80 (2H, m), 1.14-1.29 (14H, m), 1.35-1.43 (5H, m), 1.44 (7H, s), 1.46-1.60 (8H, m), 1.77-1.95 (1H, m), 2.03-2.14 (1H, m), 2.14-2.26 (1H, m), 2.68 (1H, br d), 3.33 (3H, s), 3.38-3.47 (1H, m), 3.47-3.60 (2H, m), 3.65-3.76 (1H, m), 4.02-4.15 (1H, m), 4.24 (1H, br s), 5.38 (1H, br s), 7.06 (1H, br s); m/z (ES$^+$) [M+H]$^+$=614.

Example 18: (2R,4R)-4-((S)-2-amino-3-methoxypropanamido)-2-(4-boronobutyl)pyrrolidine-2-carboxylic acid Trifluoroacetic acid (0.25 mL, 3.26 mmol) was added dropwise to a stirred solution of (2R,4R)-1-(tert-butoxycarbonyl)-4-((S)-2-(tert-butoxycarbonylamino)-3-methoxypropanamido)-2-(4-(4,4,5,5-tetramethyl-1,3,2-dioxaborolan-2-yl)butyl)pyrrolidine-2-carboxylic acid (Intermediate 48, 100 mg, 0.16 mmol) in DCM (2 mL) at ambient temperature. After 1 h the solution was concentrated under reduced pressure and the resultant residue was dissolved in 1 M HCl aq (2 mL, 2.00 mmol) and Et$_2$O (2 mL). Phenylboronic acid (60 mg, 0.49 mmol) was added and the clear biphasic solution stirred at room temperature for 3 h. The mixture was diluted with Et$_2$O (20 mL) and water (5 mL) and the layers were separated. The aqueous layer was washed with Et$_2$O, the layers were separated and the aqueous layer was lyophilized. The resulting solid was dissolved in MeOH (3 mL) and subject to ion exchange chromatography (PoraPak Rxn CX 20 cc column). The desired product was eluted from the column using a 5% ammonia in MeOH solution (20 mL). The obtained material was further purified by reverse phase chromatography (RediSep Rf Gold® C18, 0 to 20% acetonitrile in water). The product fractions were lyophilized and the resultant material was again subject to reverse phase flash chromatography (RediSep Rf Gold® C18, 0 to 2% acetonitrile in water). The product fractions were lyophilized and the resultant material was again re-purified by reverse phase flash chromatography (RediSep Rf Gold® C18, 0 to 5% acetonitrile in water) to afford (2R,4R)-4-((S)-2-amino-3-methoxypropanamido)-2-(4-boronobutyl)pyrrolidine-2-carboxylic acid (Example 18, 18 mg, 35% yield) as a white solid. $^1$H NMR (500 MHz, D$_2$O) δ 0.77 (2H, td), 1.14-1.27 (1H, m), 1.27-1.35 (1H, m), 1.35-1.45 (2H, m), 1.72-1.81 (1H, m), 2.02 (1H, ddd), 2.30 (1H, dd), 2.41 (1H, dd), 3.31-3.38 (4H, m), 3.55-3.60 (3H, m), 3.63 (1H, dd), 4.42-4.51 (1H, m); m/z (ES$^+$) [M+H]$^+$=332.

Example 19: (S)-2-amino-N-((3R,5R)-8-hydroxy-6-oxo-7-oxa-1-aza-8-boraspiro[4.7]dodecan-3-yl)-3-methylbutanamide Compound B

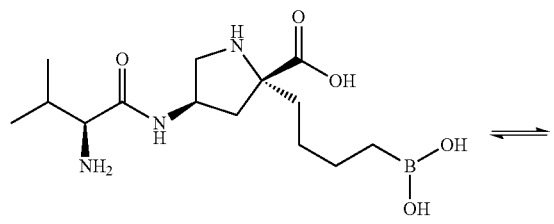

Compound A

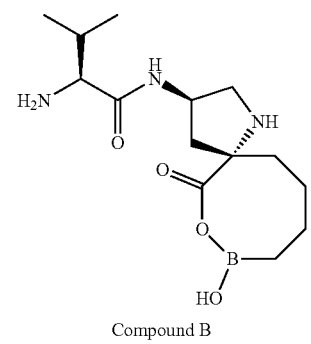

Compound B

Figure 2:
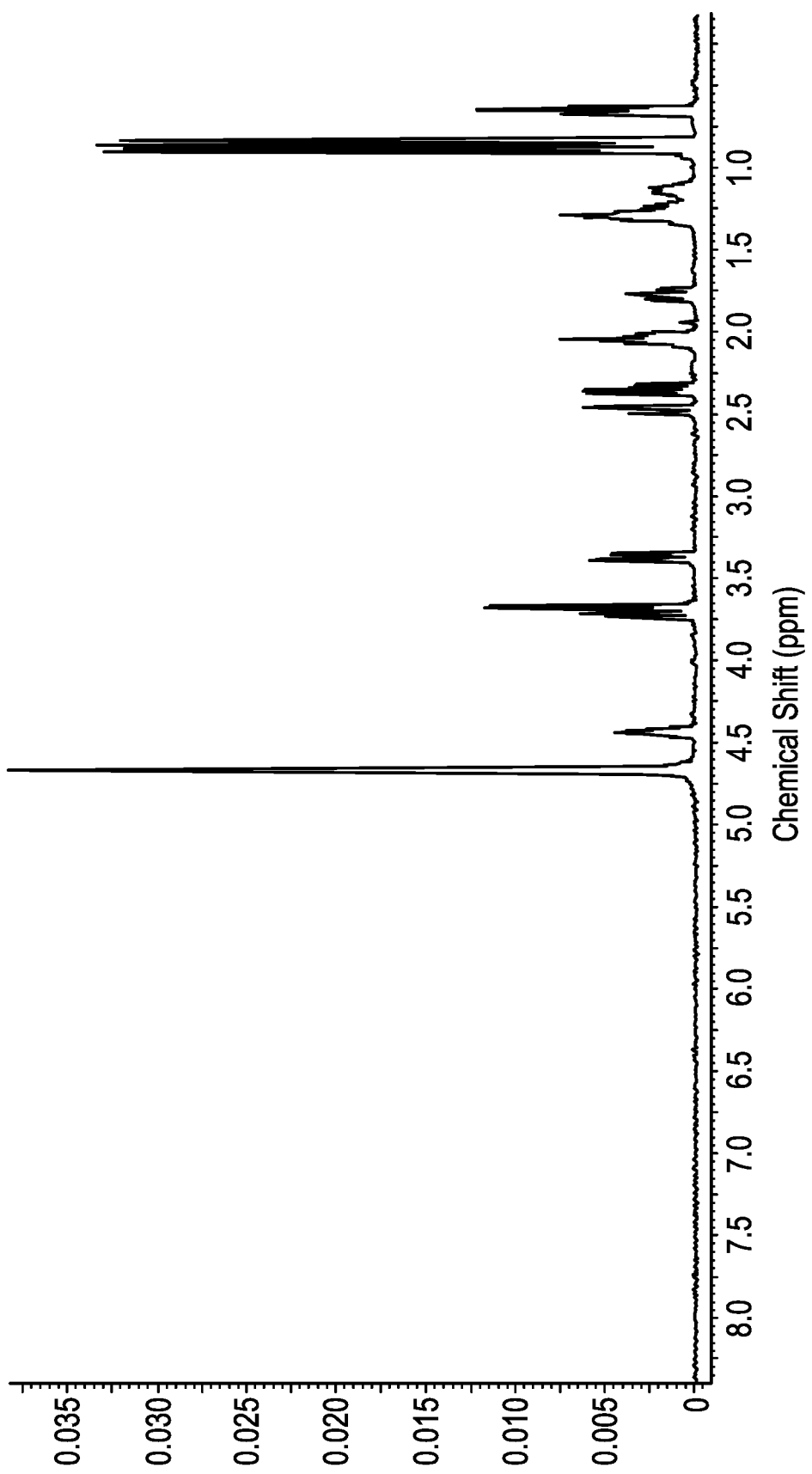
FIG. 2 shows the NMR spectrum (in 0.1 M DCl in $D_2O$) of compound B depicting how acidification yields almost complete conversion to compound A.
Figure 3:
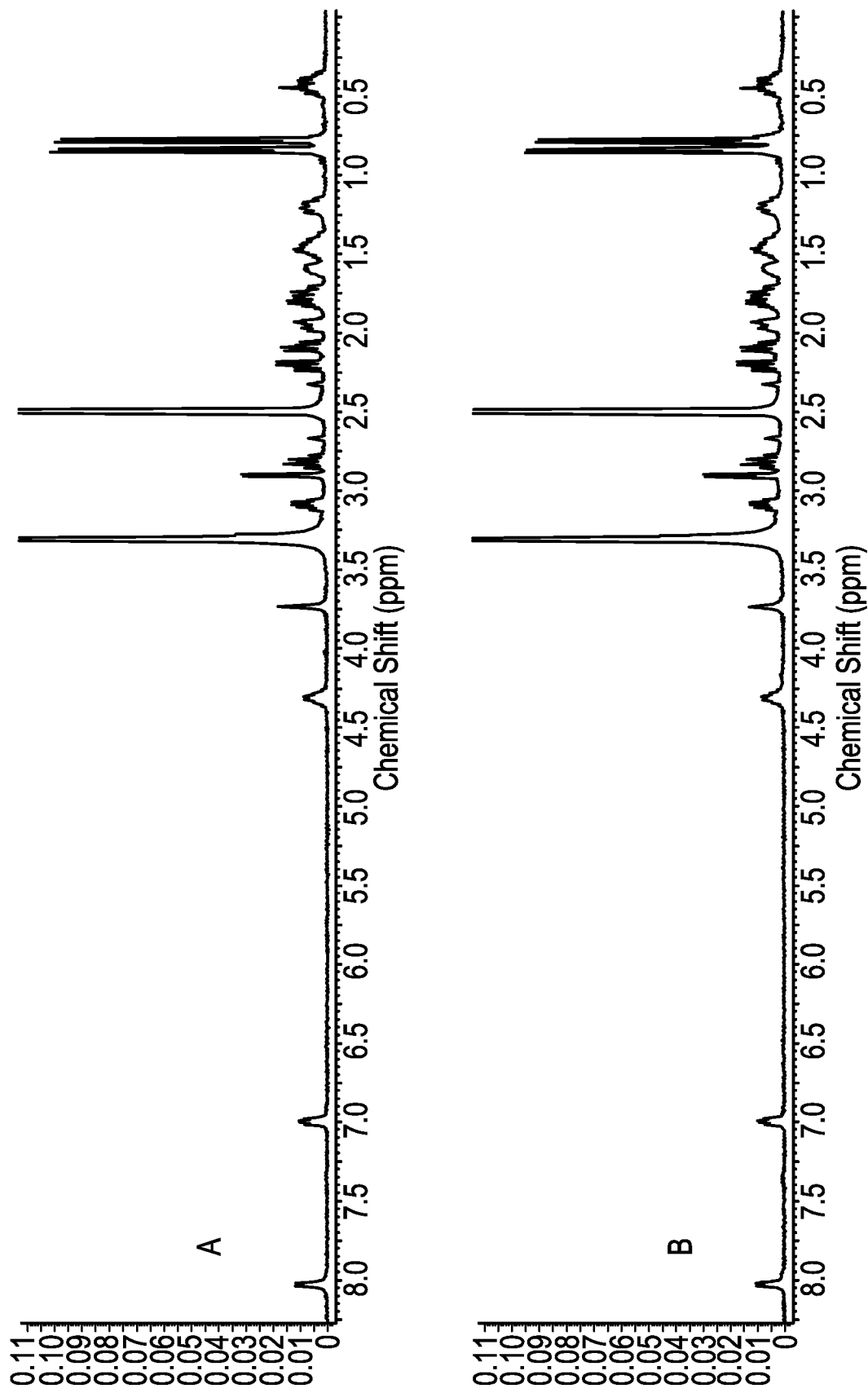
FIG. 3 compares NMR spectra of amorphous material in d6-DMSO (Labeled B) with crystalline compound B in d6-DMSO (Labeled A) showing that both materials have the same cyclic structure as crystalline compound B.

Compound B (Example 19) was obtained by the intramolecular cyclization of Example 9 (Compound A) via an interconversion process. Furthermore, interconversions between Compound A (Example 9) and Compound B were observed under various conditions. For example, Compound B was converted to Compound A in the presence of water and such conversion was proportional to the concentration of water in the solvent. This is demonstrated in FIG. 1 where the NMR spectra of compound B prepared in 100% d6-DMSO (labeled A), 75% D$_2$O in d6-DMSO (labeled B), 50% D$_2$O in d6-DMSO (labeled C), 25% D$_2$O in d6-DMSO (labeled E) and 100% D$_2$O (labeled F) are shown. In d6-DMSO, compound B predominates, while there is a proportional increase in compound A with increase in D$_2$O concentration. The proportion of compound A relative to compound B in 100% D$_2$O reaches approximately 90%. Furthermore, Compound B was converted to Compound A under acidic condition. In FIG. 2, the NMR spectrum of compound B in 0.1 M DCl (in D20) demonstrates that acidification yields almost complete conversion to compound A. In addition, it was determined that crystalline Compound B and amorphous Compound B have the same structural form. In FIG. 3, the NMR spectra (obtained in d6-DMSO) demonstrate that both crystalline Compound B and the amorphous Compound B have the same cyclic structure.

Example 20: (2R,4R)-4-[[(2S)-2-amino-3-hydroxy-3-methyl-butanoyl]amino]-2-(4-boronobutyl)pyrrolidine-2-carboxylic acid

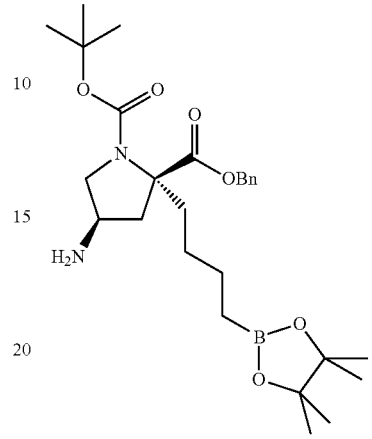

Intermediate 30

Intermediate 52

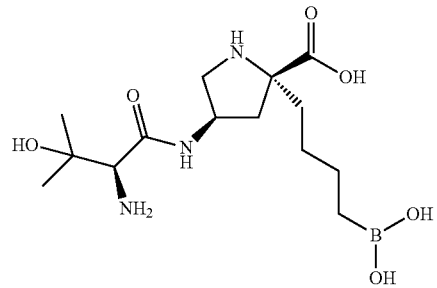

Example 20

Intermediate 52: 2-benzyl 1-(tert-butyl) (2R,4R)-4-((S)-2-((tert-butoxycarbonyl)amino)-3-hydroxy-3-methylbutanamido)-2-(4-(4,4,5,5-tetramethyl-1,3,2-dioxaborolan-2-yl)butyl)pyrrolidine-1,2-dicarboxylate N,N-Diisopropylethylamine (0.13 mL, 0.76 mmol) was added to a solution of (S)—N-alpha-t-Butyloxycarbonyl-3, 3-dimethyl-serine (106 mg, 0.454 mmol) and HATU (0.173 g, 0.454 mmol) in DMF (2.6 mL) at 0° C. and the reaction stirred for 15 min. A solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 190 mg, 0.38 mmol) in DMF (1 mL) was added and the reaction stirred for 2 h while slowly warming to room temperature. The reaction mixture was diluted with EtOAc (40 mL) and washed with saturated aqueous NH$_4$Cl (2×20 mL), saturated aqueous NaHCO$_3$ (2×20 mL) and brine (20 mL). The organic layer was dried over Na$_2$SO$_4$, filtered and concentrated to dryness. The crude material was purified by silica gel chromatography (0-50% EtOAc in hexanes) to afford 2-benzyl 1-(tert-butyl) (2R,4R)-4-((S)-2-((tert-butoxycarbonyl)amino)-3-hydroxy-3-methylbutanamido)-2-(4-(4,4,5,5-tetramethyl-1,3,2-dioxaborolan-2-yl)butyl)pyrrolidine-1,2-dicarboxylate (Intermediate 52, 223 mg, 82% yield) as a white foam and as a mixture of rotamers. $^1$H NMR (500 MHz, MeOH-d$_4$) δ 0.70-0.83 (m, 2H) 1.14-1.27 (m, 19H) 1.31 (s, 6H) 1.36-1.42 (m, 5H) 1.44 (s, 10H) 1.81-1.93 (m, 1H) 2.02-2.14 (m, 1H) 2.14-2.30 (m, 1H) 2.36-2.49 (m, 1H) 3.39-3.48 (m, 1H) 3.73-3.83 (m, 1H) 3.87-3.97 (m, 1H) 4.43-4.53 (m, 1H) 5.09-5.25 (m, 2H) 7.28-7.45 (m, 5H); m/z (ES$^+$) [M+H]$^+$=718.

Example 20: (2R,4R)-4-[[(2S)-2-amino-3-hydroxy-3-methyl-butanoyl]amino]-2-(4-boronobutyl)pyrrolidine-2-carboxylic acid Pd/C (10% wt, 100 mg, 0.09 mmol) was added to a solution of 2-benzyl 1-(tert-butyl) (2R,4R)-4-((S)-2-((tert-butoxycarbonyl)amino)-3-hydroxy-3-methylbutanamido)-2-(4-(4,4,5,5-tetramethyl-1,3,2-dioxaborolan-2-yl)butyl) pyrrolidine-1,2-dicarboxylate (Intermediate 52, 220 mg, 0.31 mmol) in EtOAc (3 mL). The flask was equipped with a balloon of H$_2$ and the suspension stirred at room temperature for 3 h. The reaction mixture was diluted with MeOH, filtered through diatomaceous earth and concentrated to dryness. The white solid was dissolved in DCM (1 mL) and trifluoroacetic acid (0.50 mL, 6.5 mmol) and the reaction stirred at room temperature for 2 h. The solution was concentrated, and the resulting residue was dissolved in Et$_2$O (2 mL) and 1 M HCl aq (2 mL). Phenylboronic acid (100 mg, 0.82 mmol) was added and the clear biphasic solution stirred at room temperature for 2 h. The reaction mixture was diluted with water and washed with Et$_2$O. The aqueous layer was lyophilized and purified by ion exchange chromatography (PoraPak Rxn CX 20 cc column). The desired product was eluted from the column using 5% ammonia in MeOH (20 mL) to afford (2R,4R)-4-[[(2S)-2-amino-3-hydroxy-3-methyl-butanoyl]amino]-2-(4-boronobutyl)pyrrolidine-2-carboxylic acid (Example 20, 92 mg, 87% yield) as a white solid. $^1$H NMR (500 MHz, D$_2$O) δ 0.70 (2H, t), 1.20 (4H, s), 1.28 (4H, s), 1.31-1.40 (2H, m), 1.77-1.88 (1H, m), 2.04-2.14 (1H, m), 2.40-2.47 (1H, m), 2.48-2.54 (1H, m), 3.40 (1H, dd), 3.74 (1H, s), 3.75-3.80 (1H, m), 4.47-4.55 (1H, m); m/z: (ES$^+$) [M+H]$^+$=346.

Example 21: (2R,4R)-4-[[(2S)-2-amino-2,3-dimethyl-butanoyl]amino]-2-(4-boronobutyl)pyrrolidine-2-carboxylic acid

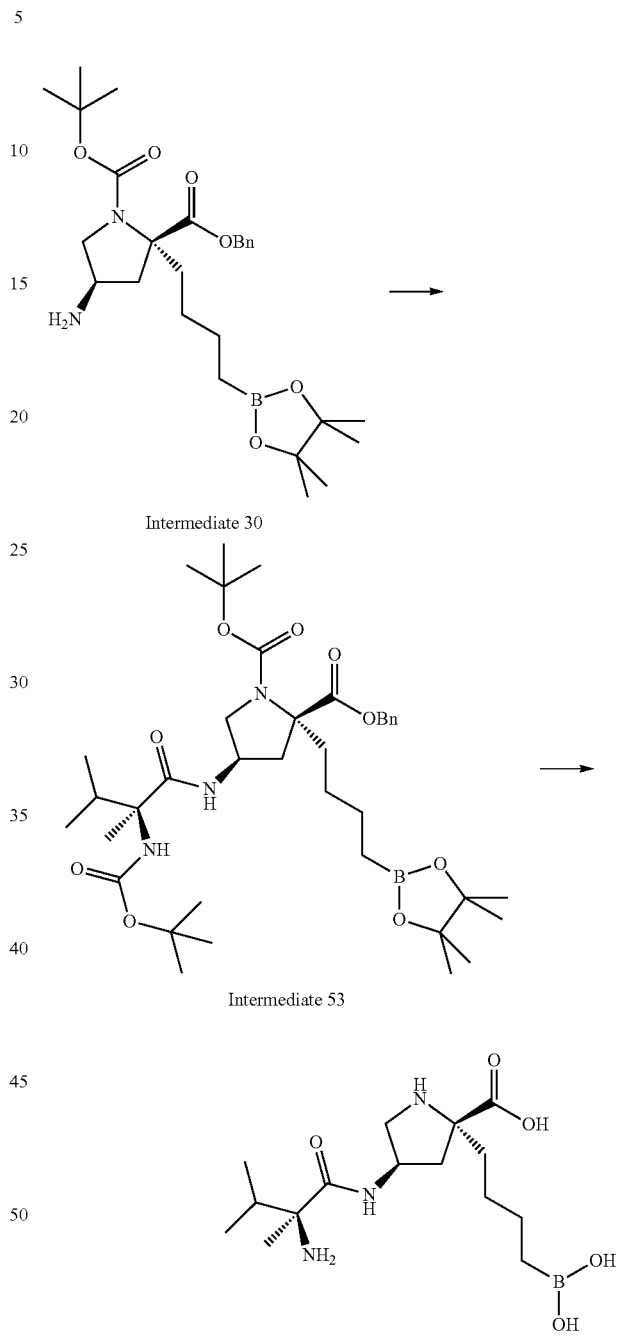

Intermediate 30

Intermediate 53

Example 21

Intermediate 53: 2-benzyl 1-tert-butyl (2R,4R)-4-[[(2S)-2-(tert-butoxycarbonylamino)-2,3-dimethyl-butanoyl]amino]-2-[4-(4,4,5,5-tetramethyl-1,3,2-dioxaborolan-2-yl)butyl]pyrrolidine-1,2-dicarboxylate N,N-Diisopropylethylamine (0.14 mL, 0.82 mmol) was added to a solution of (S)-2-((tert-butoxycarbonyl)amino)-

2,3-dimethylbutanoic acid (0.113 g, 0.489 mmol) and HATU (0.186 g, 0.489 mmol) in DMF (3 mL) at 0° C. and the reaction stirred for 15 min. A solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 205 mg, 0.408 mmol) in DMF (1 mL) was added and the reaction stirred for 3 h while slowly warming to room temperature. The reaction mixture was diluted with EtOAc (50 mL) and washed with saturated aqueous NH$_4$Cl (2×25 mL), saturated aqueous NaHCO$_3$ (2×25 mL) and brine (20 mL). The organic layer was dried over Na$_2$SO$_4$, filtered and concentrated to dryness. The crude material was purified by silica gel chromatography (0-50% EtOAc in hexanes) to afford 2-benzyl 1-tert-butyl (2R,4R)-4-[[(2S)-2-(tert-butoxycarbonylamino)-2,3-dimethyl-butanoyl]amino]-2-[4-(4,4,5,5-tetramethyl-1,3,2-dioxaborolan-2-yl)butyl]pyrrolidine-1,2-dicarboxylate (Intermediate 53, 211 mg, 72% yield) as a white foam and as a mixture of rotamers. $^1$H NMR (500 MHz, MeOH-d$_4$) δ 0.72-0.79 (2H, m), 0.80-0.93 (6H, m), 1.17-1.25 (13H, m), 1.31 (9H, d), 1.36-1.47 (16H, m), 1.82-1.92 (2H, m), 1.97-2.09 (1H, m), 2.15-2.30 (1H, m), 2.34-2.51 (1H, m), 3.61-3.75 (1H, m), 4.42-4.56 (1H, m), 5.08-5.31 (2H, m), 7.29-7.46 (5H, m); m/z: (ES$^+$) [M+H]$^+$=716.

Example 21: (2R,4R)-4-[[(2S)-2-amino-2,3-dimethyl-butanoyl]amino]-2-(4-boronobutyl)pyrrolidine-2-carboxylic acid Pd/C (10% wt, 90 mg, 0.08 mmol) was added to a solution of 2-benzyl 1-tert-butyl (2R,4R)-4-[[(2S)-2-(tert-butoxycarbonylamino)-2,3-dimethyl-butanoyl]amino]-2-[4-(4,4,5,5-tetramethyl-1,3,2-dioxaborolan-2-yl)butyl]pyrrolidine-1,2-dicarboxylate (Intermediate 53, 210 mg, 0.29 mmol) in EtOAc (4 mL). The flask was equipped with a balloon of H$_2$ and the suspension stirred at room temperature for 3 h. The reaction mixture was diluted with MeOH, filtered through diatomaceous earth and concentrated to dryness. The white solid was dissolved in DCM (1 mL) and trifluoroacetic acid (0.50 mL, 6.5 mmol) and the reaction stirred at room temperature for 2 h. The solution was concentrated, and the resulting residue was dissolved in Et$_2$O (2 mL) and 1 M HCl aq (2 mL). Phenylboronic acid (100 mg, 0.82 mmol) was added and the clear biphasic solution stirred at room temperature for 2 h. The reaction mixture was diluted with water and washed with Et$_2$O. The aqueous layer was lyophilized and purified by ion exchange chromatography (PoraPak Rxn CX 20 cc column). The desired product was eluted from the column using 5% ammonia in MeOH (20 mL) to afford (2R,4R)-4-[[(2S)-2-amino-2,3-dimethyl-butanoyl]amino]-2-(4-boronobutyl)pyrrolidine-2-carboxylic acid (Example 21, 90 mg, 89% yield) as a white solid. $^1$H NMR (500 MHz, D$_2$O) δ 0.74-0.78 (2H, m), 0.79 (3H, d), 0.89 (3H, d), 1.17-1.27 (4H, m), 1.28-1.35 (1H, m), 1.36-1.47 (2H, m), 1.70-1.81 (1H, m), 1.93-2.07 (2H, m), 2.27 (1H, dd), 2.43 (1H, dd), 3.27-3.39 (1H, m), 3.60 (1H, dd), 4.39-4.48 (1H, m); m/z: (ES$^+$) [M+H]$^+$=344.

Example 22: (2R,4R)-2-(4-boronobutyl)-4-[[(2S)-2,3-diaminopropanoyl]amino]pyrrolidine-2-carboxylic acid

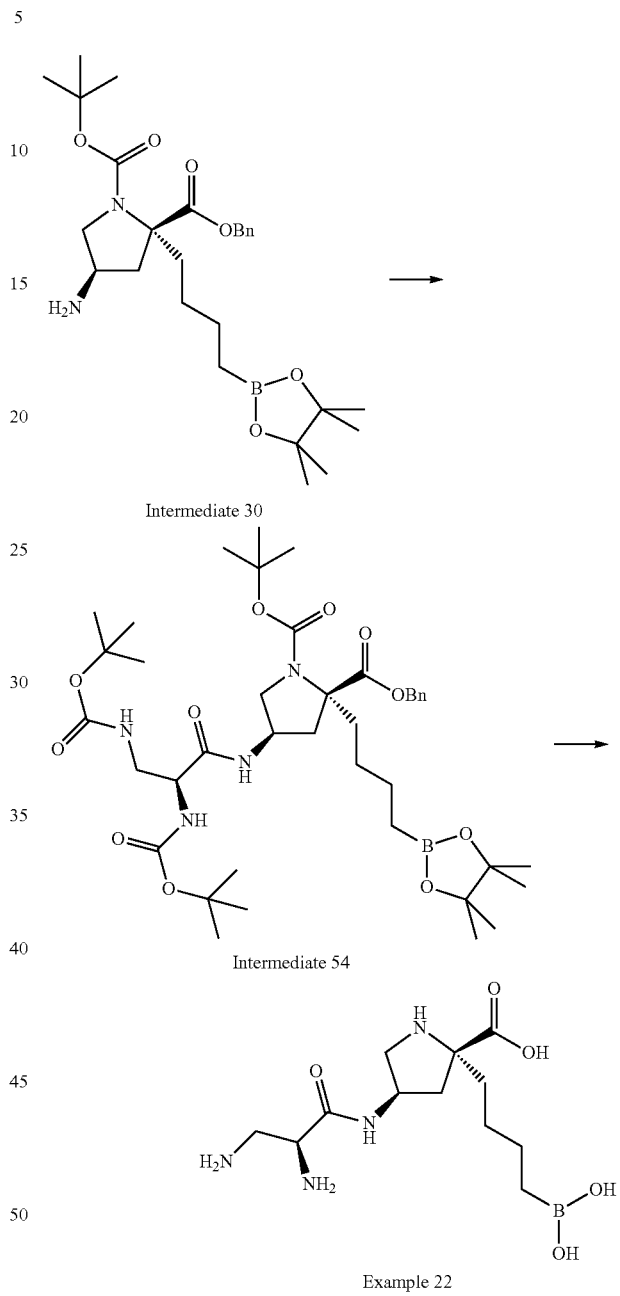

Intermediate 30

Intermediate 54

Example 22

Intermediate 54: 2-benzyl 1-tert-butyl (2R,4R)-4-[[(2S)-2,3-bis(tert-butoxycarbonylamino)propanoyl]amino]-2-[4-(4,4,5,5-tetramethyl-1,3,2-dioxaborolan-2-yl)butyl]pyrrolidine-1,2-dicarboxylate N,N-Diisopropylethylamine (0.14 mL, 0.82 mmol) was added to a solution of Boc-Dap(Boc)-OH.DCHA (0.238 g, 0.489 mmol) and HATU (0.186 g, 0.489 mmol) in DMF (3 mL) at 0° C. and the reaction stirred for 15 min. A solution of (2R,4R)-2-benzyl 1-tert-butyl 4-amino-2-(4-(4,4,5,5-tetramethyl-1,3,2-dioxaborolan-2-yl)butyl)pyrrolidine-1,2-dicarboxylate (Intermediate 30, 205 mg, 0.408 mmol) in DMF (1 mL) was added and the reaction stirred for 16 h while slowly warming to room temperature. The reaction mixture was diluted with EtOAc (50 mL) and washed with saturated aqueous NH$_4$Cl (2×25 mL), saturated aqueous NaHCO$_3$ (2×25 mL) and brine (20 mL). The organic layer was dried over Na$_2$SO$_4$, filtered and concentrated to dryness. The crude material was purified by silica gel chromatography (0-50% EtOAc in hexanes) to afford 2-benzyl 1-tert-butyl (2R,4R)-4-[[(2S)-2,3-bis(tert-butoxycarbonylamino)propanoyl]amino]-2-[4-(4,4,5,5-tetramethyl-1,3,2-dioxaborolan-2-yl)butyl]pyrrolidine-1,2-dicarboxylate (Intermediate 54, 214 mg, 66% yield) as a white foam and as a mixture of rotamers. $^1$H NMR (500 MHz, MeOH-d$_4$) δ 0.76 (2H, q), 1.19-1.26 (14H, m), 1.27-1.34 (6H, m), 1.37-1.52 (24H, m), 1.76-1.93 (1H, m), 2.06-2.31 (2H, m), 2.50 (1H, s), 3.19-3.27 (2H, m), 3.66-3.84 (1H, m), 4.00-4.13 (1H, m), 4.35-4.50 (1H, m), 5.04-5.25 (2H, m), 7.26-7.50 (5H, m); m/z: (ES$^+$) [M+H]$^+$=789.

Example 22: (2R,4R)-2-(4-boronobutyl)-4-[[(2S)-2,3-diaminopropanoyl]amino]pyrrolidine-2-carboxylic acid Pd/C (10% wt, 57 mg, 0.053 mmol) was added to a solution of 2-benzyl 1-tert-butyl (2R,4R)-4-[[(2S)-2,3-bis(tert-butoxycarbonylamino)propanoyl]amino]-2-[4-(4,4,5,5-tetramethyl-1,3,2-dioxaborolan-2-yl)butyl]pyrrolidine-1,2-dicarboxylate (Intermediate 54, 210 mg, 0.27 mmol) in EtOAc (4 mL). The flask was equipped with a balloon of H$_2$ and the suspension stirred at room temperature for 3 h. The reaction mixture was diluted with MeOH, filtered through diatomaceous earth and concentrated to dryness. The white solid was dissolved in DCM (1 mL) and trifluoroacetic acid (0.50 mL, 6.5 mmol) and the reaction stirred at room temperature for 2 h. The solution was concentrated, and the resulting residue was dissolved in Et$_2$O (2 mL) and 1 M HCl aq (2 mL). Phenylboronic acid (100 mg, 0.82 mmol) was added and the clear biphasic solution stirred at room temperature for 3 h. The reaction mixture was diluted with water and washed with Et$_2$O. The aqueous layer was lyophilized and purified by ion exchange chromatography (PoraPak Rxn CX 20 cc column). The desired product was eluted from the column using 5% ammonia in MeOH (20 mL) to afford (2R,4R)-2-(4-boronobutyl)-4-[[(2S)-2,3-diaminopropanoyl]amino]pyrrolidine-2-carboxylic acid (Example 22, 74 mg, 88% yield) as a white solid. $^1$H NMR (500 MHz, D$_2$O) δ 0.71 (2H, t), 1.11-1.24 (1H, m), 1.26-1.41 (3H, m), 1.75-1.89 (1H, m), 2.00-2.13 (1H, m), 2.31-2.48 (1H, m), 2.51-2.67 (1H, m), 3.39-3.53 (3H, m), 3.68-3.80 (1H, m), 4.27 (1H, t), 4.41-4.52 (1H, m); m/z: (ES$^+$) [M+H]$^+$=317.

Example 23: (2R,4R)-2-(4-boronobutyl)-4-(methylamino)pyrrolidine-2-carboxylic acid

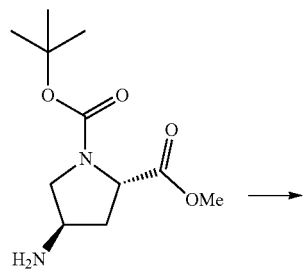

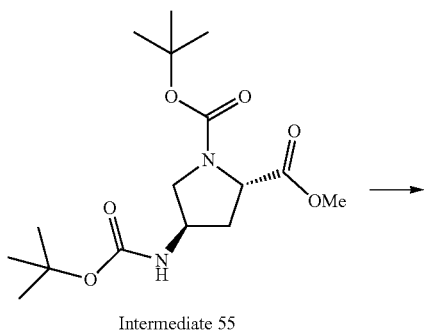

Intermediate 55

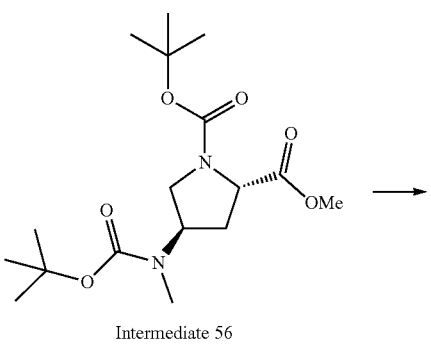

Intermediate 56

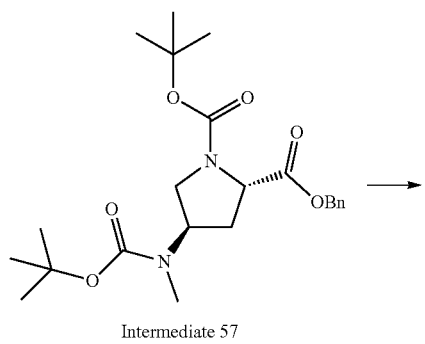

Intermediate 57

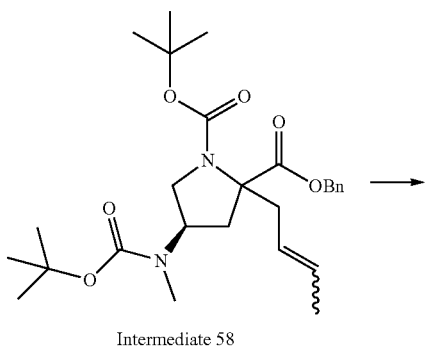

Intermediate 58

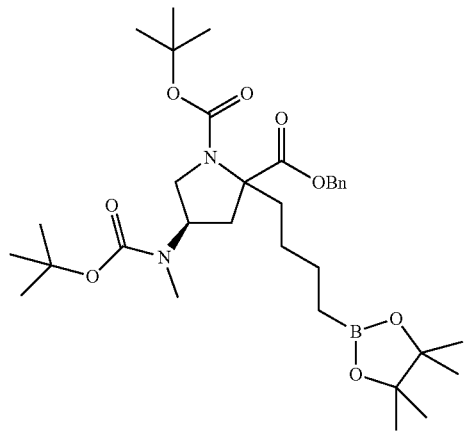

Intermediate 59

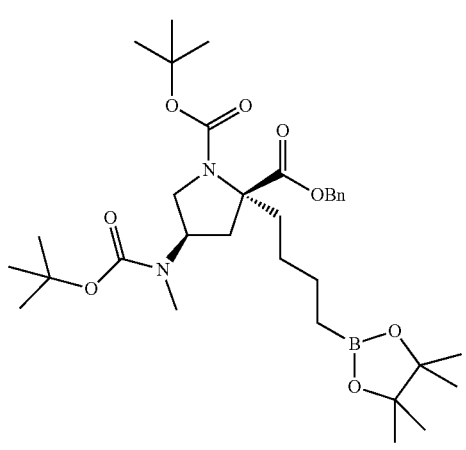

Intermediate 60

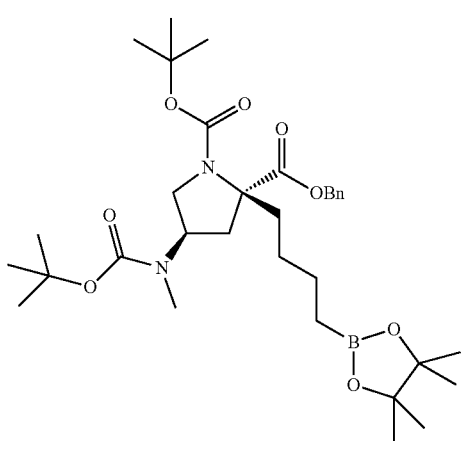

Intermediate 61

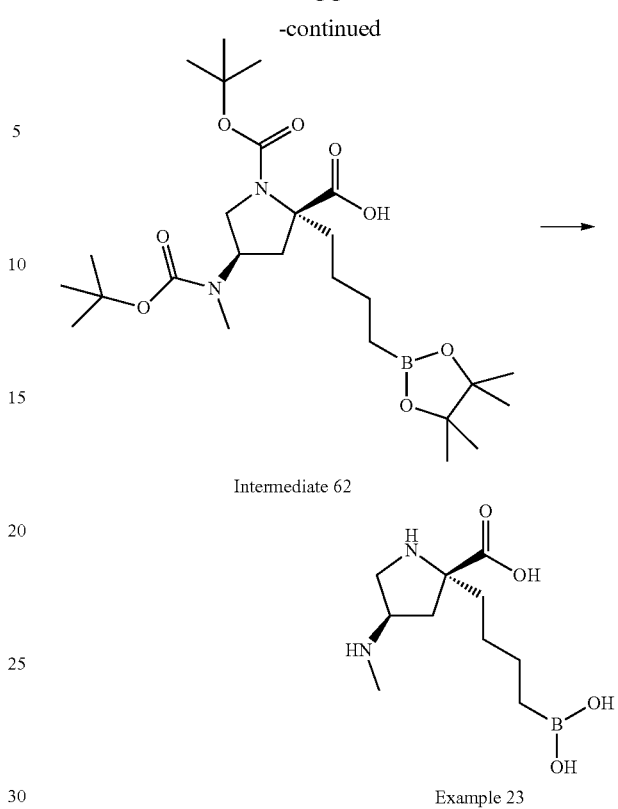

Intermediate 62

Example 23

Intermediate 55: 1-tert-butyl 2-methyl (2S,4R)-4-(tert-butoxycarbonylamino)pyrrolidine-1,2-dicarboxylate Di-tert-butyl dicarbonate (4.41 g, 20.2 mmol) was added to a solution of 1-(tert-butyl) 2-methyl (2S,4R)-4-aminopyrrolidine-1,2-dicarboxylate oxalic acid salt (4.50 g, 13.5 mmol) and triethylamine (5.63 mL, 40.4 mmol) in DCM (57 mL) and the reaction stirred at room temperature overnight under an atmosphere of $N_2$. The crude reaction mixture was diluted with DCM (200 mL) and washed sequentially with 0.5 M HCl (aq), saturated sodium bicarbonate and brine. The organic layer was dried over $Na_2SO_4$, filtered and concentrated to dryness. The crude material was purified by silica gel chromatography (DCM/MeOH) to afford 1-tert-butyl 2-methyl (2S,4R)-4-(tert-butoxycarbonylamino)pyrrolidine-1,2-dicarboxylate (Intermediate 55, 3.66 g, 79% yield) as a white solid. $^1$H NMR (500 MHz, DMSO-$d_6$) δ 1.29-1.42 (18H, m), 1.96-2.17 (2H, m), 3.12-3.17 (1H, m), 3.45-3.56 (1H, m), 3.62-3.69 (3H, m), 3.96-4.06 (1H, m), 4.24-4.34 (1H, m), 7.17-7.26 (1H, m); m/z: (ES$^+$) [M+H]$^+$=345.

Intermediate 56: 1-tert-butyl 2-methyl (2S,4R)-4-[tert-butoxycarbonyl(methyl)amino]pyrrolidine-1,2-dicarboxylate Sodium hydride (60% dispersion in mineral oil) (0.491 g, 12.3 mmol) was added portion-wise to a solution of 1-tert-butyl 2-methyl (2S,4R)-4-(tert-butoxycarbonylamino)pyrrolidine-1,2-dicarboxylate (Intermediate 55, 3.66 g, 10.7 mmol) in DMF (35 mL). Following addition, the reaction stirred for 10 min then methyl iodide (0.715 ml, 11.4 mmol) was added and the reaction stirred for an additional 3 h. The reaction mixture was cooled to 0° C. and quenched with water. The mixture was diluted with EtOAc (200 mL) and the layers were separated. The organic layer was washed sequentially with water and brine, dried over Na$_2$SO$_4$, filtered and concentrated to dryness. The crude material was purified by silica gel chromatography (hexanes/EtOAc) to afford 1-tert-butyl 2-methyl (2S,4R)-4-[tert-butoxycarbonyl (methyl)amino]pyrrolidine-1,2-dicarboxylate (Intermediate 56, 3.13 g, 82% yield) as a colorless oil. $^1$H NMR (500 MHz, DMSO-d$_6$) δ 1.28-1.41 (18H, m), 1.87-2.02 (1H, m), 2.29-2.44 (1H, m), 2.69 (3H, s), 3.13-3.25 (1H, m), 3.44-3.57 (1H, m), 3.60-3.68 (3H, m), 4.23-4.32 (1H, m), 4.62 (1H, br s); m/z: (ES$^+$) [M+H]$^+$=359.

Intermediate 57: 2-benzyl 1-tert-butyl (2S,4R)-4-[tert-butoxycarbonyl(methyl)amino]pyrrolidine-1,2-dicarboxylate A solution of sodium hydroxide (2.10 g, 52.4 mmol) in water (11 mL) was added to a solution of 1-tert-butyl 2-methyl (2S,4R)-4-[tert-butoxycarbonyl(methyl)amino] pyrrolidine-1,2-dicarboxylate (Intermediate 56, 3.13 g, 8.73 mmol) in THF (22 mL) and MeOH (11 mL) at 0° C. The reaction mixture stirred for 3 hrs while slowly warming to room temperature. The volatiles were removed under reduced pressure and the aqueous layer was acidified to pH ~3 with 5 M HCl (aq) and extracted with DCM. The combined organics were dried over Na$_2$SO$_4$, filtered and concentrated in dryness to afford the crude carboxylic acid as a white solid which was used without further purification.

Benzyl bromide (1.24 mL, 10.5 mmol) was added to a solution of the crude carboxylic acid, sodium iodide (1.737 g, 11.59 mmol) and K$_2$CO$_3$ (3.01 g, 21.8 mmol) in DMF (28 mL) and the reaction stirred at room temperature for 17 h. The reaction mixture was filtered, and the solids were rinsed with EtOAc. The filtrate was concentrated and purified by silica gel chromatography (hexanes/EtOAc) to afford 2-benzyl 1-tert-butyl (2S,4R)-4-[tert-butoxycarbonyl(methyl) amino]pyrrolidine-1,2-dicarboxylate (Intermediate 57, 3.05 g, 81% yield) as a colorless oil. $^1$H NMR (500 MHz, DMSO-d$_6$) δ 1.20-1.42 (18H, m), 1.91-2.07 (1H, m), 2.33-2.46 (1H, m), 2.69 (3H, s), 3.12-3.26 (1H, m), 3.44-3.57 (1H, m), 4.20-4.38 (1H, m), 4.66 (1H, br s), 5.07-5.20 (2H, m), 7.25-7.41 (5H, m); m/z: (ES$^+$) [M+H]$^+$=435.

Intermediate 58: 2-benzyl 1-tert-butyl (4R)-2-(but-2-enyl)-4-[tert-butoxycarbonyl(methyl)amino]pyrrolidine-1,2-dicarboxylate 2-Benzyl 1-tert-butyl (2S,4R)-4-[tert-butoxycarbonyl (methyl)amino]pyrrolidine-1,2-dicarboxylate (Intermediate 57, 3.05 g, 7.02 mmol) and crotyl bromide (1.08 mL, 10.5 mmol) were dissolved in THF (25 mL) and the solution was cooled to −78° C. under an atmosphere of N$_2$. A solution of KHMDS (0.5M in toluene, 21.0 mL, 10.5 mmol) was added dropwise to the reaction mixture and the reaction stirred for 17 h while slowly warming to room temperature. The crude reaction mixture was quenched with water and the volatiles were removed under reduced pressure. The crude mixture was diluted in DCM and the layers were separated. The organic layer was washed with water, dried over Na$_2$SO$_4$, filtered and concentrated to dryness. The crude material was purified by silica gel purification (hexanes/EtOAc) to afford 2-benzyl 1-tert-butyl (4R)-2-(but-2-enyl)-4-[tert-butoxycarbonyl(methyl)amino]pyrrolidine-1,2-dicarboxylate (Intermediate 58, 1.26 g, 37% yield) as a yellow oil and as a mixture of diastereomers, E/Z olefin isomers and rotamers. $^1$H NMR (500 MHz, DMSO-d$_6$) δ 1.23-1.44 (18H, m), 1.51-1.70 (3H, m), 2.00-2.26 (2H, m), 2.38-2.47 (1H, m), 2.57-2.68 (3H, m), 2.71-3.00 (1H, m), 3.00-3.25 (1H, m), 3.40-3.74 (1H, m), 4.54-4.80 (1H, m), 5.01-5.27 (2H, m), 5.28-5.47 (1H, m), 5.49-5.72 (1H, m), 7.25-7.42 (5H, m); m/z: (ES$^+$) [M+H]$^+$=489.

Intermediate 59: 2-benzyl 1-tert-butyl (4R)-4-[tert-butoxycarbonyl(methyl)amino]-2-[4-(4,4,5,5-tetramethyl-1,3,2-dioxaborolan-2-yl)butyl]pyrrolidine-1,2-dicarboxylate Bis(1,5-cyclooctadiene)diiridium(I) dichloride (269 mg, 0.400 mmol) and bis(diphenylphosphino)methane (308 mg, 0.801 mmol) were added to an oven-dried round-bottom flask. The flask was sealed and purged with N$_2$. The solids were dissolved in DCM (11 mL) and 4,4,5,5-tetramethyl-1, 3,2-dioxaborolane (1.28 mL, 8.82 mmol) was slowly added to the solution. The reaction was stirred at room temperature for 10 min. 2-Benzyl 1-tert-butyl (4R)-2-(but-2-enyl)-4-[tert-butoxycarbonyl(methyl)amino]pyrrolidine-1,2-dicarboxylate (Intermediate 58, 1.96 g, 4.01 mmol) was added to the reaction as a solution in DCM (7.5 mL) and the reaction mixture stirred for 16 h at room temperature. The reaction mixture was cooled to 0° C. and carefully quenched with MeOH and water. The layers were separated, and the aqueous layer was extracted with DCM. The combined organics were dried over Na$_2$SO$_4$, filtered and concentrated to dryness. The resulting residue was purified by flash silica chromatography (hexanes/EtOAc) to afford 2-benzyl 1-tert-butyl (4R)-4-[tert-butoxycarbonyl(methyl)amino]-2-[4-(4,4, 5,5-tetramethyl-1,3,2-dioxaborolan-2-yl)butyl]pyrrolidine-1,2-dicarboxylate (Intermediate 59, 2.5 g, 100% yield) as a yellow oil and as a mixture of diastereomers and rotamers. The purified material was subjected to chiral SFC [(S,S) Whelk-O1 column, 30 mm×250 mm, 5 μm, Temperature=20° C., Mobile phase=0-30% MeOH:CO2, UV detection @ 220 nm, loading=31 mg/inj, conc=125 mg/mL in MeOH, flow rate=75 mL/min, Outlet Pressure=100 bar] to give two diastereomers. The stereochemistry of each diastereomer was assigned retrospectively based on the enzyme potency of Example 23 and Example 24 to be congruent with other exemplified compounds.

Intermediate 60 (Isomer 2, 637 mg): 2-benzyl 1-tert-butyl (2R,4R)-4-[tert-butoxycarbonyl(methyl)amino]-2-[4-(4,4,5, 5-tetramethyl-1,3,2-dioxaborolan-2-yl)butyl]pyrrolidine-1, 2-dicarboxylate. $^1$H NMR (500 MHz, DMSO-d$_6$) δ 0.58-0.76 (2H, m), 1.15 (12H, d), 1.21-1.47 (22H, m), 1.69-1.82 (1H, m), 1.94-2.23 (3H, m), 2.56-2.62 (3H, m), 3.19-3.28 (1H, m), 3.45-3.57 (1H, m), 4.58-4.79 (1H, m), 5.01-5.26 (2H, m), 7.26-7.41 (5H, m).

Intermediate 61 (Isomer 1, 860 mg): 2-benzyl 1-tert-butyl (2S,4R)-4-[tert-butoxycarbonyl(methyl)amino]-2-[4-(4,4,5, 5-tetramethyl-1,3,2-dioxaborolan-2-yl)butyl]pyrrolidine-1, 2-dicarboxylate. $^1$H NMR (500 MHz, DMSO-d$_6$) δ 0.62-0.71 (2H, m), 1.15 (12H, s), 1.20-1.42 (22H, m), 1.67-1.84 (1H, m), 1.92-2.32 (3H, m), 2.69 (3H, s), 3.04-3.15 (1H, m), 3.57-3.71 (1H, m), 4.52-4.73 (1H, m), 4.98-5.25 (2H, m), 7.24-7.40 (5H, m).

Intermediate 62: (2R,4R)-1-tert-butoxycarbonyl-4-[tert-butoxycarbonyl(methyl)amino]-2-[4-(4,4,5,5-tetramethyl-1,3,2-dioxaborolan-2-yl)butyl]pyrrolidine-2-carboxylic acid Pd/C (10% wt, 165 mg, 0.155 mmol) was added to a solution of 2-benzyl 1-tert-butyl (2R,4R)-4-[tert-butoxycarbonyl(methyl)amino]-2-[4-(4,4,5,5-tetramethyl-1,3,2-dioxaborolan-2-yl)butyl]pyrrolidine-1,2-dicarboxylate (Intermediate 60, 637 mg, 1.03 mmol) in EtOAc (7 mL). The flask was equipped with a balloon of H$_2$ and the suspension stirred overnight at room temperature. The reaction mixture was diluted with MeOH and filtered through diatomaceous earth. The filtrate was concentrated to dryness and purified by silica gel chromatography (hexanes/EtOAc) to afford (2R, 4R)-1-tert-butoxycarbonyl-4-[tert-butoxycarbonyl(methyl)amino]-2-[4-(4,4,5,5-tetramethyl-1,3,2-dioxaborolan-2-yl)butyl]pyrrolidine-2-carboxylic acid (Intermediate 62, 350 mg, 64% yield) as a white solid. $^1$H NMR (500 MHz, DMSO-d$_6$) δ 0.63-0.73 (2H, m), 1.14-1.19 (12H, m), 1.22-1.42 (21H, m), 1.63-1.77 (1H, m), 1.99-2.18 (3H, m), 2.63-2.67 (3H, m), 3.21-3.27 (2H, m), 3.41-3.55 (1H, m), 4.57-4.80 (1H, m), 12.32-12.75 (1H, m); m/z: (ES$^+$) [M+H]$^+$ =527.

Example 23: (2R,4R)-2-(4-boronobutyl)-4-(methylamino)pyrrolidine-2-carboxylic acid Trifluoroacetic acid (0.51 mL, 6.7 mmol) was added dropwise to a stirred solution of (2R,4R)-1-tert-butoxycarbonyl-4-[tert-butoxycarbonyl(methyl)amino]-2-[4-(4,4,5,5-tetramethyl-1,3,2-dioxaborolan-2-yl)butyl]pyrrolidine-2-carboxylic acid (Intermediate 62, 350 mg, 0.66 mmol) in DCM (4 mL) at room temperature. After 1 h the solution was concentrated under reduced pressure and the resulting residue was dissolved in 1M HCl aq (5 mL) and Et$_2$O (5 mL). Phenylboronic acid (162 mg, 1.33 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 60 cc column). The desired product was eluted from the column using 5% ammonia in MeOH (60 mL) to afford (2R,4R)-2-(4-boronobutyl)-4-(methylamino)pyrrolidine-2-carboxylic acid (Example 23, 140 mg, 86% yield) as a white solid. $^1$H NMR (500 MHz, D$_2$O) δ 0.72-0.82 (2H, m), 1.09-1.43 (4H, m), 1.62-1.77 (1H, m), 1.83-1.95 (1H, m), 2.23 (2H, d), 2.46 (3H, s), 3.02-3.11 (1H, m), 3.37-3.49 (1H, m), 3.49-3.61 (1H, m); m/z: (ES$^+$) [M+H]$^+$=245.

Example 24: (2S,4R)-2-(4-boronobutyl)-4-(methylamino)pyrrolidine-2-carboxylic acid

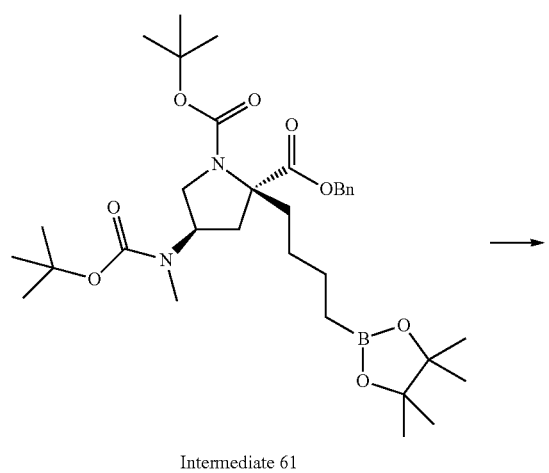

Intermediate 61

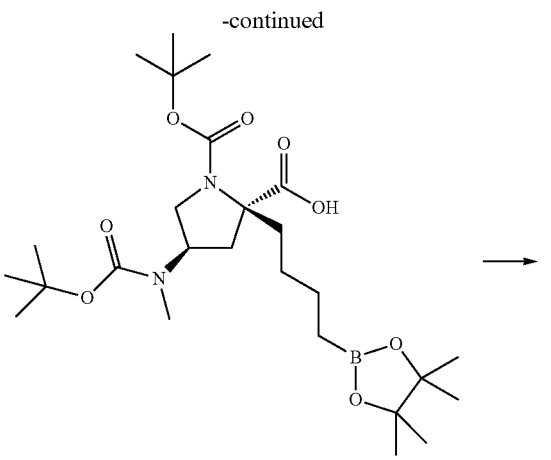

Intermediate 63

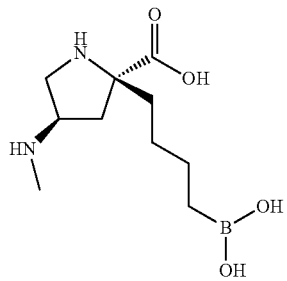

Example 24

Intermediate 63: (2S,4R)-1-tert-butoxycarbonyl-4-[tert-butoxycarbonyl(methyl)amino]-2-[4-(4,4,5,5-tetramethyl-1,3,2-dioxaborolan-2-yl)butyl]pyrrolidine-2-carboxylic acid Pd/C (10% wt, 223 mg, 0.209 mmol) was added to a solution of 2-benzyl 1-tert-butyl (2S,4R)-4-[tert-butoxycarbonyl(methyl)amino]-2-[4-(4,4,5,5-tetramethyl-1,3,2-dioxaborolan-2-yl)butyl]pyrrolidine-1,2-dicarboxylate (Intermediate 61, 860 mg, 1.39 mmol) in EtOAc (9.3 mL). The flask was equipped with a balloon of H$_2$ and the suspension stirred overnight at room temperature. The reaction mixture was diluted with MeOH and filtered through diatomaceous earth. The filtrate was concentrated to dryness and purified by silica gel chromatography (hexanes/EtOAc) to afford (2S,4R)-1-tert-butoxycarbonyl-4-[tert-butoxycarbonyl (methyl)amino]-2-[4-(4,4,5,5-tetramethyl-1,3,2-dioxaborolan-2-yl)butyl]pyrrolidine-2-carboxylic acid (Intermediate 63, 520 mg, 71% yield) as a white solid. $^1$H NMR (500 MHz, DMSO-d$_6$) δ 0.60-0.75 (2H, m), 1.16 (12H, s), 1.28-1.45 (22H, m), 1.56-1.74 (1H, m), 1.84-1.95 (1H, m), 2.01-2.22 (2H, m), 2.69 (3H, s), 3.01-3.17 (1H, m), 3.56-3.70 (1H, m), 4.52-4.73 (1H, m), 12.35-12.77 (1H, m); m/z: (ES$^+$) [M+H]$^+$=527.

Example 24: (2S,4R)-2-(4-boronobutyl)-4-(methylamino)pyrrolidine-2-carboxylic acid Trifluoroacetic acid (1.23 mL, 16.0 mmol) was added dropwise to a stirred solution of (2S,4R)-1-tert-butoxycarbonyl-4-[tert-butoxycarbonyl(methyl)amino]-2-[4-(4,4,5,5-tetramethyl-1,3,2-dioxaborolan-2-yl)butyl]pyrrolidine-2-carboxylic acid (Intermediate 63, 520 mg, 0.80 mmol) in DCM (8.5 mL) at room temperature. After 1 h the solution was concentrated under reduced pressure and the resulting residue was dissolved in 1M HCl aq (5 mL) and Et$_2$O (5 mL).

Phenylboronic acid (196 mg, 1.60 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 60 cc column). The desired product was eluted from the column using 5% ammonia in MeOH (60 mL) to afford (2S,4R)-2-(4-boronobutyl)-4-(methylamino)pyrrolidine-2-carboxylic acid (Example 24, 163 mg, 83% yield) as a white solid. $^1$H NMR (500 MHz, D$_2$O) δ 0.70-0.90 (2H, m), 1.10-1.46 (4H, m), 1.65-1.77 (2H, m), 1.96-2.07 (1H, m), 2.43 (3H, s), 2.68-2.77 (1H, m), 2.96-3.10 (1H, m), 3.37-3.50 (1H, m), 3.50-3.60 (1H, m); m/z: (ES$^+$) [M+H]$^+$=245.

Example 25: (2R,4R)-2-(4-boronobutyl)-4-(dimethylamino)pyrrolidine-2-carboxylic acid

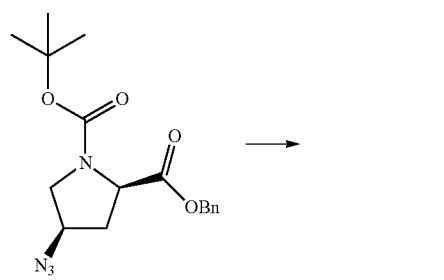

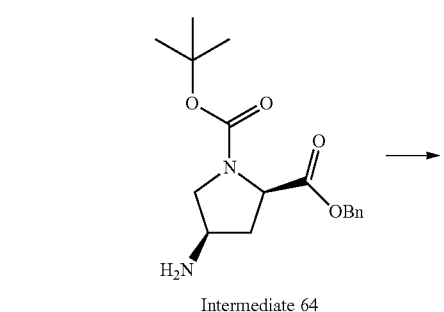

Intermediate 64

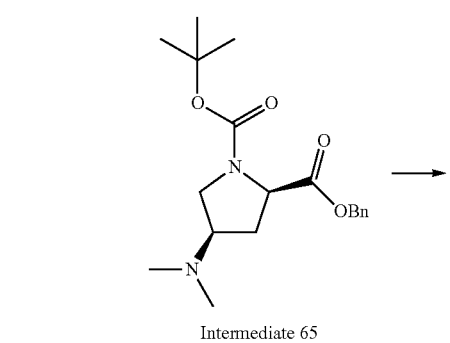

Intermediate 65

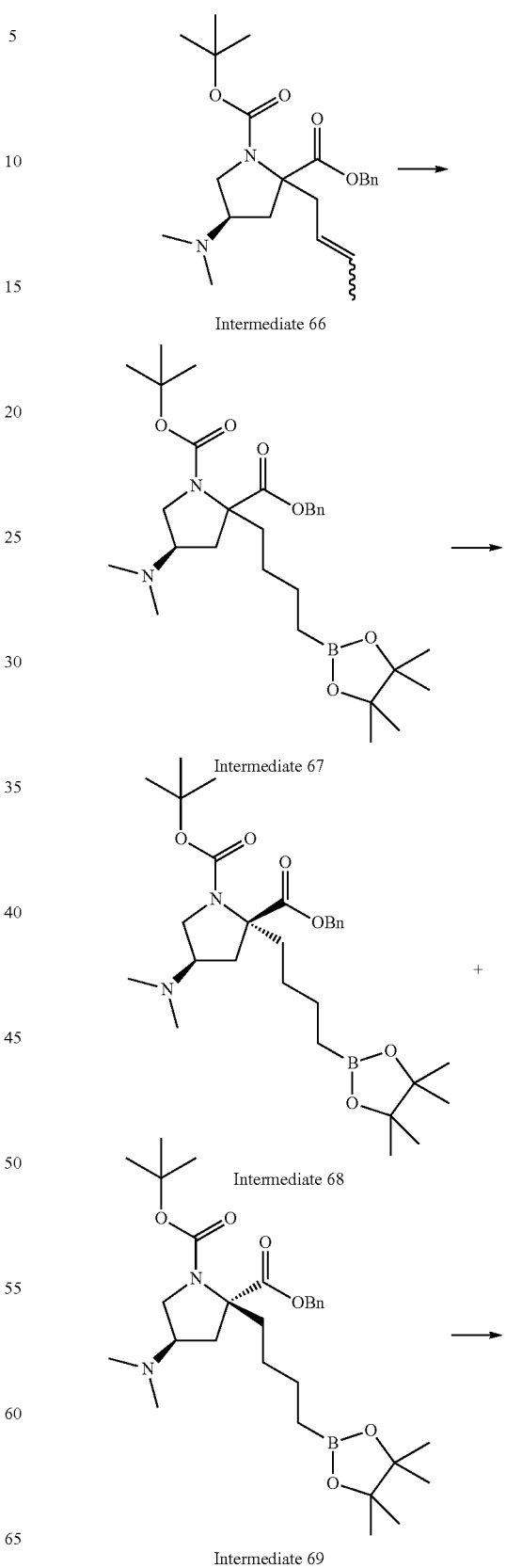

Intermediate 66

Intermediate 67

Intermediate 68

Intermediate 69

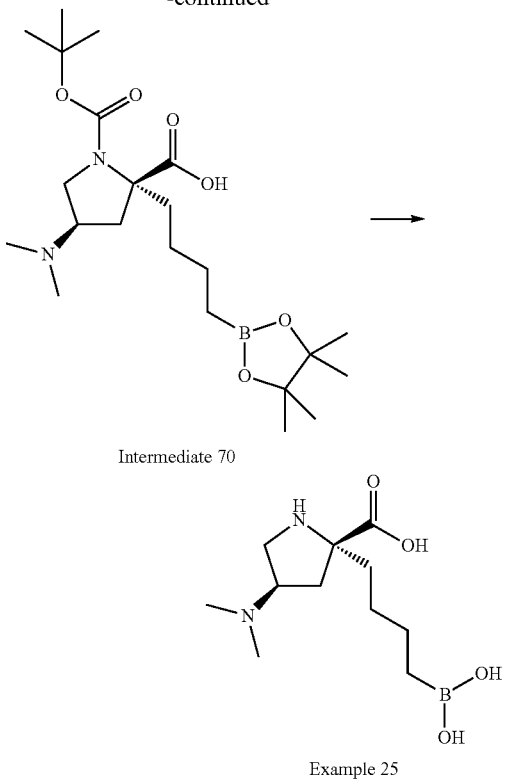

Intermediate 70

Example 25

Intermediate 64: 2-benzyl 1-tert-butyl (2R,4R)-4-aminopyrrolidine-1,2-dicarboxylate Triphenylphosphine (7.87 g, 30.0 mmol) and water (0.54 mL, 30.0 mmol) were added to a solution of 2-benzyl 1-(tert-butyl) (2R,4R)-4-azidopyrrolidine-1,2-dicarboxylate (5.20 g, 15.0 mmol) in THF (68 mL) at room temperature. The reaction was heated to 60° C. and stirred for 6 h. The reaction mixture was cooled to room temperature, diluted with EtOAc, and washed sequentially with water (2×100 mL) and saturated aqueous sodium chloride (100 mL). The organic layer was dried over $Na_2SO_4$, filtered and concentrated to dryness. The crude material was purified by silica gel chromatography (DCM/MeOH) to afford 2-benzyl 1-tert-butyl (2R,4R)-4-aminopyrrolidine-1,2-dicarboxylate (Intermediate 64, 3.2 g, 67% yield) as a colorless oil. $^1$H NMR (500 MHz, DMSO-$d_6$) δ 1.20-1.49 (9H, m), 1.53-1.64 (1H, m), 1.65-1.79 (2H, m), 2.26-2.40 (1H, m), 2.85-3.01 (1H, m), 3.31-3.42 (1H, m), 3.45-3.56 (1H, m), 4.13-4.24 (1H, m), 4.99-5.25 (2H, m), 7.36 (5H, s); m/z: ($ES^+$) $[M+H]^+$=321.

Intermediate 65: 2-benzyl 1-tert-butyl (2R,4R)-4-(dimethylamino)pyrrolidine-1,2-dicarboxylate Sodium triacetoxyborohydride (6.35 g, 29.9 mmol) was added portion-wise to a solution of 2-benzyl 1-tert-butyl (2R,4R)-4-aminopyrrolidine-1,2-dicarboxylate (Intermediate 64, 3.20 g, 9.99 mmol) and formaldehyde (37 wt % in $H_2O$, 4.46 mL, 59.9 mmol) in MeOH (79 mL). Following addition, the reaction stirred at room temperature for 17 h. The volatiles were removed under reduced pressure and the resulting residue was diluted with DCM. The solids were removed by filtration and the filtrate was concentrated to dryness. The crude material was purified by silica gel chromatography (hexanes/EtOAc with $NH_4OH$) to afford 2-benzyl 1-tert-butyl (2R,4R)-4-(dimethylamino)pyrrolidine-1,2-dicarboxylate (Intermediate 65, 3.00 g, 86% yield). $^1$H NMR (500 MHz, DMSO-$d_6$) δ 1.24 (9H, s), 1.53-1.67 (1H, m), 2.10 (6H, s), 2.40-2.48 (1H, m), 2.53-2.73 (1H, m), 2.83-3.06 (1H, m), 3.59-3.69 (1H, m), 4.15-4.29 (1H, m), 5.02-5.21 (2H, m), 7.26-7.42 (5H, m); m/z: ($ES^+$) $[M+H]^+$=350.

Intermediate 66: 2-benzyl 1-tert-butyl (4R)-2-(but-2-enyl)-4-(dimethylamino)pyrrolidine-1,2-dicarboxylate 2-Benzyl 1-tert-butyl (2R,4R)-4-(dimethylamino)pyrrolidine-1,2-dicarboxylate (Intermediate 65, 3.00 g, 8.61 mmol) and crotyl bromide (1.33 mL, 12.9 mmol) were dissolved in THF (18 mL) and the solution was cooled to −78° C. under an atmosphere of $N_2$. A solution of KHMDS (0.5M in toluene, 25.8 mL, 12.9 mmol) was added dropwise to the reaction mixture and the reaction stirred for 17 h while slowly warming to room temperature. The crude reaction mixture was quenched with water and the volatiles were removed under reduced pressure. The crude mixture was diluted in DCM and the layers were separated. The organic layer was washed with water, dried over $Na_2SO_4$, filtered and concentrated to dryness. The crude material was purified by silica gel purification (hexanes/EtOAc) to afford 2-benzyl 1-tert-butyl (4R)-2-(but-2-enyl)-4-(dimethylamino)pyrrolidine-1,2-dicarboxylate (Intermediate 66, 1.55 g, 45% yield) as a yellow oil and as a mixture of diastereomers, E/Z olefin isomers and rotamers. $^1$H NMR (500 MHz, DMSO-$d_6$) δ 1.21-1.44 (9H, m), 1.51-1.70 (3H, m), 1.79-1.96 (1H, m), 2.05 (6H, s), 2.08-2.24 (1H, m), 2.31-2.43 (1H, m), 2.54-2.74 (1H, m), 2.75-3.08 (2H, m), 3.56-3.86 (1H, m), 5.00-5.23 (2H, m), 5.23-5.42 (1H, m), 5.43-5.73 (1H, m), 7.23-7.41 (5H, m); m/z: ($ES^+$) $[M+H]^+$=403.

Intermediate 67: 2-benzyl 1-tert-butyl (4R)-4-(dimethylamino)-2-[4-(4,4,5,5-tetramethyl-1,3,2-dioxaborolan-2-yl)butyl]pyrrolidine-1,2-dicarboxylate Bis(1,5-cyclooctadiene)diiridium(I) dichloride (240 mg, 0.36 mmol) and bis(diphenylphosphino)methane (275 mg, 0.715 mmol) were added to an oven-dried round-bottom flask. The flask was sealed and purged with $N_2$. The solids were dissolved in DCM (10 mL) and 4,4,5,5-tetramethyl-1,3,2-dioxaborolane (1.14 mL, 7.87 mmol) was slowly added to the solution. The reaction was stirred at room temperature for 10 min. 2-benzyl 1-tert-butyl (4R)-2-(but-2-enyl)-4-(dimethylamino)pyrrolidine-1,2-dicarboxylate (Intermediate 66, 1.44 g, 3.58 mmol) was added to the reaction as a solution in DCM (6.7 mL) and the reaction mixture stirred for 16 h at room temperature. The reaction mixture was cooled to 0° C. and carefully quenched with MeOH and water. The layers were separated, and the aqueous layer was extracted with DCM. The combined organics were dried over $Na_2SO_4$, filtered and concentrated to dryness. The resulting residue was purified by flash silica chromatography (hexanes/EtOAc) to afford 2-benzyl 1-tert-butyl (4R)-4-(dimethylamino)-2-[4-(4,4,5,5-tetramethyl-1,3,2-dioxaborolan-2-yl)butyl]pyrrolidine-1,2-dicarboxylate (Intermediate 67, 1.5 g, 79% yield) as a yellow oil and as a mixture of diastereomers and rotamers. The purified material was subjected to chiral SFC [(S,S)Whelk-O1 column, 30 mm×250 mm, 5 μm, Temperature=20° C., Mobile phase=0-15% MeOH:CO2, UV detection @ 220 nm, loading=32 mg/inj, conc=80 mg/mL in MeOH, flow rate=120 mL/min, Outlet Pressure=100 bar] to give two diastereomers. The stereochemistry of each diastereomer was assigned retrospectively based on the enzyme potency of Example 25 and Example 26 to be congruent with other exemplified compounds.

Intermediate 68 (Isomer 2, 190 mg): 2-benzyl 1-tert-butyl (2R,4R)-4-(dimethylamino)-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.64-0.71 (2H, m), 0.97-1.12 (1H, m), 1.13-1.17 (12H, m), 1.24 (13H, s), 1.57-1.81 (1H, m), 1.81-1.99 (1H, m), 2.06 (6H, s), 2.09-2.21 (1H, m), 2.55-2.74 (1H, m), 3.02-3.12 (1H, m), 3.59-3.70 (1H, m), 5.00-5.20 (2H, m), 7.27-7.41 (5H, m).

Intermediate 69 (Isomer 1, 491 mg): 2-benzyl 1-tert-butyl (2S,4R)-4-(dimethylamino)-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.52-0.72 (2H, m), 0.93-1.12 (1H, m), 1.12-1.20 (12H, m), 1.20-1.39 (13H, m), 1.59-1.74 (1H, m), 1.77-1.93 (1H, m), 2.06 (6H, s), 2.08-2.15 (1H, m), 2.53-2.65 (1H, m), 2.78-2.96 (1H, m), 3.67-3.82 (1H, m), 5.00-5.21 (2H, m), 7.27-7.42 (5H, m).

Intermediate 70: (2R,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid Pd/C (10% wt, 57 mg, 0.054 mmol) was added to a solution of 2-benzyl 1-tert-butyl (2R,4R)-4-(dimethylamino)-2-[4-(4,4,5,5-tetramethyl-1,3,2-dioxaborolan-2-yl)butyl]pyrrolidine-1,2-dicarboxylate (Intermediate 68, 189 mg, 0.356 mmol) in EtOAc (2.4 mL). The flask was equipped with a balloon of $H_2$ and the suspension stirred overnight at room temperature. The reaction mixture was diluted with MeOH and filtered through diatomaceous earth. The filtrate was concentrated to dryness to afford (2R,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid (Intermediate 70, 150 mg, 96% yield) as a white solid which was used without further purification. $^1$H NMR (500 MHz, DMSO-$d_6$) δ 0.53-0.70 (2H, m), 1.11-1.20 (12H, m), 1.21-1.41 (14H, m), 1.56-1.71 (1H, m), 1.92-2.06 (2H, m), 2.20 (7H, s), 2.69-2.78 (1H, m), 3.37-3.51 (1H, m), 3.67-4.21 (1H, m); m/z: (ES$^+$) [M+H]$^+$=441.

Example 25: (2R,4R)-2-(4-boronobutyl)-4-(dimethylamino)pyrrolidine-2-carboxylic acid Trifluoroacetic acid (0.26 mL, 3.4 mmol) was added dropwise to a stirred solution of (2R,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid (Intermediate 70, 150 mg, 0.34 mmol) in DCM (2 mL) at room temperature. After 1 h the solution was concentrated under reduced pressure and the resulting residue was dissolved in 1M HCl aq (5 mL) and $Et_2O$ (5 mL). Phenylboronic acid (83 mg, 0.68 mmol) was added and the clear biphasic solution stirred at room temperature for 1 h. The mixture was diluted with $Et_2O$ and water and the layers were separated. The aqueous layer was washed with $Et_2O$. The aqueous layer was lyophilized and purified by ion exchange chromatography (PoraPak Rxn CX 20 cc column). The desired product was eluted from the column using 5% ammonia in MeOH (20 mL) to afford (2R,4R)-2-(4-boronobutyl)-4-(dimethylamino)pyrrolidine-2-carboxylic acid (Example 25, 73 mg, 83% yield) as a white solid. $^1$H NMR (500 MHz, $D_2O$) δ 0.62-0.73 (2H, m), 1.14-1.36 (4H, m), 1.79-1.90 (1H, m), 1.99-2.10 (1H, m), 2.57-2.73 (2H, m), 2.82-2.90 (6H, m), 3.48-3.56 (1H, m), 3.89-3.98 (1H, m), 4.12-4.20 (1H, m); m/z: (ES$^+$) [M+H]$^+$=259.

Example 26: (2S,4R)-2-(4-boronobutyl)-4-(dimethylamino)pyrrolidine-2-carboxylic acid

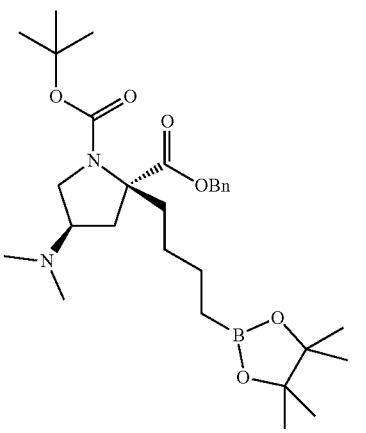

Intermediate 69

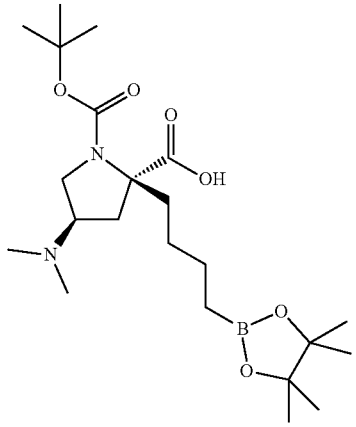

Intermediate 71

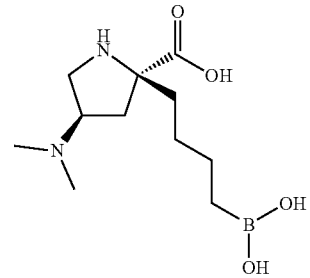

Example 26

Intermediate 71: (2S,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid Pd/C (10% wt, 148 mg, 0.139 mmol) was added to a solution of 2-benzyl 1-tert-butyl (2S,4R)-4-(dimethylamino)-2-[4-(4,4,5,5-tetramethyl-1,3,2-dioxaborolan-2-yl)

butyl]pyrrolidine-1,2-dicarboxylate (Intermediate 69, 490 mg, 0.93 mmol) in EtOAc (6.7 mL). The flask was equipped with a balloon of $H_2$ and the suspension stirred overnight at room temperature. The reaction mixture was diluted with MeOH and filtered through diatomaceous earth. The filtrate was concentrated to dryness to afford (2S,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid (Intermediate 71, 405 mg, 99% yield) as a white solid which was used without further purification. $^1$H NMR (500 MHz, DMSO-$d_6$) δ 0.52-0.71 (2H, m), 0.83-1.06 (1H, m), 1.16 (12H, s), 1.32 (12H, s), 1.53-1.67 (1H, m), 1.75-1.88 (1H, m), 2.01-2.13 (7H, m), 2.54-2.69 (1H, m), 2.79-2.95 (1H, m), 3.66-3.83 (1H, m), 7.24-7.46 (1H, m), 11.86-12.88 (1H, m); m/z: (ES$^+$) [M+H]$^+$=441.

Example 26: (2S,4R)-2-(4-boronobutyl)-4-(dimethylamino)pyrrolidine-2-carboxylic acid Trifluoroacetic acid (1.0 mL, 13 mmol) was added dropwise to a stirred solution of (2S,4R)-1-tert-butoxycarbonyl-4-(dimethylamino)-2-[4-(4,4,5,5-tetramethyl-1,3,2-dioxaborolan-2-yl)butyl]pyrrolidine-2-carboxylic acid (Intermediate 71, 405 mg, 0.919 mmol) in DCM (5.1 mL) at room temperature. After 1 h the solution was concentrated under reduced pressure and the resulting residue was dissolved in 1M HCl aq (5 mL) and Et$_2$O (5 mL). Phenylboronic acid (224 mg, 1.84 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 60 cc column). The desired product was eluted from the column using 5% ammonia in MeOH (60 mL) to afford (2S,4R)-2-(4-boronobutyl)-4-(dimethylamino)pyrrolidine-2-carboxylic acid (Example 26, 206 mg, 87% yield) as a white solid. $^1$H NMR (500 MHz, D$_2$O) δ 0.71-0.89 (2H, m), 1.12-1.44 (4H, m), 1.70-1.82 (2H, m), 1.97-2.11 (1H, m), 2.29 (6H, s), 2.62-2.71 (1H, m), 2.95-3.10 (2H, m), 3.61-3.68 (1H, m); m/z: (ES$^+$) [M+H]$^+$=259.

Example 27: (2R,4R)-4-(2-aminoethylamino)-2-(4-boronobutyl)pyrrolidine-2-carboxylic acid

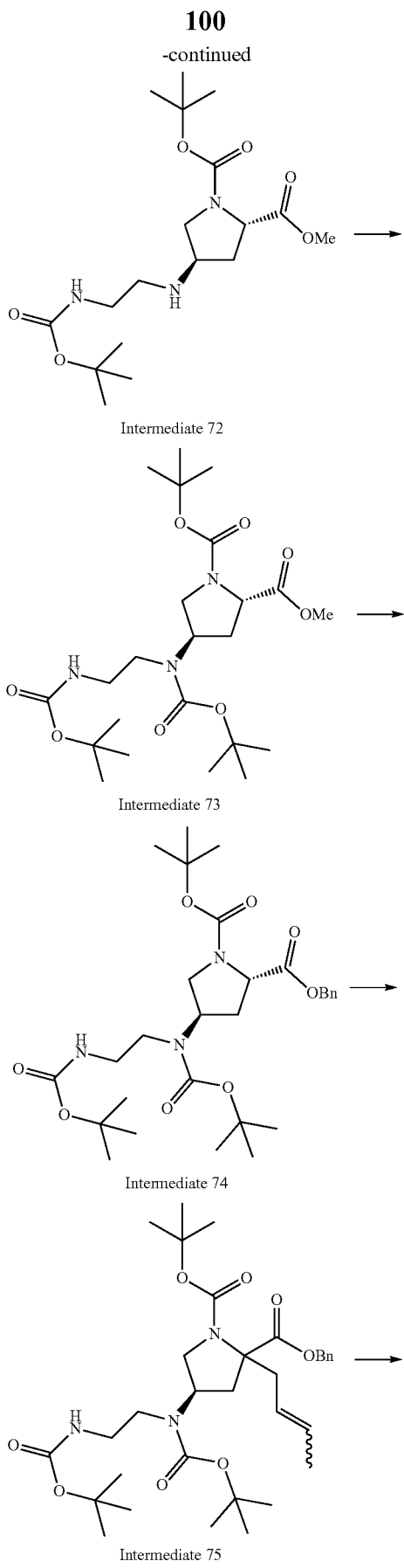

Intermediate 72

Intermediate 73

Intermediate 74

Intermediate 75

101
-continued

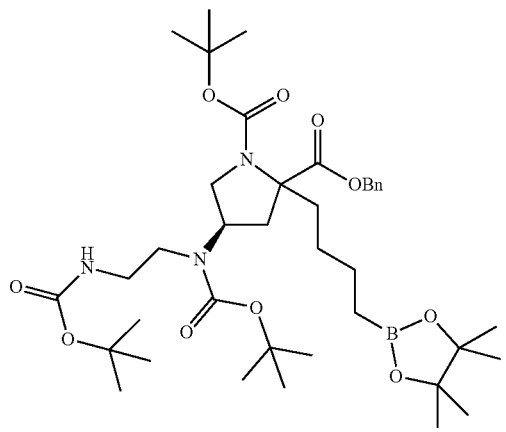

Intermediate 76

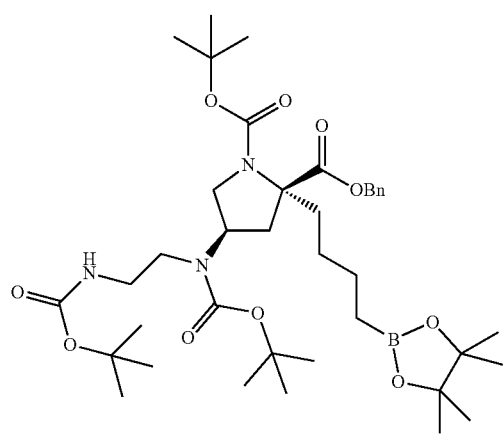

Intermediate 77

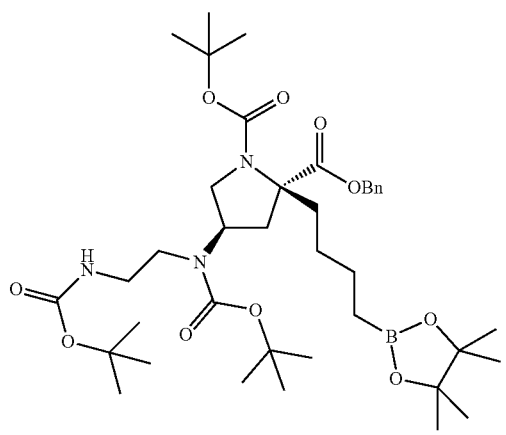

Intermediate 78

102
-continued

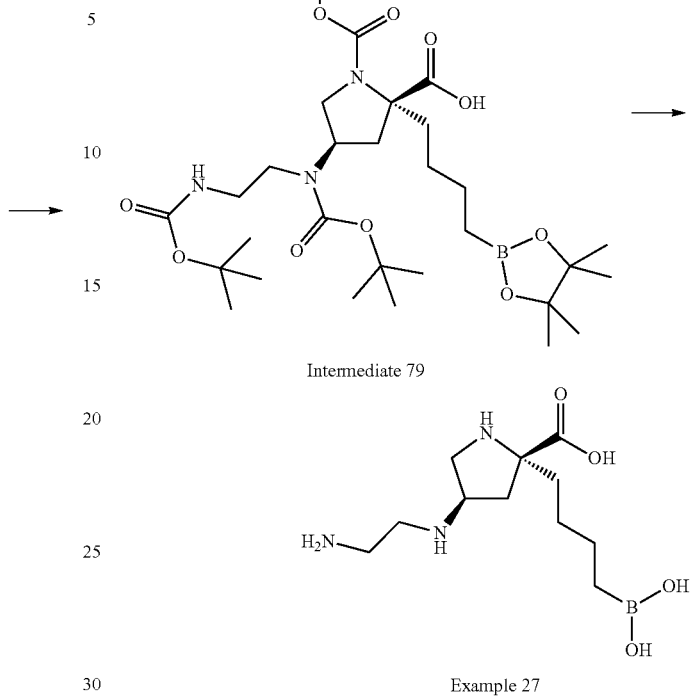

Intermediate 79

Example 27

Intermediate 72: 1-tert-butyl 2-methyl (2S,4R)-4-[2-(tert-butoxycarbonylamino)ethylamino]pyrrolidine-1,2-dicarboxylate Acetic acid (42 μL, 0.73 mmol) was added to a solution of 1-(tert-butyl) 2-methyl (2S,4R)-4-aminopyrrolidine-1,2-dicarboxylate (7.48 g, 30.6 mmol) and tert-butyl (2-oxoethyl)carbamate (4.64 g, 29.2 mmol) in MeOH (194 mL) and the reaction stirred at room temperature for 3 h. The solution was cooled to 0° C. and sodium triacetoxyborohydride (9.27 g, 43.7 mmol) was added portion-wise. The reaction stirred overnight while slowly warming to room temperature. The reaction mixture was concentrated under reduced pressure and the resulting residue was diluted with DCM washed sequentially with saturated sodium bicarbonate, water and saturated sodium chloride. The organic layer was dried over $Na_2SO_4$, filtered and concentrated to dryness. The crude material was purified by silica gel chromatography (DCM/EtOAc/MeOH) to afford 1-tert-butyl 2-methyl (2S,4R)-4-[2-(tert-butoxycarbonylamino)ethylamino]pyrrolidine-1,2-dicarboxylate (Intermediate 72, 4.77 g, 42% yield) as a colorless oil. $^1$H NMR (500 MHz, DMSO-$d_6$) δ 1.25-1.48 (20H, m), 1.84-2.07 (3H, m), 2.88-2.98 (2H, m), 3.02-3.17 (1H, m), 3.17-3.27 (1H, m), 3.40-3.51 (1H, m), 3.64 (3H, s), 4.14-4.24 (1H, m), 6.63-6.74 (1H, m); m/z: ($ES^+$) $[M+H]^+$=388.

Intermediate 73: 1-tert-butyl 2-methyl (2S,4R)-4-[tert-butoxycarbonyl-[2-(tert-butoxycarbonylamino)ethyl]amino]pyrrolidine-1,2-dicarboxylate Di-tert-butyl dicarbonate (4.29 mL, 18.5 mmol) was added to a solution of 1-tert-butyl 2-methyl (2S,4R)-4-[2-(tert-butoxycarbonylamino)ethylamino]pyrrolidine-1,2-dicarboxylate (Intermediate 72, 4.77 g, 12.3 mmol) and N,N-diisopropylethylamine (4.30 mL, 24.6 mmol) in DCM (53 mL) at room temperature and the reaction stirred for 17 h. The reaction mixture was diluted with DCM and washed sequentially with water and saturated aqueous sodium chloride. The organic layer was dried over $Na_2SO_4$, filtered and concentrated to dryness. The crude material was purified by silica gel chromatography (hexanes/EtOAc) to afford 1-tert-butyl 2-methyl (2S,4R)-4-[tert-butoxycarbonyl-[2-(tert-butoxycarbonylamino)ethyl]amino]pyrrolidine-1,2-dicarboxylate (Intermediate 73, 4.25 mg, 71% yield). $^1$H NMR (500 MHz, DMSO-$d_6$) δ 1.21-1.27 (1H, m), 1.27-1.42 (27H, m), 1.99-2.07 (1H, m), 2.33-2.46 (1H, m), 2.93-3.14 (3H, m), 3.17-3.24 (1H, m), 3.48-3.61 (1H, m), 3.61-3.69 (3H, m), 4.20-4.44 (2H, m), 6.79-6.94 (1H, m); m/z: ($ES^+$) $[M+H]^+$=488.

Intermediate 74: 2-benzyl 1-tert-butyl (2S,4R)-4-[tert-butoxycarbonyl-[2-(tert-butoxycarbonylamino)ethyl]amino]pyrrolidine-1,2-dicarboxylate A solution of sodium hydroxide (2.09 g, 52.3 mmol) in water (11 mL) was added to a solution of 1-tert-butyl 2-methyl (2S,4R)-4-[tert-butoxycarbonyl-[2-(tert-butoxycarbonylamino)ethyl]amino]pyrrolidine-1,2-dicarboxylate (Intermediate 73, 4.25 g, 8.72 mmol) in THF (22 mL) and MeOH (11 mL) at 0° C. The reaction mixture stirred for 6 hrs while slowly warming to room temperature. The volatiles were removed under reduced pressure and the aqueous layer was acidified to pH ~3 with 5 M HCl (aq) and extracted with DCM. The combined organics were dried over $Na_2SO_4$, filtered and concentrated in dryness to afford the crude carboxylic acid as a white solid which was used without further purification.

Benzyl bromide (1.24 mL, 10.5 mmol) was added to a solution of the crude carboxylic acid, sodium iodide (1.96 g, 13.1 mmol) and $K_2CO_3$ (3.62 g, 26.2 mmol) in DMF (28 mL) and the reaction stirred at room temperature for 17 h. The reaction mixture was filtered, and the solids were rinsed with EtOAc. The filtrate was concentrated and purified by silica gel chromatography (hexanes/EtOAc) to afford 2-benzyl 1-tert-butyl (2S,4R)-4-[tert-butoxycarbonyl-[2-(tert-butoxycarbonylamino)ethyl]amino]pyrrolidine-1,2-dicarboxylate (Intermediate 74, 3.91 g, 80% yield) as a white solid. $^1$H NMR (500 MHz, DMSO-$d_6$) δ 1.20-1.47 (27H, m), 2.00-2.13 (1H, m), 2.36-2.45 (1H, m), 2.93-3.01 (2H, m), 3.02-3.26 (3H, m), 3.48-3.64 (1H, m), 4.26-4.43 (2H, m), 5.05-5.22 (2H, m), 6.78-6.93 (1H, m), 7.25-7.41 (5H, m); m/z: ($ES^+$) $[M+H]^+$=564.

Intermediate 75: 2-benzyl 1-tert-butyl (4R)-2-(but-2-enyl)-4-[tert-butoxycarbonyl-[2-(tert-butoxycarbonylamino)ethyl]amino]pyrrolidine-1,2-dicarboxylate 2-Benzyl 1-tert-butyl (2S,4R)-4-[tert-butoxycarbonyl-[2-(tert-butoxycarbonylamino)ethyl]amino]pyrrolidine-1,2-dicarboxylate (Intermediate 74, 3.91 g, 6.94 mmol) and crotyl bromide (0.93 mL, 9.0 mmol) were dissolved in THF (10.6 mL) and the solution was cooled to −78° C. under an atmosphere of $N_2$. A solution of KHMDS (0.5M in toluene, 34.7 mL, 17.3 mmol) was added dropwise to the reaction mixture and the reaction stirred for 17 h while slowly warming to room temperature. The crude reaction mixture was quenched with water and the volatiles were removed under reduced pressure. The crude mixture was diluted in DCM and the layers were separated. The organic layer was washed with water, dried over $Na_2SO_4$, filtered and concentrated to dryness. The crude material was purified by silica gel purification (hexanes/EtOAc) to afford 2-benzyl 1-tert-butyl (4R)-2-(but-2-enyl)-4-[tert-butoxycarbonyl-[2-(tert-butoxycarbonylamino)ethyl]amino]pyrrolidine-1,2-dicarboxylate (Intermediate 75, 1.34 g, 31% yield) as a yellow oil and as a mixture of diastereomers, E/Z olefin isomers and rotamers. $^1$H NMR (500 MHz, DMSO-$d_6$) δ 1.21-1.45 (27H, m), 1.53-1.71 (3H, m), 1.91-2.32 (2H, m), 2.37-2.47 (1H, m), 2.69-2.86 (1H, m), 2.86-3.11 (4H, m), 3.46-3.58 (1H, m), 3.58-3.77 (1H, m), 4.29-4.57 (1H, m), 5.00-5.20 (2H, m), 5.28-5.46 (1H, m), 5.46-5.71 (1H, m), 6.83-7.00 (1H, m), 7.19-7.43 (5H, m); m/z: ($ES^+$) $[M+H]^+$=618.

Intermediate 76: 2-benzyl 1-tert-butyl (4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate Bis(1,5-cyclooctadiene)diiridium(I) dichloride (222 mg, 0.331 mmol) and bis(diphenylphosphino)methane (254 mg, 0.661 mmol) were added to an oven-dried round-bottom flask. The flask was sealed and purged with $N_2$. The solids were dissolved in DCM (9 mL) and 4,4,5,5-tetramethyl-1,3,2-dioxaborolane (1.05 mL, 7.26 mmol) was slowly added to the solution. The reaction was stirred at room temperature for 10 min. 2-Benzyl 1-tert-butyl (4R)-2-(but-2-enyl)-4-[tert-butoxycarbonyl-[2-(tert-butoxycarbonylamino)ethyl]amino]pyrrolidine-1,2-dicarboxylate (Intermediate 75, 2.04 g, 3.30 mmol) was added to the reaction as a solution in DCM (6.1 mL) and the reaction mixture stirred for 16 h at room temperature. The reaction mixture was cooled to 0° C. and carefully quenched with MeOH and water. The layers were separated, and the aqueous layer was extracted with DCM. The combined organics were dried over $Na_2SO_4$, filtered and concentrated to dryness. The resulting residue was purified by flash silica chromatography (hexanes/EtOAc) to afford 2-benzyl 1-tert-butyl (4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate (Intermediate 76, 1.14 g, 46% yield) as a yellow oil and as a mixture of diastereomers and rotamers. The purified material was subjected to chiral SFC [(S,S)Whelk-O1 column, 30×250 mm, 5 μm, Temperature=20° C., Mobile phase=0-20% IPA with 0.2% $NH_4OH$: $CO_2$, UV detection @ 220 nm, loading=18 mg/inj, conc=46 mg/mL in MeOH, flow rate=120 mL/min, Outlet Pressure=100 bar] to give two diastereomers. The stereochemistry of each diastereomer was assigned retrospectively based on the enzyme potency of Example 27 and Example 28 to be congruent with other exemplified compounds.

Intermediate 77 (Isomer 2, 347 mg): 2-benzyl 1-tert-butyl (2R,4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.60-0.76 (2H, m), 1.15 (12H, s), 1.21-1.52 (31H, m), 1.66-1.82 (1H, m), 1.96-2.19 (2H, m), 2.19-2.33 (1H, m), 2.83-3.10 (4H, m), 3.48-3.66 (1H, m), 4.34-4.53 (1H, m), 5.00-5.23 (2H, m), 6.83-6.93 (1H, m), 7.25-7.43 (5H, m).

Intermediate 78 (Isomer 1, 540 mg): 2-benzyl 1-tert-butyl (2S,4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.61-0.76 (2H, m), 1.15 (12H, s), 1.21-1.47 (31H, m), 1.61-1.80 (1H, m), 1.93-2.24 (2H, m), 2.26-2.43 (1H, m), 2.89-3.13 (5H, m), 3.60-3.81 (1H, m), 4.33-4.49 (1H, m), 5.00-5.20 (2H, m), 6.86-6.94 (1H, m), 7.27-7.39 (5H, m).

Intermediate 79: (2R,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid Pd/C (10% wt, 99 mg, 0.093 mmol) was added to a solution of 2-benzyl 1-tert-butyl (2R,4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate (Intermediate 77, 347 mg, 0.465 mmol) in EtOAc (2.3 mL). The flask was equipped with a balloon of H$_2$ and the suspension stirred overnight at room temperature. The reaction mixture was diluted with MeOH and filtered through diatomaceous earth. The filtrate was concentrated to dryness to afford (2R,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid (Intermediate 79, 287 mg, 94% yield) as a white solid which was used without further purification. $^1$H NMR (500 MHz, DMSO-$d_6$) δ 0.65-0.74 (2H, m), 1.14-1.21 (12H, m), 1.31-1.43 (31H, m), 1.66-1.76 (1H, m), 2.00-2.27 (3H, m), 2.96-3.12 (5H, m), 3.37-3.42 (1H, m), 3.49-3.61 (1H, m), 4.34-4.49 (1H, m), 6.84-6.93 (1H, m); m/z: (ES$^+$) [M+H]$^+$=656.

Example 27: (2R,4R)-4-(2-aminoethylamino)-2-(4-boronobutyl)pyrrolidine-2-carboxylic acid Trifluoroacetic acid (0.67 mL, 8.8 mmol) was added dropwise to a stirred solution of (2R,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid (Intermediate 79, 287 mg, 0.438 mmol) in DCM (3.7 mL) at room temperature. After 1 h the solution was concentrated under reduced pressure and the resulting residue was dissolved in 1M HCl aq (5 mL) and Et$_2$O (5 mL). Phenylboronic acid (107 mg, 0.878 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 20 cc column). The desired product was eluted from the column using 5% ammonia in MeOH (20 mL) to afford (2R,4R)-4-(2-aminoethylamino)-2-(4-boronobutyl)pyrrolidine-2-carboxylic acid (Example 27, 106 mg, 89% yield) as a white solid. $^1$H NMR (500 MHz, D$_2$O) δ 0.63-0.77 (2H, m), 1.13-1.23 (1H, m), 1.37 (3H, br d), 1.63-1.76 (1H, m), 1.92-2.02 (1H, m), 2.06-2.14 (1H, m), 2.24-2.33 (1H, m), 2.78 (2H, s), 2.96 (2H, s), 3.08-3.19 (1H, m), 3.28-3.43 (1H, m), 3.43-3.51 (1H, m); m/z: (ES$^+$) [M+H]$^+$=274.

Example 28: (2S,4R)-4-(2-aminoethylamino)-2-(4-boronobutyl)pyrrolidine-2-carboxylic acid

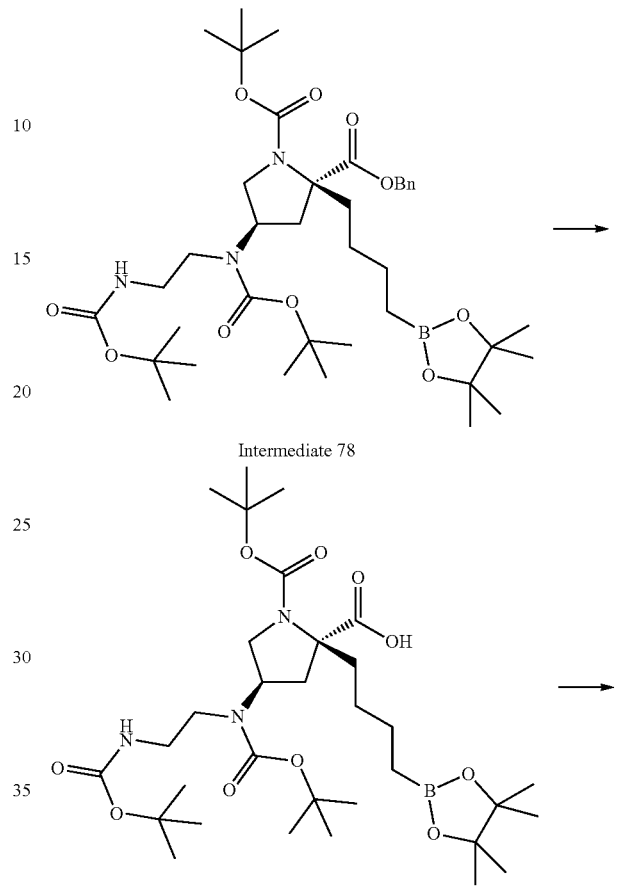

Intermediate 78

Intermediate 80

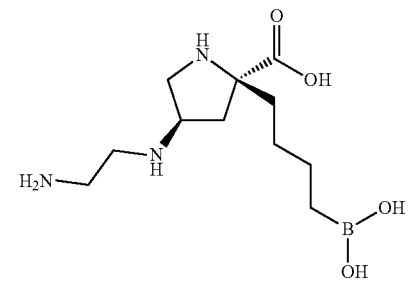

Example 28

Intermediate 80: (2S,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid Pd/C (10% wt, 137 mg, 0.129 mmol) was added to a solution of 2-benzyl 1-tert-butyl (2S,4R)-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-1,2-dicarboxylate (Intermediate 78, 480 mg, 0.64 mmol) in EtOAc (7.2 mL). The flask was equipped with a balloon of H$_2$ and the suspension stirred overnight at room temperature. The reaction mixture was diluted with MeOH and filtered through diatomaceous earth. The filtrate was concentrated to dryness and purified by silica gel chromatography (hexanes/EtOAc) to afford (2S,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid (Intermediate 80, 170 mg, 40% yield) as a white solid. $^1$H NMR (500 MHz, DMSO-d$_6$) δ 0.58-0.73 (2H, m), 1.15 (12H, s), 1.37 (31H, br d), 1.58-1.74 (2H, m), 2.18-2.33 (2H, m), 2.92-3.16 (6H, m), 3.59-3.73 (1H, m), 4.31-4.50 (1H, m), 6.84-6.95 (1H, m); m/z: (ES$^+$) [M+H]$^+$=656.

Example 28: (2S,4R)-4-(2-aminoethylamino)-2-(4-boronobutyl)pyrrolidine-2-carboxylic acid Trifluoroacetic acid (1.00 mL, 13.0 mmol) was added dropwise to a stirred solution of (2S,4R)-1-tert-butoxycarbonyl-4-[tert-butoxycarbonyl-[2-(tert-butoxycarbonylamino)ethyl]amino]-2-[4-(4,4,5,5-tetramethyl-1,3,2-dioxaborolan-2-yl)butyl]pyrrolidine-2-carboxylic acid (Intermediate 80, 170 mg, 0.26 mmol) in DCM (5 mL) at room temperature. After 1 h the solution was concentrated under reduced pressure and the resulting residue was dissolved in 1M HCl aq (5 mL) and Et$_2$O (5 mL). Phenylboronic acid (63 mg, 0.52 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 20 cc column). The desired product was eluted from the column using 5% ammonia in MeOH (20 mL) to afford (2S,4R)-4-(2-aminoethylamino)-2-(4-boronobutyl)pyrrolidine-2-carboxylic acid (Example 28, 67 mg, 95% yield) as a white solid. $^1$H NMR (500 MHz, D$_2$O) δ 0.65-0.77 (2H, m), 1.11-1.24 (1H, m), 1.25-1.34 (1H, m), 1.34-1.42 (2H, m), 1.62-1.79 (2H, m), 1.97-2.06 (1H, m), 2.61-2.70 (1H, m), 2.72-2.84 (2H, m), 2.93 (3H, s), 3.30-3.41 (1H, m), 3.47-3.55 (1H, m); m/z: (ES$^+$) [M+H]$^+$=274.

Example 29: (2R,4R)-4-[[(2S)-2-amino-3-methylbutanoyl]-methyl-amino]-2-(4-boronobutyl)pyrrolidine-2-carboxylic acid

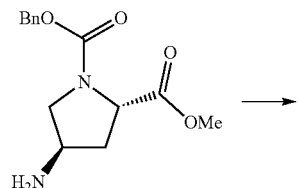

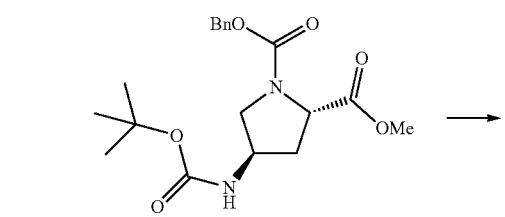

Intermediate 81

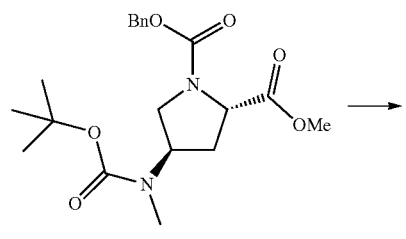

Intermediate 82

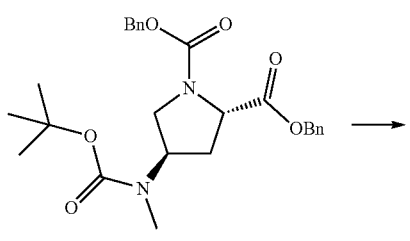

Intermediate 83

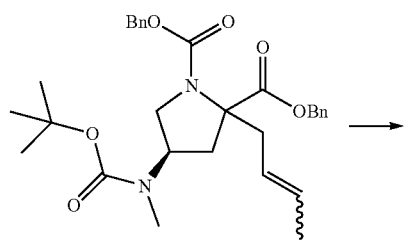

Intermediate 84

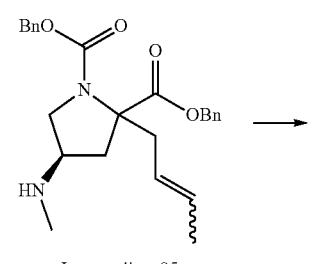

Intermediate 85

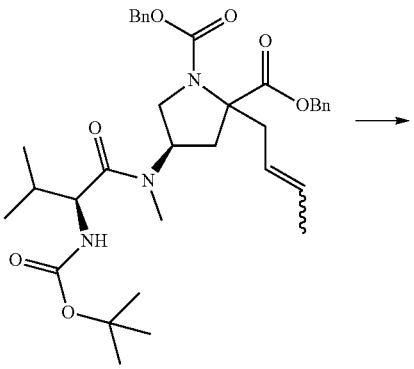

Intermediate 86

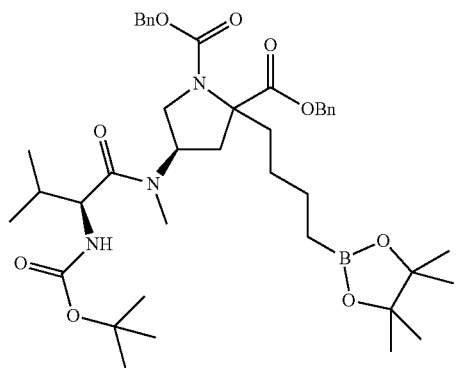

Intermediate 87

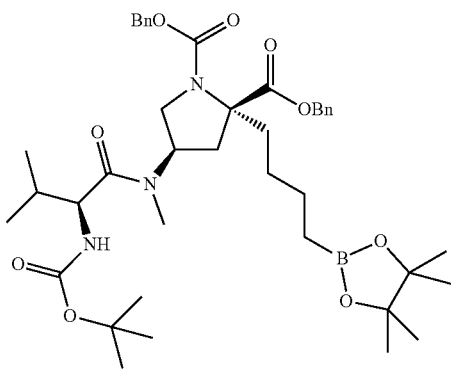

Intermediate 88

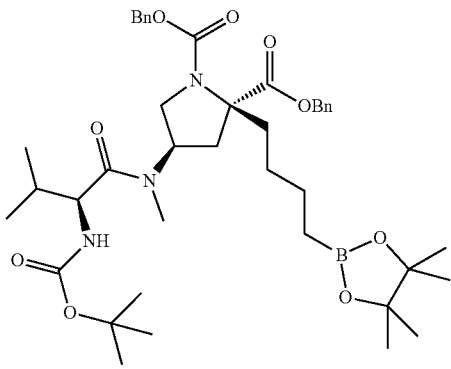

Intermediate 89

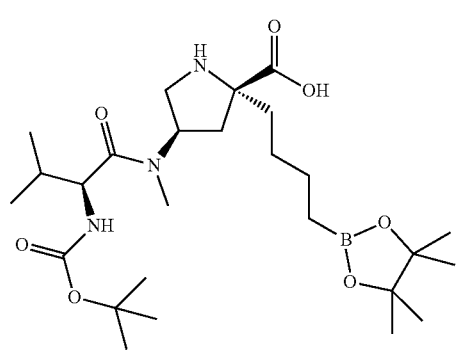

Intermediate 90

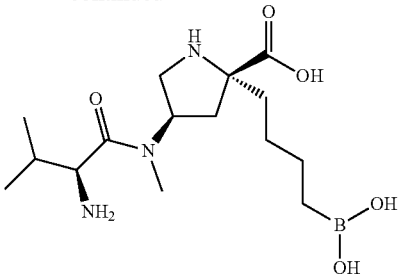

Example 29

Intermediate 81: 1-benzyl 2-methyl (2S,4R)-4-(tert-butoxycarbonylamino)pyrrolidine-1,2-dicarboxylate Di-tert-butyl dicarbonate (6.27 g, 28.8 mmol) was added to a solution of 1-benzyl 2-methyl (2S,4R)-4-aminopyrrolidine-1,2-dicarboxylate (5.00 g, 18.0 mmol) and triethylamine (5.00 mL, 35.9 mmol) in DCM (78 ml) and the reaction stirred at room temperature for 16 h.

The reaction mixture was diluted with DCM and washed sequentially with 0.5 M HCl (aq), saturated sodium bicarbonate and saturated sodium chloride. The organic layer was dried over $Na_2SO_4$, filtered and concentrated to dryness. The crude material was purified by silica gel chromatography (DCM/MeOH) to afford 1-benzyl 2-methyl (2S,4R)-4-(tert-butoxycarbonylamino)pyrrolidine-1,2-dicarboxylate (Intermediate 81, 5.4 g, 79% yield) as a white solid. $^1$H NMR (500 MHz, DMSO-$d_6$) δ 1.31-1.42 (9H, m), 1.99-2.23 (2H, m), 3.22-3.28 (1H, m), 3.52-3.65 (4H, m), 3.96-4.10 (1H, m), 4.30-4.48 (1H, m), 4.92-5.13 (2H, m), 7.18-7.41 (5H, m); m/z: (ES$^+$) [M+H]$^+$=379.

Intermediate 82: 1-benzyl 2-methyl (2S,4R)-4-[tert-butoxycarbonyl(methyl)amino]pyrrolidine-1,2-dicarboxylate Sodium hydride (60% dispersion in mineral oil) (0.423 g, 12.3 mmol) was added portion-wise to a solution 1-benzyl 2-methyl (2S,4R)-4-(tert-butoxycarbonylamino)pyrrolidine-1,2-dicarboxylate (Intermediate 81, 3.20 g, 8.46 mmol) in DMF (33 mL) at 0° C. The reaction mixture stirred at 0° C. for 1 h before warming to room temperature with stirring for an additional 1 h. Methyl iodide (0.63 ml, 10.2 mmol) was added and the reaction stirred at room temperature for 16 h. The reaction mixture was cooled to 0° C. and quenched with water. The volatiles were removed under reduced pressure and the suspension was diluted with DCM (200 mL). The layers were separated, and the organic layer was washed sequentially with water (4×50 mL) and saturated aqueous sodium chloride (2×50 mL). The organic layer was dried over $Na_2SO_4$, filtered and concentrated to dryness to afford 1-benzyl 2-methyl (2S,4R)-4-[tert-butoxycarbonyl(methyl) amino]pyrrolidine-1,2-dicarboxylate (Intermediate 82, 2.33 g, 70% yield) as a colorless oil which was used without further purification. $^1$H NMR (500 MHz, DMSO-$d_6$) δ 1.25-1.47 (9H, m), 1.89-2.08 (1H, m), 2.31-2.46 (1H, m), 2.69 (3H, d), 3.22-3.39 (2H, m), 3.65 (4H, s), 4.22-4.49 (1H, m), 4.87-5.17 (2H, m), 7.18-7.46 (5H, m); m/z: (ES$^+$) [M+H]$^+$=393.

Intermediate 83: dibenzyl (2S,4R)-4-[tert-butoxycarbonyl(methyl)amino]pyrrolidine-1,2-dicarboxylate A solution of sodium hydroxide (1.425 g, 35.62 mmol) in water (7.5 mL) was added to a solution of 1-benzyl 2-methyl (2S,4R)-4-[tert-butoxycarbonyl(methyl)amino]pyrrolidine-1,2-dicarboxylate (Intermediate 82, 2.33 g, 5.94 mmol) in THF (15 mL) and MeOH (7.5 mL) at 0° C. The reaction mixture stirred for 6 hrs while slowly warming to room temperature. The volatiles were removed under reduced pressure and the aqueous layer was acidified to pH ~3 with 5 M HCl (aq) and extracted with DCM (4×50 mL). The combined organics were dried over Na$_2$SO$_4$, filtered and concentrated in dryness to afford the crude carboxylic acid as a white solid which was used without further purification.

Benzyl bromide (0.66 mL, 5.6 mmol) was added to a solution of the crude carboxylic acid, sodium iodide (1.11 g, 7.38 mmol) and K$_2$CO$_3$ (1.92 g, 13.9 mmol) in DMF (28 mL) and the reaction stirred at room temperature for 17 h. The reaction mixture was filtered, and the solids were rinsed with EtOAc. The filtrate was concentrated and purified by silica gel chromatography (hexanes/EtOAc) to afford dibenzyl (2S,4R)-4-[tert-butoxycarbonyl(methyl)amino]pyrrolidine-1,2-dicarboxylate (Intermediate 83, 2.45 g, 94% yield) as a pale-yellow oil. $^1$H NMR (500 MHz, DMSO-d$_6$) δ 1.28-1.45 (9H, m), 1.98 (1H, s), 2.30-2.46 (1H, m), 2.64-2.71 (3H, m), 3.30 (1H, s), 3.51-3.76 (1H, m), 4.48 (1H, d), 4.53-4.75 (1H, m), 4.88-5.21 (4H, m), 7.18-7.42 (10H, m); m/z: (ES$^+$) [M+H]$^+$=469.

Intermediate 84: dibenzyl (4R)-2-(but-2-enyl)-4-[tert-butoxycarbonyl(methyl)amino]pyrrolidine-1,2-dicarboxylate Dibenzyl (2S,4R)-4-[tert-butoxycarbonyl(methyl)amino]pyrrolidine-1,2-dicarboxylate (Intermediate 83, 2.45 g, 5.23 mmol) and crotyl bromide (0.81 mL, 7.8 mmol) were dissolved in THF (18 mL) and the solution was cooled to −78° C. under an atmosphere of N$_2$. A solution of KHMDS (0.5M in toluene, 15.7 mL, 7.85 mmol) was added dropwise to the reaction mixture and the reaction stirred for 17 h while slowly warming to room temperature. The crude reaction mixture was quenched with water and the volatiles were removed under reduced pressure. The crude mixture was diluted in DCM and the layers were separated. The organic layer was washed with water, dried over Na$_2$SO$_4$, filtered and concentrated to dryness. The crude material was purified by silica gel purification (hexanes/EtOAc) to afford dibenzyl (4R)-2-(but-2-enyl)-4-[tert-butoxycarbonyl(methyl)amino]pyrrolidine-1,2-dicarboxylate (Intermediate 84, 2.10 g, 86% yield) as a yellow oil and as a mixture of diastereomers, E/Z olefin isomers and rotamers. $^1$H NMR (500 MHz, DMSO-d$_6$) δ 1.31-1.40 (9H, m), 1.46-1.68 (3H, m), 1.99-2.31 (2H, m), 2.40-2.47 (1H, m), 2.55-2.68 (3H, m), 2.69-3.00 (1H, m), 3.30 (1H, s), 3.51-3.77 (1H, m), 4.55-4.74 (1H, m), 4.79-5.21 (4H, m), 5.26-5.41 (1H, m), 5.42-5.71 (1H, m), 7.16-7.42 (10H, m); m/z: (ES$^+$) [M+H]$^+$=523.

Intermediate 85: dibenzyl (4R)-2-(but-2-enyl)-4-(methylamino)pyrrolidine-1,2-dicarboxylate Trifluoroacetic acid (3.84 mL, 50.2 mmol) was added dropwise to a solution of dibenzyl (4R)-2-(but-2-enyl)-4-[tert-butoxycarbonyl(methyl)amino]pyrrolidine-1,2-dicarboxylate (Intermediate 84, 2.10 g, 4.02 mmol) in DCM (32 mL) and the reaction stirred at room temperature for 2 h. The reaction mixture was concentrated to dryness to afford the TFA salt of dibenzyl (4R)-2-(but-2-enyl)-4-(methylamino)pyrrolidine-1,2-dicarboxylate (Intermediate 85, 2.55 g, 100% yield) as a colorless oil which was used without purification. $^1$H NMR (500 MHz, DMSO-d$_6$) δ 1.45-1.74 (3H, m), 2.14-2.33 (1H, m), 2.34-2.46 (1H, m), 2.57-2.65 (3H, m), 2.66-3.07 (1H, m), 3.15-3.56 (1H, m), 3.66-3.77 (1H, m), 3.81-4.13 (1H, m), 4.79-5.22 (4H, m), 5.26-5.73 (2H, m), 7.20-7.41 (10H, m), 8.62-8.87 (2H, m); m/z: (ES$^+$) [M+H]$^+$=423.

Intermediate 86: dibenzyl (4R)-2-(but-2-enyl)-4-[[(2S)-2-(tert-butoxycarbonylamino)-3-methyl-butanoyl]-methyl-amino]pyrrolidine-1,2-dicarboxylate N,N-Diisopropylethylamine (0.70 mL, 4.0 mmol) was added to a solution of HATU (1.52, 4.02 mmol) and Boc-Val-OH (873 mg, 4.02 mmol) in DMF (15 mL) and the reaction stirred at room temperature for 30 min. A solution of dibenzyl (4R)-2-(but-2-enyl)-4-(methylamino)pyrrolidine-1,2-dicarboxylate TFA salt (Intermediate 85, 2.16 g, 4.02 mmol) in DMF (15 mL) and N,N-Diisopropylethylamine (0.70 mL, 4.0 mmol) were added and the reaction stirred at room temperature for an additional 17 h. The reaction mixture was concentrated and directly purified by silica gel chromatography (hexanes/EtOAc) to afford dibenzyl (4R)-2-(but-2-enyl)-4-[[(2S)-2-(tert-butoxycarbonylamino)-3-methyl-butanoyl]-methyl-amino]pyrrolidine-1,2-dicarboxylate (Intermediate 86, 1.97 g, 79% yield) as a mixture of rotamers. $^1$H NMR (500 MHz, DMSO-d$_6$) 5 $^1$H NMR (500 MHz, DMSO-d$_6$) 0.61-0.92 (6H, m), 1.35 (9H, br s), 1.62 (3H, br d), 1.79-1.92 (1H, m), 2.03-2.33 (2H, m), 2.57-2.76 (2H, m), 2.76-3.00 (3H, m), 3.30 (1H, s), 3.49-3.77 (1H, m), 4.04-4.16 (1H, m), 4.78-5.20 (5H, m), 5.26-5.72 (2H, m), 6.72-7.03 (1H, m), 7.17-7.38 (10H, m); m/z: (ES$^+$) [M+H]$^+$=622.

Intermediate 87: dibenzyl (4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate Bis(1,5-cyclooctadiene)diiridium(I) dichloride (213 mg, 0.317 mmol) and bis(diphenylphosphino)methane (244 mg, 0.635 mmol) were added to an oven-dried round-bottom flask. The flask was sealed and purged with N$_2$. The solids were dissolved in DCM (8.9 mL) and 4,4,5,5-tetramethyl-1,3,2-dioxaborolane (1.01 mL, 6.97 mmol) was slowly added to the solution. The reaction was stirred at room temperature for 10 min. Dibenzyl (4R)-2-(but-2-enyl)-4-[[(2S)-2-(tert-butoxycarbonylamino)-3-methyl-butanoyl]-methyl-amino]pyrrolidine-1,2-dicarboxylate (Intermediate 86, 1.97 g, 3.17 mmol) was added to the reaction as a solution in DCM (5.9 mL) and the reaction mixture stirred for 16 h at room temperature. The reaction mixture was cooled to 0° C. and carefully quenched with MeOH and water. The layers were separated, and the aqueous layer was extracted with DCM. The combined organics were dried over Na$_2$SO$_4$, filtered and concentrated to dryness. The resulting residue was purified by flash silica chromatography (hexanes/EtOAc) to afford dibenzyl (4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate (Intermediate 87, 1.5 g, 63% yield) as a yellow oil and as a mixture of diastereomers and rotamers. The purified material was subjected to chiral SFC [(S,S)Whelk-O1 column, 30×250 mm, 5 μm, Temperature=20° C., Mobile phase=0-30% MeOH:CO2, UV detection @ 220 nm, loading=31 mg/inj, conc=125 mg/mL in MeOH, flow rate=75 mL/min, Outlet Pressure=100 bar] to give two diastereomers. The stereochemistry of each diastereomer was assigned retrospectively based on the enzyme potency of Example 29 and Example 30 to be congruent with other exemplified compounds.

Intermediate 88 (Isomer 2, 280 mg): dibenzyl (2R,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.51-0.70 (2H, m), 0.72-0.93 (6H, m), 1.14 (12H, s), 1.20-1.52 (13H, m), 1.67-2.31 (5H, m), 2.54-2.90 (3H, m), 3.33-3.48 (1H, m), 3.49-3.85 (1H, m), 4.01-4.18 (1H, m), 4.71-5.23 (5H, m), 6.71-7.07 (1H, m), 7.19-7.33 (10H, m).

Intermediate 89 (Isomer 1, 590 mg): dibenzyl (2S,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate. $^1$H NMR (500 MHz, DMSO-$d_6$) δ 0.49-0.72 (2H, m), 0.73-0.90 (6H, m), 1.15 (12H, s), 1.34 (13H, br s), 1.59-2.34 (5H, m), 2.94 (3H, br s), 3.30 (1H, s), 3.63-3.76 (1H, m), 3.96-4.17 (1H, m), 4.75-5.18 (5H, m), 6.71-7.05 (1H, m), 7.17-7.41 (10H, m).

Intermediate 90: (2R,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid Pd/C (10% wt, 99 mg, 0.093 mmol) was added to a solution of dibenzyl (2R,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate (Intermediate 88, 280 mg, 0.37 mmol) in EtOAc (1.8 mL). The flask was equipped with a balloon of $H_2$ and the suspension stirred at room temperature for 4 h. The reaction mixture was diluted with MeOH and filtered through diatomaceous earth. The filtrate was concentrated to dryness to afford (2R,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid (Intermediate 90, 180 mg, 92% yield) as a white solid which was used without further purification. $^1$H NMR (500 MHz, DMSO-$d_6$) δ 0.59-0.69 (2H, m), 0.74-0.87 (6H, m), 1.16 (12H, s), 1.22-1.30 (3H, m), 1.35 (9H, s), 1.49-1.65 (1H, m), 1.65-1.82 (1H, m), 1.82-1.95 (2H, m), 2.15-2.26 (1H, m), 2.63-2.91 (3H, m), 2.92-3.21 (3H, m), 4.05-4.22 (1H, m), 4.80-5.16 (1H, m), 6.76 (1H, s), 7.56-8.05 (1H, m); m/z: (ES$^+$) [M+H]$^+$=526.

Example 29: (2R,4R)-4-[[(2S)-2-amino-3-methyl-butanoyl]-methyl-amino]-2-(4-boronobutyl)pyrrolidine-2-carboxylic acid Trifluoroacetic acid (0.53 mL, 6.9 mmol) was added dropwise to a stirred solution of (2R,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid (Intermediate 90, 180 mg, 0.34 mmol) in DCM (10 mL) at room temperature. After 1 h the solution was concentrated under reduced pressure and the resulting residue was dissolved in 1M HCl aq (5 mL) and Et$_2$O (5 mL). Phenylboronic acid (84 mg, 0.69 mmol) was added and the clear biphasic solution stirred at room temperature for 1 h. The mixture was diluted with Et$_2$O and water and the layers were separated. The aqueous layer was washed with Et$_2$O. The aqueous layer was lyophilized and purified by ion exchange chromatography (PoraPak Rxn CX 60 cc column). The desired product was eluted from the column using 5% ammonia in MeOH (60 mL) to afford (2R,4R)-4-[[(2S)-2-amino-3-methyl-butanoyl]-methyl-amino]-2-(4-boronobutyl)pyrrolidine-2-carboxylic acid (Example 29, 98 mg, 86% yield) as a white solid. $^1$H NMR (500 MHz, D$_2$O) δ 0.72-0.83 (2H, m), 0.85-1.01 (6H, m), 1.10-1.45 (4H, m), 1.61-1.84 (1H, m), 1.85-2.03 (2H, m), 2.19-2.34 (1H, m), 2.34-2.49 (1H, m), 3.00 (3H, s), 3.16-3.51 (2H, m), 3.76-3.96 (1H, m), 4.95-5.10 (1H, m); m/z: (ES$^+$) [M+H]$^+$=344.

Example 30: (2S,4R)-4-[[(2S)-2-amino-3-methyl-butanoyl]-methyl-amino]-2-(4-boronobutyl)pyrrolidine-2-carboxylic acid

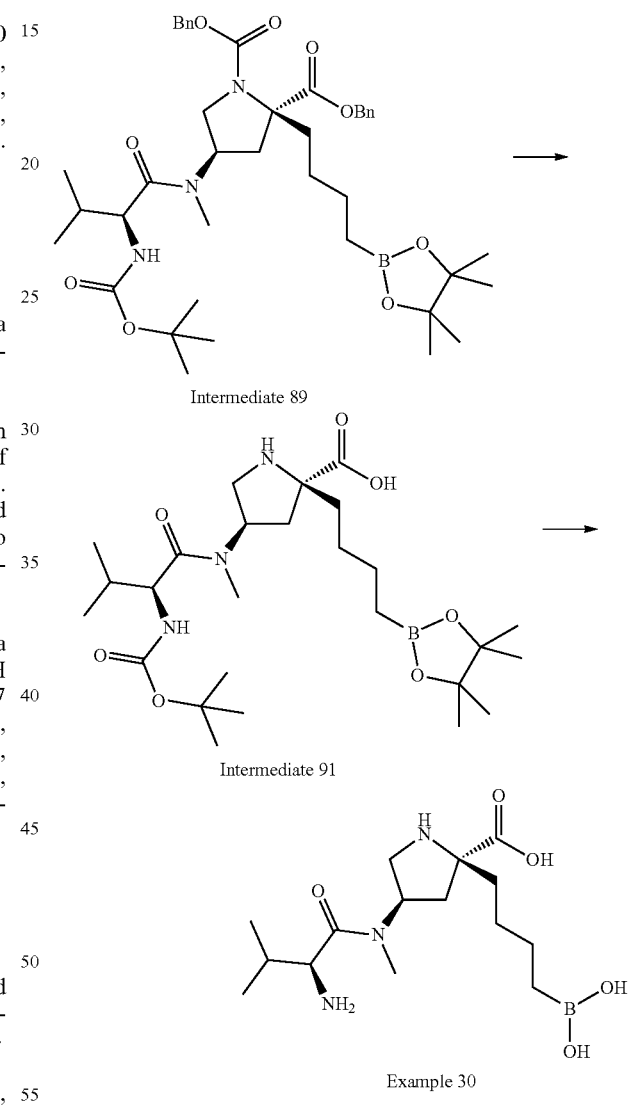

Intermediate 89

Intermediate 91

Example 30

Intermediate 91: (2S,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid Pd/C (10% wt, 209 mg, 0.196 mmol) was added to a solution of dibenzyl (2S,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-1,2-dicarboxylate (Intermediate 89, 590 mg, 0.79 mmol) in EtOAc (4 mL). The flask was equipped with a balloon of $H_2$ and the suspension stirred overnight at room temperature. The reaction mixture was diluted with MeOH and filtered through diatomaceous earth. The filtrate was concentrated to dryness to afford (2S,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid (Intermediate 91, 397 mg, 96% yield) as a white solid which was used without further purification. $^1$H NMR (500 MHz, DMSO-$d_6$) δ 0.58-0.67 (2H, m), 0.73-0.87 (6H, m), 1.16 (12H, s), 1.22-1.31 (3H, m), 1.35 (9H, s), 1.51-1.67 (1H, m), 1.68-1.95 (3H, m), 2.28-2.37 (2H, m), 2.95 (4H, s), 4.05-4.20 (1H, m), 4.66-4.79 (1H, m), 6.65-6.90 (1H, m), 7.85-8.15 (1H, m); m/z: (ES$^+$) [M+H]$^+$=526.

Example 30: (2S,4R)-4-[[(2S)-2-amino-3-methyl-butanoyl]-methyl-amino]-2-(4-boronobutyl)pyrrolidine-2-carboxylic acid Trifluoroacetic acid (1.17 mL, 15.2 mmol) was added dropwise to a stirred solution of (2S,4R)-4-[[(2S)-2-(tert-butoxycarbonylamino)-3-methyl-butanoyl]-methyl-amino]-2-[4-(4,4,5,5-tetramethyl-1,3,2-dioxaborolan-2-yl)butyl]pyrrolidine-2-carboxylic acid (Intermediate 91, 397 mg, 0.755 mmol) in DCM (10 mL) at room temperature. After 1 h the solution was concentrated under reduced pressure and the resulting residue was dissolved in 1M HCl aq (5 mL) and $Et_2O$ (5 mL). Phenylboronic acid (186 mg, 1.52 mmol) was added and the clear biphasic solution stirred at room temperature for 1 h. The mixture was diluted with $Et_2O$ and water and the layers were separated. The aqueous layer was washed with $Et_2O$. The aqueous layer was lyophilized and purified by ion exchange chromatography (PoraPak Rxn CX 60 cc column). The desired product was eluted from the column using 5% ammonia in MeOH (60 mL) to afford (2S,4R)-4-[[(2S)-2-amino-3-methyl-butanoyl]-methyl-amino]-2-(4-boronobutyl)pyrrolidine-2-carboxylic acid (Example 30, 163 mg, 92% yield) as a white solid. $^1$H NMR (500 MHz, $D_2O$) δ 0.68-0.78 (2H, m), 0.83-0.94 (6H, m), 1.10-1.41 (4H, m), 1.66-2.13 (4H, m), 2.49-2.68 (1H, m), 3.02 (3H, s), 3.22-3.30 (1H, m), 3.43-3.60 (1H, m), 3.70-3.88 (1H, m), 4.53-4.66 (1H, m); m/z: (ES$^+$) [M+H]$^+$=344.

Example 31: Biological Activity of Examples 1 to 30

The inhibitory effects of Examples 1 to 30 on the activity of Human Arginase 1 and Arginase 2 activity were quantified by measuring the formation of the thiol group from thioarginine using recombinant Arginase 1 or Arginase 2 produced from E. coli. The thiol group was detected with Ellman's reagent, 5,5'-dithiobis(2-nitrobenzoic acid) (DTNB). DTNB reacts with the thiol to give the mixed disulfide and 2-nitro-5-thiobenzoic acid (TNB) which is quantified by the absorbance of the anion (TNB$^{2-}$) at 412 nm.

The assays were run in clear 384 well plates (Greiner cat no: 781101). Various concentrations of Examples 1 to 30 in 300 nL DMSO were dispensed to assay plates using an Echo acoustic dispenser immediately followed by plate sealing and centrifugation. Two pre-mixes were prepared from reagents thawed immediately before addition to assay plates. Pre-mix one comprised human Arginase 1 or human Arginase 2, at a final concentration of 5 nM and 0.5 mM DTNB in assay buffer, 45 mM HEPES pH7.5, brij 35, 0.045% (w/v) and 100 μM $MnCl_2$. Pre-mix two comprised freshly thawed 0.5 mM thioarginine in assay buffer. Fifteen microlitres of pre-mix one was dispensed to assay plates containing Examples 1 to 30, centrifuged and incubated for 30 minutes at room temperature prior to adding fifteen microlitres of pre-mix two.

Assay plates were centrifuged prior to reading absorbance at 412 nm in a Pherastar multi-mode plate reader to collect data at time point 0 (T0). The plates were incubated at room temperature for 60 min prior to reading again to collect data at time point 1 (T1). Data is derived by subtracting the A412 signal measured at T0 (time point 0) from that measured at T1 (time point 1). The data was transformed to % effect using the equation:

Compound % effect=100*[(X−min)/(max−min)], where X represents the normalized value for the compound based on the Min (vehicle) and Max (reference compound) inhibition control.

The concentration of Examples 1 to 30 that inhibited the activity by 50% (i.e. the $IC_{50}$) was calculated by plotting the % effect versus test compound concentration and fitting the data using the Genedata Screener Smart fit algorithm. The results of these assays are found in Table 2:

TABLE 2

| Example | Human Arginase 1 Enzyme $IC_{50}$ (μM) | Human Arginase 2 Enzyme $IC_{50}$ (μM) |
|---|---|---|
| 1 | 14.69 | 22.98 |
| 2 | 26.57 | 21.44 |
| 3 | 4.55 | 10.40 |
| 4 | 41.92 | 74.07 |
| 5 | 6.41 | 16.63 |
| 6 | 3.96 | 10.41 |
| 7 | 0.01 | 0.02 |
| 8 | 0.61 | 0.56 |
| 9 | 0.32 | 0.33 |
| 10 | 3.77 | 4.77 |
| 11 | 0.21 | 0.20 |
| 12 | 0.70 | 0.85 |
| 13 | 0.43 | 0.63 |
| 14 | 0.26 | 0.31 |
| 15 | 0.31 | 0.26 |
| 16 | 0.31 | 0.31 |
| 17 | 0.20 | 0.23 |
| 18 | 0.32 | 0.38 |
| 19 | 0.22 | 0.28 |
| 20 | 0.34 | 0.52 |
| 21 | 0.48 | 0.68 |
| 22 | 0.93 | 1.32 |
| 23 | 1.14 | 2.12 |
| 24 | <0.003 | 0.01 |
| 25 | 10.80 | 24.55 |
| 26 | 0.06 | 0.15 |
| 27 | 1.43 | 3.32 |
| 28 | 0.09 | 0.19 |
| 29 | 5.27 | 9.28 |
| 30 | 1.35 | 2.42 |

Example 32: Bioavailability Studies

Examples 8, 9, and 13 to 20 are prodrug forms of Example 7. The following pharmacokinetic study was performed to demonstrate bioavailability of Example 7 from Example 8. Example 8 was formulated in 0.9% w/v saline pH 4 (adjusted with 1M HCl) for IV dosing. The formulation was dosed at 2 mg/kg by femoral catheter to two male rats each (170-250 g). Jugular vein catheter serial blood samples were taken at 0.033, 0.083, 0.167, 0.5, 1, 2, 4, 8, and 24 hrs post-dose. For PO dosing, Example 8 was formulated in deionized water pH 4 (adjusted with 1M HCl) and dosed at 5 mg/kg by oral gavage to two male rats each (170-250 g).

Serial blood samples were taken by jugular vein catheter at 0.25, 0.5, 1, 1.5, 2, 3, 4, 8, and 24 hrs post dose. Plasma samples were generated from blood using low speed centrifugation. A single set of calibration standards containing Example 7 and Example 8 were prepared by spiking blank plasma. The samples and standards were extracted by precipitation with two volumes of acetonitrile followed by centrifugation. The results obtained were used to determine the Cl (mL/min/kg), Vdss (L/kg), Cmax (µM), AUC (µM h), tmax (h), and % F for both Example 7 and Example 8. Absolute bioavailability was determined by comparing the PO dose normalized AUC of Example 7 when dosed as Example 8, versus the dose normalized IV AUC of Example 7 when dosed as Example 7. Where appropriate, measured and not nominal doses were used to calculate bioavalability. In an analogous fashion, the same procedure was repeated for Examples 9 and 13 to 20. The results are shown in Tables 3 to 12. These results indicate that bioavailability may be increased by incorporating certain amino acid moieties as prodrugs.

TABLE 3

| | Example 8 | Example 7 |
|---|---|---|
| Cl (mL/min/kg) | NV # | 8.90 * |
| Vdss (L/kg) | NV # | 0.26 * |
| PO Cmax (µM) | NV # | 3.60 # |
| PO AUC (µM · h) | NV # | 10.40 # |
| Tmax (h) | NV # | 1.00 # |
| % F | NV # | 33.00 # | observed value when dosed a pro-drug
* Observed value when dosed as payload.
NV No reportable value

TABLE 4

| | Example 9 | Example 7 |
|---|---|---|
| Cl (mL/min/kg) | 33.30 # | 8.90 * |
| Vdss (L/kg) | 0.20 # | 0.26 * |
| PO Cmax (µM) | 0.60 # | 5.70 # |
| PO AUC (µM · h) | 0.24 # | 16.80 # |
| Tmax (h) | 0.25 # | 1.00 # |
| % F | 3.20 # | 59.00 # | observed value when dosed a pro-drug
* Observed value when dosed as payload.
NV No reportable value

TABLE 5

| | Example 13 | Example 7 |
|---|---|---|
| Cl (mL/min/kg) | 17.90 # | 8.90 * |
| Vdss (L/kg) | 0.20 # | 0.26 * |
| PO Cmax (µM) | 0.46 # | 3.30 # |
| PO AUC (µM · h) | 0.62 # | 13.30 # |
| Tmax (h) | 0.50 # | 1.25 # |
| % F | 3.80 # | 40.70 # | observed value when dosed a pro-drug
* Observed value when dosed as payload.
NV No reportable value

TABLE 6

| | Example 14 | Example 7 |
|---|---|---|
| Cl (mL/min/kg) | NV # | 8.90 * |
| Vdss (L/kg) | NV # | 0.26 * |
| PO Cmax (µM) | NV # | 3.80 # |

TABLE 6-continued

| | Example 14 | Example 7 |
|---|---|---|
| PO AUC (µM · h) | NV # | 8.90 # |
| Tmax (h) | NV # | 1.00 # |
| % F | NV # | 29.90 # | observed value when dosed a pro-drug
* Observed value when dosed as payload.
NV No reportable value

TABLE 7

| | Example 15 | Example 7 |
|---|---|---|
| Cl (mL/min/kg) | 104.00 # | 8.90 * |
| Vdss (L/kg) | 0.46 # | 0.26 * |
| PO Cmax (µM) | NV # | 5.70 # |
| PO AUC (µM · h) | NV # | 15.60 # |
| Tmax (h) | NV # | 1.00 # |
| % F | NV # | 57.10 # | observed value when dosed a pro-drug
* Observed value when dosed as payload.
NV No reportable value

TABLE 8

| | Example 16 | Example 7 |
|---|---|---|
| Cl (mL/min/kg) | 585.00 # | 8.90 * |
| Vdss (L/kg) | 7.41 # | 0.26 * |
| PO Cmax (µM) | NV # | 1.60 # |
| PO AUC (µM · h) | NV # | 5.80 # |
| Tmax (h) | NV # | 1.00 # |
| % F | NV # | 17.00 # | observed value when dosed a pro-drug
* Observed value when dosed as payload.
NV No reportable value

TABLE 9

| | Example 17 | Example 7 |
|---|---|---|
| Cl (mL/min/kg) | 40.50 # | 8.90 * |
| Vdss (L/kg) | 0.36 # | 0.26 * |
| PO Cmax (µM) | 0.43 # | 4.90 # |
| PO AUC (µM · h) | 0.38 # | 18.30 # |
| Tmax (h) | 0.38 # | 1.50 # |
| % F | 5.80 # | 61.90 # | observed value when dosed a pro-drug
* Observed value when dosed as payload.
NV No reportable value

TABLE 10

| | Example 18 | Example 7 |
|---|---|---|
| Cl (mL/min/kg) | 317.00 # | 8.90 * |
| Vdss (L/kg) | 0.64 # | 0.26 * |
| PO Cmax (µM) | NV # | 4.10 # |
| PO AUC (µM · h) | NV # | 13.10 # |
| Tmax (h) | NV # | 1.50 # |
| % F | NV # | 45.70 # | observed value when dosed a pro-drug
* Observed value when dosed as payload.
NV No reportable value

TABLE 11

|  | Example 19 | Example 7 |
|---|---|---|
| Cl (mL/min/kg) | 36.80 # | 8.90 * |
| Vdss (L/kg) | 0.20 # | 0.26 * |
| PO Cmax (μM) | 0.33 # | 5.70 # |
| PO AUC (μM · h) | 0.21 # | 16.80 # |
| Tmax (h) | 0.25 # | 1.00 # |
| % F | 2.50 # | 59.00 # | observed value when dosed a pro-drug
* Observed value when dosed as payload.
NV No reportable value

TABLE 12

|  | Example 20 | Example 7 |
|---|---|---|
| Cl (mL/min/kg) | 8.90 # | 8.90 * |
| Vdss (L/kg) | 0.29 # | 0.26 * |
| PO Cmax (μM) | 1.80 # | 2.20 # |
| PO AUC (μM · h) | 6.90 # | 12.20 # |
| Tmax (h) | 1.00 # | 3.50 # |
| % F | 25.50 # | 59.00 # | observed value when dosed a pro-drug
* Observed value when dosed as payload.
NV No reportable value

The invention claimed is:

1. A compound of formula (I), or a pharmaceutically acceptable salt thereof:

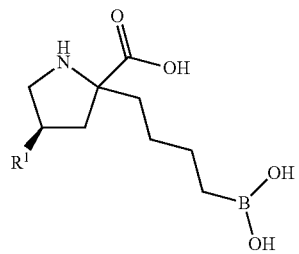

(I)

wherein
$R^1$ is —$NHR^{1a}$;
$R^{1a}$ is —H or —$C(O)CH(R^{1b})NHR^{1c}$; and
$R^{1b}$ is selected from —H, —($C_1$-$C_4$) alkyl and $CH_2OR^{1d}$ and $R^{1c}$ is —H; or
$R^{1b}$ and $R^{1c}$, together with the atom to which they are attached, form a 5-membered heterocyclic ring; and
$R^{1d}$ is H or —$CH_3$.

2. The compound of claim 1 represented by formula (II), or a pharmaceutically acceptable salt thereof:

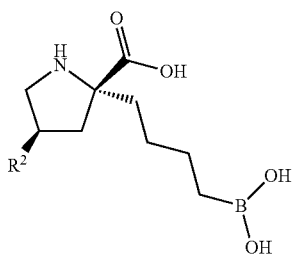

(II)

wherein
$R^2$ is —$NHR^{2a}$;
$R^{2a}$ is —H or —$C(O)CH(R^{2b})NHR^{2c}$;
$R^{2b}$ is selected from —H, —($C_1$-$C_4$) alkyl and $CH_2OR^{2d}$ and $R^{2c}$ is —H; or
$R^{2b}$ and $R^{2c}$, together with the atoms to which they are attached, form a 5-membered heterocyclic ring; and
$R^{2d}$ is —H or —$CH_3$.

3. The compound of claim 1 represented by formula (III), or a pharmaceutically acceptable salt thereof:

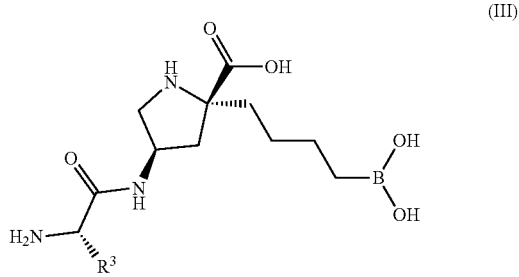

(III)

wherein
$R^3$ is selected from —H, —($C_1$-$C_4$) alkyl and —$CH_2OR^{3a}$; and
$R^{3a}$ is —H or —$CH_3$.

4. The compound of claim 1 represented by formula (IV), or a pharmaceutically acceptable salt thereof:

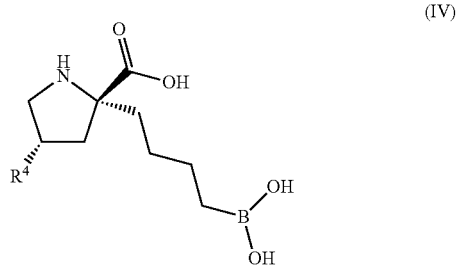

(IV)

wherein $R^4$ is —$NH_2$.

5. The compound of claim 1 represented by formula (V), or a pharmaceutically acceptable salt thereof:

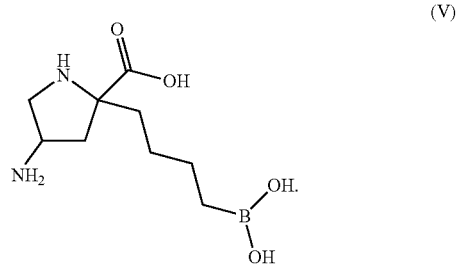 [SMILES: NC1CNC(CCCCB(O)O)(C(=O)O)C1]

(V)

6. A compound of formula (VI), or a pharmaceutically acceptable salt thereof:

(VI)

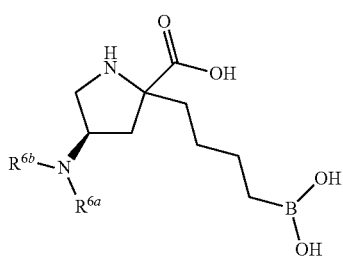

wherein
$R^{6a}$ is —H or —CH$_3$;
$R^{6b}$ is —C(O)C(R$^{6c}$R$^{6d}$)NH$_2$; or —(C$_1$-C$_3$) alkyl which is substituted with 0 or 1 amino or —OR$^{6e}$; and
$R^{6c}$ is —(C$_1$-C$_3$) alkyl which is substituted with 0 or 1 amino or —OR$^{6f}$;
$R^{6d}$ is H or —CH$_3$; and
$R^{6e}$ and $R^{6f}$ are independently —H or —CH$_3$.

7. The compound of claim 6 represented by formula (VI), or a pharmaceutically acceptable salt thereof, wherein
$R^{6a}$ is —H or —CH$_3$; and $R^{6b}$ is —(C$_1$-C$_3$) alkyl which is substituted with 0 or 1 amino; or alternatively, $R^{6a}$ is —H or —CH$_3$; $R^{6b}$ is —C(O)C(R$^{6c}$R$^{6d}$)NH$_2$; $R^{6c}$ is —(C$_1$-C$_3$) alkyl which is substituted with 0 or 1 amino or —OH; and $R^{6d}$ is H or —CH$_3$.

8. A compound of formula (Ib), or a pharmaceutically acceptable salt thereof:

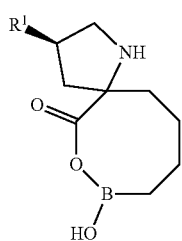

(Ib)

wherein
$R^1$ is —NHR$^{1a}$;
$R^{1a}$ is —H or —C(O)CH(R$^{1b}$)NHR$^{1c}$; and
$R^{1b}$ is selected from —H, —(C$_1$-C$_4$) alkyl and CH$_2$OR$^{1d}$ and $R^{1c}$ is —H; or
$R^{1b}$ and $R^{1c}$, together with the atom to which they are attached, form a 5-membered heterocyclic ring; and
$R^{1d}$ is H or —CH$_3$.

9. The compound of claim 8 represented by formula (IIb), or a pharmaceutically acceptable salt thereof:

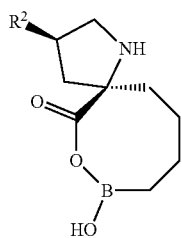

(IIb)

wherein
$R^2$ is —NHR$^{2a}$;
$R^{2a}$ is —H or —C(O)CH(R$^{2b}$)NHR$^{2c}$;
$R^{2b}$ is selected from —H, —(C$_1$-C$_4$) alkyl and CH$_2$OR$^{2d}$ and $R^{2c}$ is —H; or
$R^{2b}$ and $R^{2c}$, together with the atoms to which they are attached, form a 5-membered heterocyclic ring; and
$R^{2d}$ is —H or —CH$_3$.

10. The compound of claim 8 represented by formula (IIIb), or a pharmaceutically acceptable salt thereof:

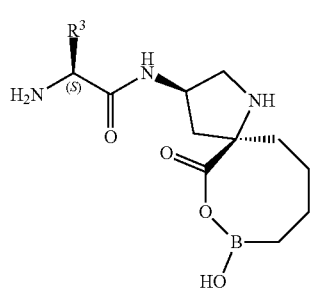

(IIIb)

wherein
$R^3$ is selected from —H, —(C$_1$-C$_4$) alkyl and —CH$_2$OR$^{3a}$; and
$R^{3a}$ is —H or —CH$_3$.

11. The compound of claim 8 represented by formula (IVb), or a pharmaceutically acceptable salt thereof:

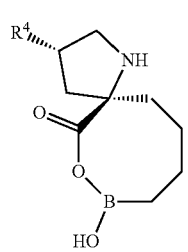

(IVb)

wherein $R^4$ is —NH$_2$.

12. The compound of claim 8 represented by formula (Vb), or a pharmaceutically acceptable salt thereof:

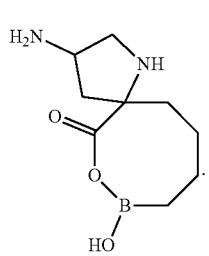

(Vb)

13. A compound of formula (VIb), or a pharmaceutically acceptable salt thereof:

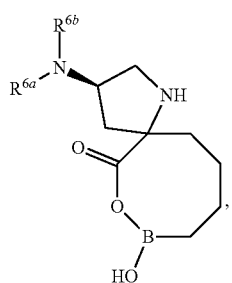

(VIb)

wherein
R$^{6a}$ is —H or —CH$_3$;
R$^{6b}$ is —C(O)C(R$^{6c}$R$^{6d}$)NH$_2$; or —(C$_1$-C$_3$) alkyl which is substituted with 0 or 1 amino or —OR$^{6e}$; and
R$^{6c}$ is —(C$_1$-C$_3$) alkyl which is substituted with 0 or 1 amino or —OR$^{6f}$;
R$^{6d}$ is H or —CH$_3$; and
R$^{6e}$ and R$^{6f}$ are independently —H or —CH$_3$.

14. The compound of claim 13 represented by formula (VIb), or a pharmaceutically acceptable salt thereof; wherein R$^{6a}$ is —H or —CH$_3$; and R$^{6b}$ is —(C$_1$-C$_3$) alkyl which is substituted with 0 or 1 amino; or alternatively, R$^{6a}$ is —H or —CH$_3$; R$^{6b}$ is —C(O)C(R$^{6c}$R$^{6d}$)NH$_2$; R$^{6c}$ is —(C$_1$-C$_3$) alkyl which is substituted with 0 or 1 amino or —OH; and R$^{6d}$ is H or —CH$_3$.

15. A compound, or a pharmaceutically acceptable salt thereof, wherein the compound is selected from

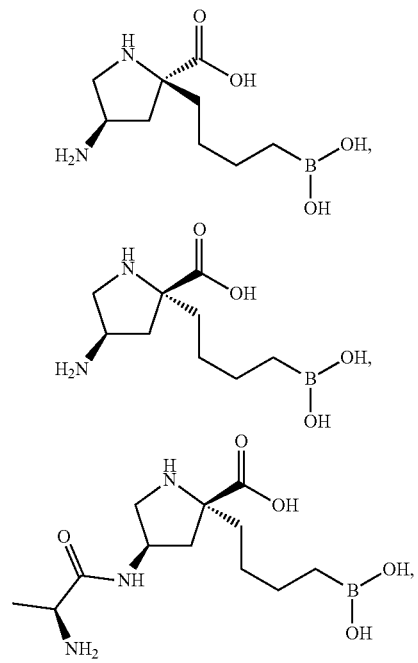

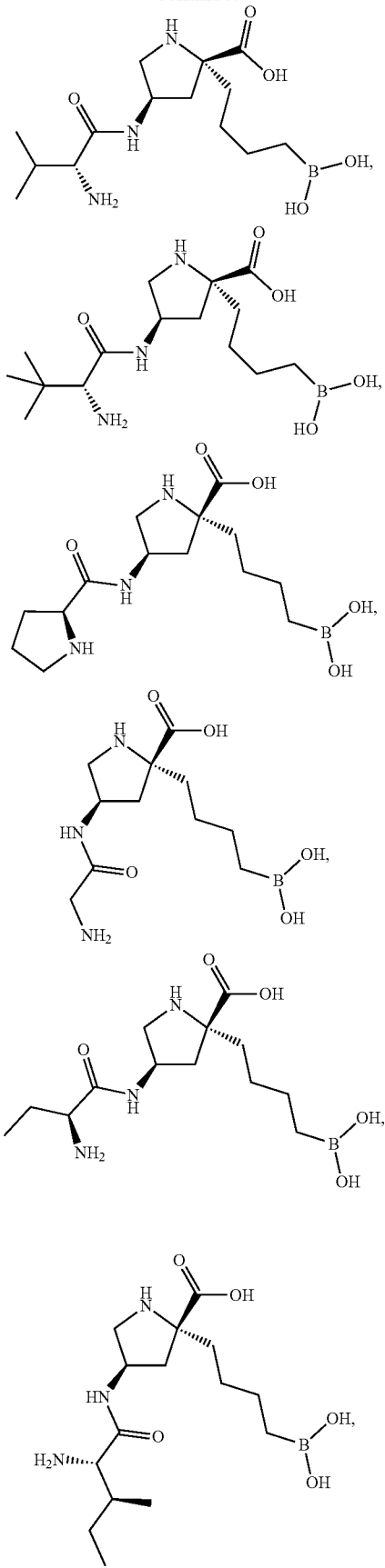

125 -continued
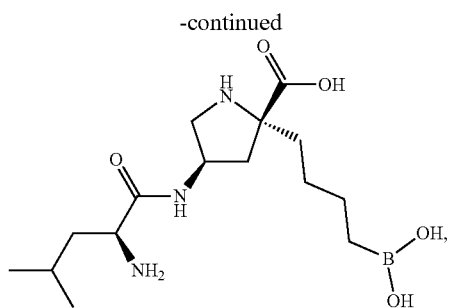
126 -continued
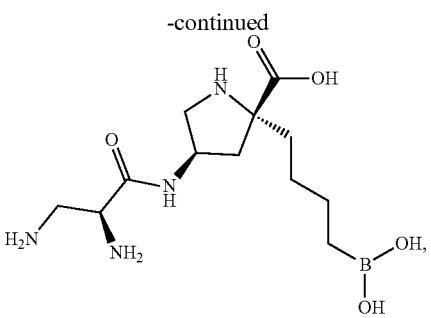
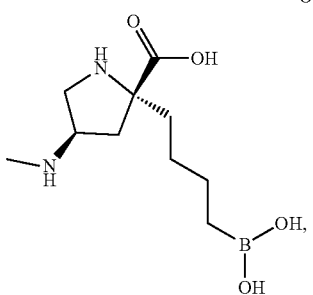
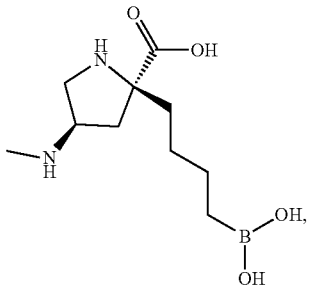
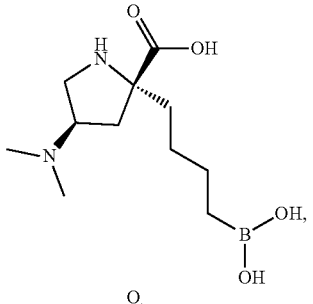
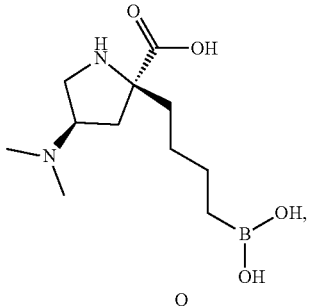
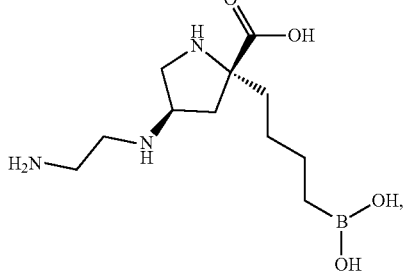

127
-continued

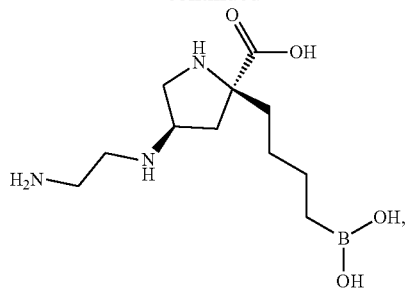

128
-continued

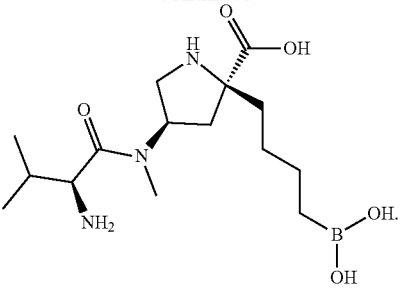

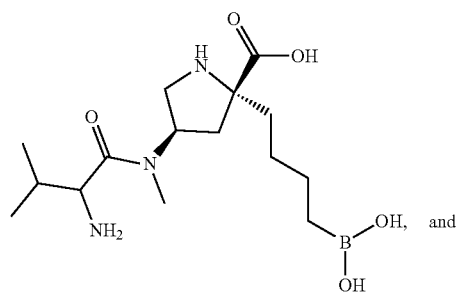
and

16. A pharmaceutical composition comprising a compound of claim 1, or a pharmaceutically acceptable salt thereof, and a pharmaceutically acceptable carrier.

17. A pharmaceutical composition comprising a compound of claim 6, or a pharmaceutically acceptable salt thereof, and a pharmaceutically acceptable carrier.

18. A pharmaceutical composition comprising a compound of claim 8, or a pharmaceutically acceptable salt thereof, and a pharmaceutically acceptable carrier.

19. A pharmaceutical composition comprising a compound of claim 13, or a pharmaceutically acceptable salt thereof, and a pharmaceutically acceptable carrier.

* * * * *